(12) United States Patent
Chauhan et al.

(10) Patent No.: US 11,998,481 B2
(45) Date of Patent: Jun. 4, 2024

(54) METHODS AND COMPOSITIONS FOR IONTOPHORETIC DRUG DELIVERY TO THE EYE

(71) Applicant: University of Florida Research Foundation, Inc., Gainesville, FL (US)

(72) Inventors: Anuj Chauhan, Golden, CO (US); Keith G. Christopher, Palmer, AK (US)

(73) Assignee: University of Florida Research Foundation Inc., Gainesville, FL (US)

( * ) Notice: Subject to any disclaimer, the term of this patent is extended or adjusted under 35 U.S.C. 154(b) by 820 days.

(21) Appl. No.: 17/258,767

(22) PCT Filed: Aug. 2, 2019

(86) PCT No.: PCT/US2019/044945
§ 371 (c)(1),
(2) Date: Jan. 8, 2021

(87) PCT Pub. No.: WO2020/028829
PCT Pub. Date: Feb. 6, 2020

(65) Prior Publication Data
US 2021/0121325 A1    Apr. 29, 2021

Related U.S. Application Data

(60) Provisional application No. 62/713,990, filed on Aug. 2, 2018.

(51) Int. Cl.
*A61F 9/00* (2006.01)
*A61N 1/04* (2006.01)
*A61N 1/30* (2006.01)

(52) U.S. Cl.
CPC .......... *A61F 9/0017* (2013.01); *A61N 1/0436* (2013.01); *A61N 1/044* (2013.01); *A61N 1/303* (2013.01)

(58) Field of Classification Search
CPC ..... A61F 9/0017; A61N 1/0436; A61N 1/044; A61N 1/303
See application file for complete search history.

(56) References Cited

U.S. PATENT DOCUMENTS 5,843,186 A * 12/1998 Christ ................... A61F 9/0017
604/20
2009/0279050 A1   11/2009 McGinn et al.
(Continued)

FOREIGN PATENT DOCUMENTS

EP          1807149 B1     12/2011

OTHER PUBLICATIONS

Nauen, Ralf, et al. "Whitefly-active metabolites of imidacloprid: biological efficacy and translocation in cotton plants." Pesticide Science 55.3 (1999): 265-271.
(Continued)

*Primary Examiner* — Dung T Ulsh
(74) *Attorney, Agent, or Firm* — Thomas | Horstemeyer LLP.

(57) ABSTRACT

In one aspect, the disclosure relates to drug delivery devices for the ionophoretic delivery of a therapeutic agent(s) to the eye. In some aspects, the disclosed ionophoretic ocular delivery device is configured for delivery of a therapeutic agent to the anterior portion of the eye. In various aspects, the present disclosure provides methods for treatment of an ophthalmological disorder, disease, or clinical condition by delivering a therapeutic agent(s) to the eye using a disclosed ionophoretic ocular delivery device. This abstract is intended as a scanning tool for purposes of searching in the particular art and is not intended to be limiting of the present disclosure.

19 Claims, 23 Drawing Sheets

(56) References Cited

U.S. PATENT DOCUMENTS

| | | | |
|---|---|---|---|
| 2009/0281451 | A2* | 11/2009 | Hetling .................. A61B 5/398 600/558 |
| 2016/0213514 | A1* | 7/2016 | Manzo ..................... A61N 1/30 |
| 2016/0296368 | A1* | 10/2016 | Mitsui .................... G02C 7/047 |
| 2018/0101027 | A1 | 4/2018 | Otts et al. |

OTHER PUBLICATIONS

Ng, Tee-Kheang, et al. "Altering the substrate specificity of methyl parathion hydrolase with directed evolution." Archives of biochemistry and biophysics 573 (2015): 59-68.

Ngai, Michelle; et al. "The search for novel insecticide targets in the post-genomics era, with a specific focus on G-protein coupled receptors." Memórias do Instituto Oswaldo Cruz 112.1 (2017): 1-7.

Olofsson, Tobias C., et al. "*Lactobacillus apinorum* sp. nov., *Lactobacillus mellifer* sp. nov., *Lactobacillus mellis* sp. nov., *Lactobacillus melliventris* sp. nov., *Lactobacillus kimbladii* sp. nov., *Lactobacillus helsingborgensis* sp. nov. and *Lactobacillus kullabergensis* sp. nov., isolated from the honey stomach of the honeybee *Apis mellifera*." International journal of systematic and evolutionary microbiology 64.Pt 9 (2014): 3109.

O'Flaherty, Sarah; et al. "Multivalent chromosomal expression of the Clostridium botulinum serotype A neurotoxin heavy-chain antigen and the Bacillus anthracis protective antigen in Lactobacillus acidophilus." Applied and environmental microbiology 82.20 (2016): 6091-6101.

Ohbayashi, Tsubasa, et al. "Insect's intestinal organ for symbiont sorting." Proceedings of the National Academy of Sciences 112.37 (2015): E5179-E5188.

Pain, Janine, and J. Maugenet. "Biochemical and physiological research on pollen stored by bees." The Annals of the Bee 9.3 (1966): 209-236.

Philippe, Nadege, et al. "Improvement of pCVD442, a suicide plasmid for gene allele exchange in bacteria." Plasmid 51.3 (2004): 246-255.

Phillips, J. P., et al. "Transfer and expression of an organophosphate insecticide-degrading gene from Pseudomonas in *Drosophila melanogaster*." Proceedings of the National Academy of Sciences 87.20 (1990): 8155-8159.

Potts, Simon G., et al. "Safeguarding pollinators and their values to human well-being." Nature 540.7632 (2016): 220-229.

Powell, J. Elijah, et al. "Routes of acquisition of the gut microbiota of the honey bee *Apis mellifera*." Applied and environmental microbiology 80.23 (2014): 7378-7387.

Prakash, Om, et al. "Microbial cultivation and the role of microbial resource centers in the omics era." Applied Microbiology and Biotechnology 97.1 (2013): 51-62.

Pritchett, Matthew A.; et al. "Development of a markerless genetic exchange method for Methanosarcina acetivorans C2A and its use in construction of new genetic tools for methanogenic archaea." Applied and Environmental Microbiology 70.3 (2004): 1425-1433.

Purg, Miha, et al. "Probing the mechanisms for the selectivity and promiscuity of methyl parathion hydrolase." Philosophical Transactions of the Royal Society A: Mathematical, Physical and Engineering Sciences 374.2080 (2016): 20160150.

Rader, Romina, et al. "Non-bee insects are important contributors to global crop pollination." Proceedings of the National Academy of Sciences 113.1 (2016): 146-151.

Rangberg, Anbjørg, et al. "Paratransgenesis: an approach to improve colony health and molecular insight in honey pees (*Apis mellifera*)?. " (2012): 89-99.

Rangberg, A., et al. "The paratransgenic potential of Lactobacillus kunkeei in the honey bee *Apis mellifera*." Beneficial microbes 6.4 (2015): 513-523.

Ranson, Hilary, et al. "Evolution of supergene families associated with insecticide resistance." Science 298.5591 (2002): 179-181.

Retschnig, Gina, et al. "Effects, but no interactions, of ubiquitous pesticide and parasite stressors on honey bee (*A pis mellifera*) lifespan and behaviour in a colony environment." Environmental Microbiology 17.11 (2015): 4322-4331.

Ried, Jeffrey L.; et al. "An nptl-sacB-sacR cartridge for constructing directed, unmarked mutations in gram-negative bacteria by marker exchange-eviction mutagenesis." Gene 57.2-3 (1987): 239-246.

Ruiz-Argueso, T., and A. Rodriguez-Navarro. "Microbiology of ripening honey." Applied microbiology 30.6 (1975): 893-896.

Russell, Robyn J., et al. "The evolution of new enzyme function: lessons from xenobiotic metabolizing bacteria versus insecticide-resistant insects." Evolutionary Applications 4.2 (2011): 225-248.

Ryffel, Gerhart U. "Transgene flow: Facts, speculations and possible countermeasures." GM crops & food 5.4 (2014): 249-258.

Sabree, Zakee L.; et al. "Independent studies using deep sequencing resolve the same set of core bacterial species dominating gut communities of honey bees." PloS one 7.7 (2012): e41250.

Saez-Lara, Maria Jose, et al. "The role of probiotic lactic acid bacteria and bifidobacteria in the prevention and treatment of inflammatory bowel disease and other related diseases: a systematic review of randomized human clinical trials." BioMed research international 2015 (2015).

Sanchez-Bayo, Francisco; et al. "Pesticide residues and bees—a risk assessment." PloS one 9.4 (2014): e94482.

Sánchez-Bayo, Francisco, et al. "Are bee diseases linked to pesticides ?—A brief review." Environment international 89 (2016): 7-11.

Schmehl, Daniel R., et al. "Protocol for the in vitro rearing of honey bee (*Apis mellifera* L.) workers." Journal of Apicultural Research 55.2 (2016): 113-129.

Schmuck, Richard; et al. "Field relevance of a synergistic effect observed in the laboratory between an EBI fungicide and a chloronicotinyl insecticide in the honeybee (*Apis mellifera* L, *Hymenoptera*)." Pest Management Science: formerly Pesticide Science 59.3 (2003): 279-286.

Scott, Jeffrey G. "Evolution of resistance to pyrethroid insecticides in Musca domestica." Pest management science 73.4 (2017): 716-722.

Sethi, Amit, et al. "Protozoacidal Trojan-Horse: use of a ligand-lytic peptide for selective destruction of symbiotic protozoa within termite guts." PloS one 9.9 (2014): e106199.

Sih, Andrew; et al. "Two stressors are far deadlier than one." Trends in ecology & evolution 19.6 (2004): 274-276.

Simon, Marie-Christine, et al. "Intake of Lactobacillus reuteri improves incretin and insulin secretion in glucose-tolerant humans: a proof of concept." Diabetes care 38.10 (2015): 1827-1834.

Simpson, Deborah J., et al. "Transformation of Acinetobacter baylyi in non-sterile soil using recombinant plant nuclear DNA." Environmental biosafety research 6.1-2 (2007): 101-112.

Singh, Brajesh K. "Organophosphorus-degrading bacteria: ecology and industrial applications." Nature Reviews Microbiology 7.2 (2009): 156-164.

Singh, Baljinder; et al. "Microbial degradation of an organophosphate pesticide, malathion." Critical reviews in microbiology 40.2 (2014): 146-154.

Suchail, Severine, et al. "In vivo distribution and metabolisation of 14C-imidacloprid in different compartments of *Apis mellifera* L." Pest Management Science: formerly Pesticide Science 60.11 (2004): 1056-1062.

Tago, Kanako, et al. "Insecticide-degrading Burkholderia symbionts of the stinkbug naturally occupy various environments of sugarcane fields in a Southeast island of Japan." Microbes and environments (2014): ME14124.

Teese, Mark G., et al. "Gene identification and proteomic analysis of the esterases of the cotton bollworm, *Helicoverpa armigera*." Insect Biochemistry and Molecular Biology 40.1 (2010): 1-16.

Toiviainen, Aino, et al. "Impact of orally administered lozenges with Lactobacillus rhamnosus GG and *Bifidobacterium animalis* subsp. lactis BB-12 on the number of salivary mutans *streptococci*, amount of plaque, gingival inflammation and the oral microbiome in healthy adults." Clinical oral investigations 19.1 (2015): 77-83.

Turrini, Alessandra; et al. "Belowground environmental effects of transgenic crops: a soil microbial perspective." Research in microbiology 166.3 (2015): 121-131.

(56) References Cited

OTHER PUBLICATIONS

Ueki, Toshiyuki; et al. "Positive-negative KG cassettes for construction of multi-gene deletions using a single drug marker." Gene 183.1-2 (1996): 153-157.
Hayes Jr, Jerry; et al. "A survey of honey bee colony losses in the US, fall 2007 to spring 2008." PloS one 3.12 (2008): e4071.
Dennis vanEngelsdorp; et al. "A historical review of managed honey bee populations in Europe and the United States and the factors that may affect them." Journal of invertebrate pathology 103 (2010): S80-S95.
Dennis vanEngelsdorp; et al. "Idiopathic brood disease syndrome and queen events as precursors of colony mortality in migratory beekeeping operations in the eastern United States." Preventive veterinary medicine 108.2-3 (2013): 225-233.
Vásquez, Alejandra; et al. "A scientific note on the lactic acid bacterial flora in honeybees in the USA—A comparison with bees from Sweden." Apidologie 40.1 (2009): 26-28.
Vásquez, Alejandra, et al. "Symbionts as major modulators of insect health: lactic acid bacteria and honeybees." PloS one 7.3 (2012): e33188.
Wang, Bao-zhan, et al. "Cloning of a novel pyrethroid-hydrolyzing carboxylesterase gene from *Sphingobium* sp. strain JZ-1 and characterization of the gene product." Applied and Environmental Microbiology 75.17 (2009): 5496-5500.
Wang, L-L., et al. "Overexpression of two a-esterase genes mediates metabolic resistance to malathion in the oriental fruit fly, *Bactrocera dorsalis* (Hendel)." Insect molecular biology 24.4 (2015): 467-479.
Werren, John H. "Symbionts provide pesticide detoxification." Proceedings of the National Academy of Sciences 109.22 (2012): 8364-8365.
Gilliam, Martha. "Microbiology of pollen and bee bread: the genus *Bacillus*." Apidologie 10.3 (1979): 269-274.
Gilliam, Martha; et al. "Microbiology of feces of the larval honey bee, *Apis mellifera*." Journal of invertebrate pathology 49.1 (1987): 70-75.
Gilliam, Martha. "Microbial sterility of the intestinal content of the immature honey bee, *Apis mellifera*." Annals of the Entomological Society of America 64.1 (1971): 315-316.
Goh, Yong Jun, et al. "Development and application of a upp-based counterselective gene replacement system for the study of the S-layer protein SlpX of Lactobacillus acidophilus NCFM." Applied and environmental microbiology 75.10 (2009): 3093-3105.
Gómez-Gallego, Carlos, et al. "A canine-specific probiotic product in treating acute or intermittent diarrhea in dogs: a double-blind placebo-controlled efficacy study." Veterinary microbiology 197 (2016): 122-128.
Gong, Youhui; et al. "Current knowledge of detoxification mechanisms of xenobiotic in honey bees." Ecotoxicology 26.1 (2017): 1-12.
Goulson, Dave, et al. "Bee declines driven by combined stress from parasites, pesticides, and lack of flowers." Science 347.6229 (2015).
Gregorc, Ales; et al. "Cell death localization in situ in laboratory reared honey bee (*Apis mellifera* L.) larvae treated with pesticides." Pesticide biochemistry and physiology 99.2 (2011): 200-207.
Gregorc, Aleš, et al. "Gene expression in honey bee (*Apis mellifera*) larvae exposed to pesticides and Varroa mites (*Varroa destructor*)." Journal of Insect Physiology 58.8 (2012): 1042-1049.
Gupta, Shaan; et al. "Fecal microbiota transplantation: in perspective." Therapeutic advances in gastroenterology 9.2 (2016): 229-239.
Heidari, R., et al. "Hydrolysis of organophosphorus insecticides by in vitro modified carboxylesterase E3 from Lucilia cuprina." Insect biochemistry and molecular biology 34.4 (2004): 353-363.
Heidari, Rama, et al. "Hydrolysis of pyrethroids by carboxylesterases from Lucilia cuprina and *Drosophila melanogaster* with active sites modified by in vitro mutagenesis." Insect biochemistry and molecular biology 35.6 (2005): 597-609.
Hesketh, H., et al. "Extending standard testing period in honeybees to predict lifespan impacts of pesticides and heavy metals using dynamic energy budget modelling." Scientific reports 6.1 (2016): 1-12.
Hladik, Michelle L.; et al. "Methods of Analysis, Determination of Pyrethroid Insecticides in Water and Sediment Using Gas Chromatography/mass Spectrometry." (2009).
Hroncova, Zuzana, et al. "Variation in honey bee gut microbial diversity affected by ontogenetic stage, age and geographic location." PloS one 10.3 (2015): e0118707.
Hurwitz, Ivy, et al. "Paratransgenic control of vector borne diseases." International Journal of Biological Sciences 7.9 (2011): 1334.
Hussain, Sarfraz, et al. "Bacterial biodegradation of neonicotinoid pesticides in soil and water systems." FEMS microbiology letters 363.23 (2016).
Ihara, Makoto, et al. "Modes of action, resistance and toxicity of insecticides targeting nicotinic acetylcholine receptors." Current medicinal chemistry 24.27 (2017): 2925-2934.
Itoh, Hideomi, et al. "Evidence of environmental and vertical transmission of Burkholderia symbionts in the oriental chinch bug, *Cavelerius saccharivorus* (Heteroptera: Blissidae)." Applied and environmental microbiology 80.19 (2014): 5974-5983.
Iyer, Rupa; et al. "A comparison of organophosphate degradation genes and bioremediation applications." Environmental microbiology reports 5.6 (2013): 787-798.
Jia, Hui-Ru, et al. "No effect of Bt Cry1Ie toxin on bacterial diversity in the midgut of the Chinese honey bees, *Apis cerana cerana* (Hymenoptera, Apidae)." Scientific reports 7.1 (2017): 1-10.
Johnson, Reed M., et al. "Mediation of pyrethroid insecticide toxicity to honey bees (*Hymenoptera: apidae*) by cytochrome P450 monooxygenases." Journal of economic entomology 99.4 (2006): 1046-1050.
Johnson, Reed M., et al. "Pesticides and honey bee toxicity—USA." Apidologie 41.3 (2010): 312-331.
Kikuchi, Yoshitomo, et al. "Symbiont-mediated insecticide resistance." Proceedings of the National Academy of Sciences 109.22 (2012): 8618-8622.
Klein, Alexandra-Maria; et al. "Fruit set of highland coffee increases with the diversity of pollinating bees." Proceedings of the Royal Society of London. Series B: Biological Sciences 270.1518 (2003): 955-961.
Klein, Simon, et al. "Why bees are so vulnerable to environmental stressors." Trends in ecology & evolution 32.4 (2017): 268-278.
Kovach, Michael E., et al. "Four new derivatives of the broad-host-range cloning vector pBBR1MCS, carrying different antibiotic-resistance cassettes." Gene 166.1 (1995): 175-176.
Kristich, Christopher J.; et al. "Development of a method for markerless genetic exchange in Enterococcus faecalis and its use in construction of a srtA mutant." Applied and environmental microbiology 71.10 (2005): 5837-5849.
Kwong, Waldan K.; et al. "Cultivation and characterization of the gut symbionts of honey bees and bumble bees: description of *Snodgrassella alvi* gen. nov., sp. nov., a member of the family Neisseriaceae of the Betaproteobacteria, and *Gilliamella apicola* gen. nov., sp. nov., a member of Orbaceae fam. nov., Orbales ord. nov., a sister taxon to the order 'Enterobacteriales' of the Gammaproteobacteria." International journal of systematic and evolutionary microbiology 63.6 (2013): 2008-2018.
Kwong, Waldan K., et al. "Genomics and host specialization of honey bee and bumble bee gut symbionts." Proceedings of the National Academy of Sciences 111.31 (2014): 11509-11514.
Kwong, Waldan K.; et al. "Gut microbial communities of social bees." Nature Reviews Microbiology 14.6 (2016): 374-384.
Kwong, Waldan K.; et al. "Immune system stimulation by the native gut microbiota of honey bees." Royal Society open science 4.2 (2017): 170003.
Le Conte, Yves, et al. "Interactions between risk factors in honey bees." (2012).
Lee, Fredrick J., et al. "Saccharide breakdown and fermentation by the honey bee gut microbiome." Environmental microbiology 17.3 (2015): 796-815.

(56) References Cited

OTHER PUBLICATIONS

Li, Huizhen, et al. "Global occurrence of pyrethroid insecticides in sediment and the associated toxicological effects on benthic invertebrates: an overview." Journal of hazardous materials 324 (2017): 258-271.
Li, Yongqiang, et al. "Bacterial expression and kinetic analysis of carboxylesterase 001D from Helicoverpa armigera." International journal of molecular sciences 17.4 (2016): 493.
Liu, Xiaolong, et al. "Directed evolution and secretory expression of a pyrethroid-hydrolyzing esterase with enhanced catalytic activity and thermostability." Microbial cell factories 16.1 (2017): 1-12.
Ludvigsen, Jane, et al. "Shifts in the midgut/pyloric microbiota composition within a honey bee apiary throughout a season." Microbes and environments (2015): ME15019.
Maddaloni, Massimo, et al. "Tolerance to the fungal pathogen Rhizoctonia solani AG4 of transgenic tobacco expressing the maize ribosome-inactivating protein b-32." Transgenic Research 6.6 (1997): 393-402.
Maddaloni, Massimo, et al. "Mucosal vaccine targeting improves onset of mucosal and systemic immunity to botulinum neurotoxin A." The Journal of Immunology 177.8 (2006): 5524-5532.
Maddaloni, M.; et al. "Paratransgenesis feasibility in the honeybee (*A pis mellifera*) using F ructobacillus fructosus commensal." Journal of applied microbiology 117.6 (2014): 1572-1584.
Maddaloni, Massimo, et al. "Milk-based nutraceutical for treating autoimmune arthritis via the stimulation of IL-10-and TGF-β-producing CD39+ regulatory T cells." PLoS One 10.1 (2015): e0117825.
Maddaloni, M.; et al. "Isolation of oxalotrophic bacteria associated with Varroa destructor mites." Letters in applied microbiology 61.5 (2015): 411-417.
Martinson, Vincent G., et al. "A simple and distinctive microbiota associated with honey bees and bumble bees." Molecular Ecology 20.3 (2011): 619-628.
Martinson, Vincent G.; et al. "Establishment of characteristic gut bacteria during development of the honeybee worker." Applied and environmental microbiology 78.8 (2012): 2830-2840.
Mattila, Heather R., et al. "Characterization of the active microbiotas associated with honey bees reveals healthier and broader communities when colonies are genetically diverse." PLoS One 7.3 (2012): e32962.
Meijer, Bartolomeus Joannes; et al. "Probiotics in the treatment of human inflammatory bowel diseases: update 2011." Journal of clinical gastroenterology 45 (2011): S139-S144.
Mohr, Kathrin I; et al. "Diversity and phylotype consistency of bacteria in the guts of three bee species (*Apoidea*) at an pilseed rape field." Environmental Microbiology 8.2 (2006): 258-272.
Mullin, Christopher A., et al. "High levels of miticides and agrochemicals in North American apiaries: implications for honey bee health." PloS one 5.3 (2010): e9754.
Nauen, Ralf, et al. "Efficacy of plant metabolites of imidacloprid against Myzus persicae and Aphis gossypii (Homoptera: Aphididae)." Pesticide Science 52.1 (1998): 53-57.
Weston, Donald P.; et al. "Use of engineered enzymes to identify organophosphate and pyrethroid-related toxicity in toxicity identification evaluations." Environmental Science & Technology 43.14 (2009): 5514-5520.
Wiest, Laure, et al. "Multi-residue analysis of 80 environmental contaminants in honeys, honeybees and pollens by one extraction procedure followed by liquid and gas chromatography coupled with mass spectrometric detection." Journal of Chromatography A 1218.34 (2011): 5743-5756.
Wu, Ke; et al. "The glutathione-S-transferase, cytochrome P450 and carboxyl/cholinesterase gene superfamilies in predatory mite *Metaseiulus occidentalis*." PloS one 11.7 (2016): e0160009.
Wu, Pei C., et al. "Molecular cloning, purification, and biochemical characterization of a novel pyrethroid-hydrolyzing esterase from *Klebsiella* sp. strain ZD112." Journal of agricultural and food chemistry 54.3 (2006): 836-842.
Wu, Shuwen, et al. "Overexpressed esterases in a fenvalerate resistant strain of the cotton bollworm, *Helicoverpa armigera*." Insect Biochemistry and Molecular Biology 41.1 (2011): 14-21.
Wu, Yi-Jie, et al. "Evaluation of efficacy and safety of Lactobacillus rhamnosus in children aged 4-48 months with atopic dermatitis: An 8-week, double-blind, randomized, placebo-controlled study." Journal of microbiology, Immunology and infection 50.5 (2017): 684-692.
Xi, Jinghui, et al. "Elevated expression of esterase and cytochrome P450 are related with lambda-cyhalothrin resistance and lead to cross resistance in Aphis glycines Matsumura." Pesticide biochemistry and physiology 118 (2015): 77-81.
Xie, J., et al. "Improving methyl parathion hydrolase to enhance its chlorpyrifos-hydrolysing efficiency." Letters in applied microbiology 58.1 (2014): 53-59.
Yang, Xinghong, et al. "Deletion of znuA virulence factor attenuates Brucella abortus and confers protection against wild-type challenge." Infection and immunity 74.7 (2006): 3874-3879.
Zhao, Ruihua, et al. "Cloning and heterologous expression of insecticidal-protein-encoding genes from Photorhabdus luminescens TT01 in Enterobacter cloacae for termite control." Applied and Environmental Microbiology 74.23 (2008): 7219-7226.
Zhu, Yu-Cheng; et al. "Detection of single-base substitution in an esterase gene and its linkage to malathion resistance in the parasitoid Anisopteromalus calandrae (Hymenoptera: Pteromalidae)." Pesticide Science 55.4 (1999): 398-404.
Zhu, Yu Cheng, et al. "Synergistic toxicity and physiological impact of imidacloprid alone and binary mixtures with seven representative pesticides on honey bee (*Apis mellifera*)." PloS one 12.5 (2017): e0176837.
Zuo, Zhenqiang, et al. "Engineering Pseudomonas putida KT2440 for simultaneous degradation of organophosphates and pyrethroids and its application in bioremediation of soil." Biodegradation 26.3 (2015): 223-233.
Cox-Foster, Diana L., et al. "A metagenomic survey of microbes in honey bee colony collapse disorder." Science 318.5848 (2007): 283-287.
Al-Ghamdi, Ahmad, et al. "Effect of gut bacterial isolates from Apis mellifera jemenitica on Paenibacillus larvae infected bee larvae." Saudi journal of biological sciences 25.2 (2018): 383-387.
Arredondo, Daniela, et al. "Lactobacillus kunkeei strains decreased the infection by honey bee pathogens Paenibacillus larvae and Nosema ceranae." Beneficial microbes 9.2 (2018): 279-290.
Audisio, M.; et al. "Lactobacillus johnsonii CRL 1647, isolated from *Apis mellifera* L. bee-gut, exhibited a beneficial effect on honeybee colonies." Beneficial Microbes 2.1 (2011): 29-34.
Zhang, Ruifu, et al. "Cloning of the organophosphorus pesticide hydrolase gene clusters of seven degradative bacteria isolated from a methyl parathion contaminated site and evidence of their horizontal gene transfer." Biodegradation 17.5 (2006): 465-472.
Eibes, G., et al. "Enzymatic technologies for remediation of hydrophobic organic pollutants in soil." Applied microbiology and biotechnology 99.21 (2015): 8815-8829.
Evans, Jay D.; et al. "Genetics and physiology of Varroa mites." Current opinion in insect science 26 (2018): 130-135.
Kadisch, Marvin, et al. "Maximizing the stability of metabolic engineering-derived whole-cell biocatalysts." Biotechnology journal 12.8 (2017): 1600170.
Leonard, Sean P., et al. "Genetic engineering of bee gut microbiome bacteria with a toolkit for modular assembly of broad-host-range plasmids." ACS synthetic biology 7.5 (2018): 1279-1290.
Martin, Stephen J. "Acaricide (pyrethroid) resistance in Varroa destructor." Bee World 85.4 (2004): 67-69.
Polakovic, Milan, et al. "Progress in biocatalysis with immobilized viable whole cells: systems development, reaction engineering and applications." Biotechnology letters 39.5 (2017): 667-683.
Rayu, Smriti; et al. "Emerging technologies in bioremediation: constraints and opportunities." Biodegradation 23.6 (2012): 917-926.
Sabate, Daniela Constanza, et al. "Beneficial effects of *Bacillus subtilis* subsp. subtilis Mori2, a honey-associated strain, on honeybee colony performance." Probiotics and Antimicrobial Proteins 4.1 (2012): 39-46.

(56) References Cited

OTHER PUBLICATIONS

Sanchez-Bayo; et al. "Pesticide residues and bees—a risk assessment." PloS one 9.4 (2014): e94482.

Spök, Armin; et al. "Status of microbial based cleaning products in statutory regulations and ecolabelling in Europe, the USA, and Canada." Food and Chemical Toxicology 116 (2018): 10-19.

Stadlmair, Lara F., et al. "Enzymes in removal of pharmaceuticals from wastewater: A critical review of challenges, applications and screening methods for their selection." Chemosphere 205 (2018): 649-661.

Tang, Wangxin, et al. "Pyrethroid pesticide residues in the global environment: an overview." Chemosphere 191 (2018): 990-1007.

Soderlund, David M., et al. "Mechanisms of pyrethroid neurotoxicity: implications for cumulative risk assessment." Toxicology 171.1 (2002): 3-59.

Hotel, Sheraton Suites Old Town Alexandria, and Virginia Alexandria. "Report on the National Stakeholders Conference on Honey Bee Health." (2012).

International Search Report and Written Opinion for PCT/US19/44945 dated Oct. 29, 2019.

Christopher, K et al. Apr. 29, 2019. Delivery of ionic molecules to anterior chamber by pontophoretic contact lenses. European Journal of Pharmaceutics and Biopharmaceutics 140 (2019) 40-49; entire document.

Biswas, Indranil; et al. "Shuttle expression plasmids for genetic studies in *Streptococcus mutans*." Microbiology (Reading, England) 154.0 8 (2008): 2275.

Bloch, Guy. "The social clock of the honeybee." Journal of biological rhythms 25.5 (2010): 307-317.

Bosma, Tjibbe, et al. "Novel surface display system for proteins on non-genetically modified gram-positive bacteria." Applied and environmental microbiology 72.1 (2006): 880-889.

Buffie, Charlie G., et al. "Precision microbiome reconstitution restores bile acid mediated resistance to Clostridium difficile." Nature 517.7533 (2015): 205-208.

Calderone, Nicholas W. "Insect pollinated crops, insect pollinators and US agriculture: trend analysis of aggregate data for the period 1992-2009." PloS one 7.5 (2012): e37235.

Campbell, Joshua W., et al. "An evaluation of the honey bee (*Hymenoptera: apidae*) safety profile of a new systemic Insecticide, flupyradifurone, under field conditions in Florida." Journal of economic entomology 109.5 (2016): 1967-1972.

Cheng, Daifeng, et al. "Gut symbiont enhances insecticide resistance in a significant pest, the oriental fruit fly *Bactrocera dorsalis* (Hendel)." Microbiome 5.1 (2017): 1-12.

Alippi, Adriana M.; et al. "Inhibition of the growth of Paenibacillus larvae, the causal agent of American foulbrood of honeybees, by selected strains of aerobic spore-forming bacteria isolated from apiarian sources." Journal of Invertebrate pathology 91.3 (2006): 141-146.

Aljedani, Dalal Musleh; et al. "Effects of some insecticides on longevity of the foragers honey bee worker of local honey bee race *Apis mellifera jemenatica*." Electronic physician 8.1 (2016): 1843.

Anastassiades, Michelangelo, et al. "Fast and easy multiresidue method employing acetonitrile extraction/partitioning and "dispersive solid-phase extraction" for the determination of pesticide residues in produce." Journal of AOAC International 86.2 (2003): 412-431.

Anderson, Kirk E., et al. "Microbial ecology of the hive and pollination landscape: bacterial associates from floral nectar, the alimentary tract and stored food of honey bees (*Apis mellifera*)." PloS one 8.12 (2013): e83125.

Anderson, Kirk E., et al. "Hive-stored pollen of honey bees: many lines of evidence are consistent with pollen preservation, not nutrient conversion." Molecular ecology 23.23 (2014): 5904-5917.

Audisio, M. Carina; et al. "Bacteriocin from honeybee beebread *Enterococcus avium*, active against Listeria monocytogenes." Applied and Environmental Microbiology 71.6 (2005): 3373-3375.

Audisio, Marcela Carina. "Gram-positive bacteria with probiotic potential for the *Apis mellifera* L. honey bee: the experience in the northwest of Argentina." Probiotics and antimicrobial proteins 9.1 (2017): 22-31.

Benedict, M. Q.; et al. "High-level expression of the bacterial opd gene in *Drosophila melanogasten* improved inducible Insecticide resistance." Insect molecular biology 3.4 (1994): 247-252.

Berasategui, Aileen, et al. "Potential applications of insect symbionts in biotechnology." Applied microbiology and biotechnology 100.4 (2016): 1567-1577.

Birner-Gruenberger, Ruth, et al. "Functional fat body proteomics and gene targeting reveal in vivo functions of *Drosophila melanogaster* α-Esterase-7." Insect biochemistry and molecular biology 42.3 (2012): 220-229.

Christen, Verena, and Karl Fent. "Exposure of honey bees (*Apis mellifera*) to different classes of insecticides exhibit distinct molecular effect patterns at concentrations that mimic environmental contamination." Environmental pollution 226 (2017): 48-59.

Coppin, Chris W., et al. "Testing the evolvability of an insect carboxylesterase for the detoxification of synthetic pyrethroid insecticides." Insect biochemistry and molecular biology 42.5 (2012): 343-352.

Corby-Harris, Vanessa; et al. "The bacterial communities associated with honey bee (*Apis mellifera*) foragers." PloS one 9.4 (2014): e95056.

Corby-Harris, Vanessa, et al. "Origin and effect of Alpha 2.2 Acetobacteraceae in honey bee larvae and description of *Parasaccharibacter apium* gen. nov., sp. nov." Applied and environmental microbiology 80.24 (2014): 7460-7472.

Corby-Harris, Vanessa, et al. "*Parasaccharibacter apium*, gen. nov., sp. nov., improves honey bee (*Hymenoptera: apidae*) resistance to Nosema." Journal of economic entomology 109.2 (2016): 537-543.

Cornman, R. Scott, et al. "Pathogen webs in collapsing honey bee colonies." PLoS one 7.8 (2012): e43562.

Coutinho-Abreu, Iliano V.; et al. "Transgenesis and paratransgenesis to control insect-borne diseases: current status and future challenges." Parasitology international 59.1 (2010): 1-8.

Zhongli, Cui; et al. "Isolation of methyl parathion-degrading strain M6 and cloning of the methyl parathion hydrolase gene." Applied and environmental microbiology 67.10 (2001): 4922-4925.

Cycon, Mariusz; et al. "Pyrethroid-degrading microorganisms and their potential for the bioremediation of contaminated soils: a review." Frontiers in microbiology 7 (2016): 1463.

Dai, Ping-Li, et al. "Bt Cry1Ie toxin does not impact the survival and pollen consumption of Chinese honey bees, *Apis cerana cerana* (Hymenoptera, Apidae)." Journal of economic entomology 109.6 (2016): 2259-2263.

Dai, Pingli, et al. "Acute toxicity of five pesticides to Apis mellifera larvae reared in vitro." Pest management science 73.11 (2017): 2282-2286.

Daumann, Lena J., et al. "Promiscuity comes at a price: catalytic versatility vs efficiency in different metal ion derivatives of the potential bioremediator GpdQ." Biochimica et Biophysica Acta (BBA)-Proteins and Proteomics 1834.1 (2013): 425-432.

Desneux, Nicolas; et al. "The sublethal effects of pesticides on beneficial arthropods." Annu. Rev. Entomol. 52 (2007): 81-106.

Dewar, Alan M. "The adverse impact of the neonicotinoid seed treatment ban on crop protection in oilseed rape in the United Kingdom." Pest management science 73.7 (2017): 1305-1309.

Donnenberg, Michael S.; et al. "Construction of an eae deletion mutant of enteropathogenic *Escherichia coli* by using a positive-selection suicide vector." Infection and immunity 59.12 (1991): 4310-4317.

Douglas, Grace L.; et al. "Directed chromosomal integration and expression of the reporter gene gusA3 in Lactobacillus acidophilus NCFM." Applied and environmental microbiology 77.20 (2011): 7365-7371.

Esther, E., et al. "Detoxification mechanisms of honey bees (*Apis mellifera*) resulting in tolerance of dietary nicotine." Scientific reports 5.1 (2015): 1-11.

Durvasula, Ravi V., et al. "Prevention of insect-borne disease: an approach using transgenic symbiotic bacteria." Proceedings of the National Academy of Sciences 94.7 (1997): 3274-3278.

(56) References Cited

OTHER PUBLICATIONS

Eaton, David L. "Biotransformation enzyme polymorphism and pesticide susceptibility." Neurotoxicology 21.1 (2000): 101-112.
Engel, Philipp; et al. "Hidden diversity in honey bee gut symbionts detected by single-cell genomics." PLoS Genet 10.9 (2014): e1004596.
Fang, Weiguo, et al. "Development of transgenic fungi that kill human malaria parasites in mosquitoes." Science 331.6020 (2011): 1074-1077.
Faucon, Frederic, et al. "In the hunt for genomic markers of metabolic resistance to pyrethroids in the mosquito *Aedes aegypti*: An integrated next-generation sequencing approach." PLoS neglected tropical diseases 11.4 (2017): e0005526.
Feo, M. L.; et al. "Performance of gas chromatography/tandem mass spectrometry in the analysis of pyrethroid insecticides in environmental and food samples." Rapid Communications in Mass Spectrometry 25.7 (2011): 869-876.
Forsgren, Eva, et al. "Novel lactic acid bacteria inhibiting Paenibacillus larvae in honey bee larvae." Apidologie 41.1 (2010): 99-108.
Gallai, Nicola, et al. "Economic valuation of the vulnerability of world agriculture confronted with pollinator decline." Ecological economics 68.3 (2009): 810-821.
Gill, Richard J.; et al. "Combined pesticide exposure severely affects individual-and colony-level traits in bees." Nature 191.7422 (2012): 105-108.
Patel, Ashaben, et al. "Ocular drug delivery systems: An overview." World journal of pharmacology 2.2 (2013): 47.
Del Amo; et al. "Current and future ophthalmic drug delivery systems: a shift to the posterior segment." Drug discovery today 13.3-4 (2008): 135-143.
Hironaka, Kohei, et al. "Design and evaluation of a liposomal delivery system targeting the posterior segment of the eye." Journal of controlled release 136.3 (2009): 247-253.
Geroski, Dayle H; et al. "Transscleral drug delivery for posterior segment disease." Advanced drug delivery reviews 52.1 (2001): 37-48.
Patel, Samirkumar R., et al. "Targeted administration into the suprachoroidal space using a microneedle for drug delivery to the posterior segment of the eye." Investigative ophthalmology & visual science 53.8 (2012): 4433-4441.
Sasaki, Hitoshi, et al. "Retinal drug delivery using eyedrop preparations of poly-L-lysine-modified liposomes." European Journal of Pharmaceutics and Biopharmaceutics 83.3 (2013): 364-369.
Drummond, J. L.,; et al. "Physiological aging of an all-ceramic restorative material." Dental Materials 7.2 (1991): 133-137.
Szeto, Gregory Lee, et al. "Microfluidic squeezing for intracellular antigen loading in polyclonal B-cells as cellular vaccines." Scientific reports 5.1 (2015): 1-13.
Berdugo, M., et al. "Delivery of antisense oligonucleotide to the cornea by iontophoresis." Antisense and Nucleic Acid Drug Development 13.2 (2003): 107-114.
Ferreira, Alberto, et al. "Treatment frequency and dosing interval of ranibizumab and aflibercept for neovascular age-related macular degeneration in routine clinical practice in the USA." PloS one 10.7 (2015): e0133968.
Park, S. J., et al. "Intraocular pharmacokinetics of intravitreal vascular endothelial growth factor-Trap in a rabbit model." Eye 29.4 (2015): 561-568.
Eljarrat-Binstock; et al. "Iontophoresis: a non-invasive ocular drug delivery." Journal of Controlled Release 110.3 (2006): 479-489.
Nagarwal, Ramesh C; et al. "Chitosan coated sodium alginate-chitosan nanoparticles loaded with 5-FU for ocular delivery: In vitro characterization and in vivo study in rabbit eye." European Journal of Pharmaceutical Sciences 47.4 (2012): 678-685.
Loftsson, Thorsteinn; et al. "Cyclodextrin microparticles for drug delivery to the posterior segment of the eye: aqueous dexamethasone eye drops." Journal of pharmacy and pharmacology 59.5 (2007): 629-635.
Lee, Sang-Bumm, et al. "Drug delivery through the sclera: effects of thickness, hydration, and sustained release systems." Experimental eye research 78.3 (2004): 599-607.

Ambati, Jayakrishna; et al. "Transscleral drug delivery to the retina and choroid." Progress in retinal and eye research 21.2 (2002): 145-151.
Martinho, Nuno; et al. "Recent advances in drug delivery systems." Journal of biomaterials and nanobiotechnology 2.05 (2011): 510.
Gaudana, Ripal, et al. "Ocular drug delivery." The AAPS journal 12.3 (2010): 348-360.
Ogawa, Yudai, et al. "Organic transdermal iontophoresis patch with built-in biofuel cell." Advanced healthcare materials 4.4 (2015): 506-510.
Souied, Eric H., et al. "Non-invasive gene transfer by iontophoresis for therapy of an inherited retinal degeneration." Experimental eye research 87.3 (2008): 168-175.
Hao, Jinsong, et al. "Electrically assisted delivery of macromolecules into the corneal epithelium." Experimental eye research 89.6 (2009): 934-941.
Gibson, Daniel J; et al. "Dual-phase iontophoresis for the delivery of antisense oligonucleotides." nucleic acid therapeutics 27.4 (2017): 238-250.
Patni, Mayur, et al. "Transdermal iontophoretic delivery of timolol maleate." Brazilian Journal of Pharmaceutical Sciences 48.4 (2012): 819-827.
Lee, Hyunjae, et al. "Device-assisted transdermal drug delivery." Advanced drug delivery reviews 127 (2018): 35-45.
Münch, S.; et al. "Dermal and transdermal delivery of pharmaceutically relevant macromolecules." European Journal of Pharmaceutics and Biopharmaceutics 119 (2017): 235-242.
Margo, Curtis E; et al. "Fixation of whole eyes: the role of fixative osmolarity in the production of tissue artifact." Graefe's archive for clinical and experimental ophthalmology 233.6 (1995): 366-370.
Klyce, S. D. "Electrical profiles in the corneal epithelium." The Journal of physiology 226.2 (1972): 407-429.
Genina, Elina A; et al. "In-vitro study of methylene blue diffusion through the skin tissue." Lasers in Surgery: Advanced Characterization, Therapeutics, and Systems XII. vol. 4609. International Society for Optics and Photonics, 2002.
Meek, Keith M; et al. "Corneal structure and transparency." Progress in retinal and eye research 49 (2015): 1-16.
Kostyuk, Oksana, et al. "Transparency of the bovine corneal stroma at physiological hydration and its dependence on concentration of the ambient anion." The Journal of physiology 543.2 (2002): 633-642.
Elliott, Gerald F; et al. "Cornea, and the swelling of polyelectrolyte gels of biological interest." Reports on Progress in Physics 61.10 (1998): 1325.
Zhang, Wensheng; et al. "Model of transient drug diffusion across cornea." Journal of Controlled Release 99.2 (2004): 241-258.
Cruysberg, Lars PJ, et al. "In vitro human scleral permeability of fluorescein, dexamethasone-fluorescein, methotrexate-fluorescein and rhodamine 6G and the use of a coated coil as a new drug delivery system." Journal of ocular pharmacology and therapeutics 18.6 (2002): 559-569.
Jackson, Timothy L., et al. "Scleral hydraulic conductivity and macromolecular diffusion in patients with uveal effusion syndrome." Investigative ophthalmology & visual science 49.11 (2008): 5033-5040.
Balachandran, Ram K; et al. "Computer modeling of drug delivery to the posterior eye: effect of active transport and loss to choroidal blood flow." Pharmaceutical research 25.11 (2008): 2685-2696.
Zhu, Heng; et al. "Tear dynamics model." Current eye research 32.3 (2007): 177-197.
USDA "Cost per Colony to Pollinate Almonds up 1 Percent from Previous Year" (2016) Cost of Pollination.
Tabajdi, C. "Draft Report on Honeybee Health and the Challenges of the Beekeeping Sector." (2011).
Alberoni, Daniele, et al. "Beneficial microorganisms for honey bees: problems and progresses." Applied microbiology and biotechnology 100.22 (2016): 9469-9482.
Alder, Lutz, et al. "Residue analysis of 500 high priority pesticides: better by GC-MS or LC-MS/MS?." Mass spectrometry reviews 25.6 (2006): 838-865.

* cited by examiner

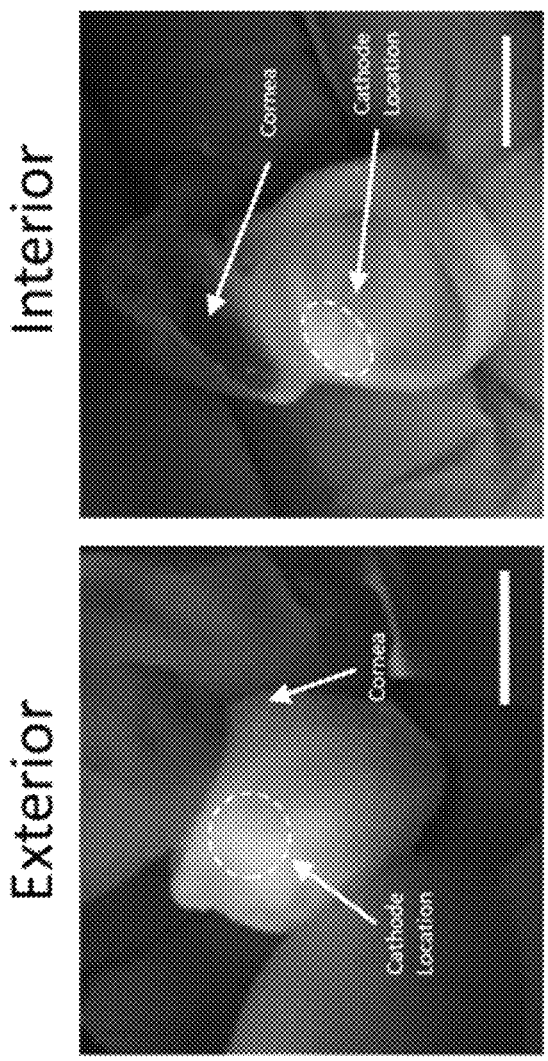
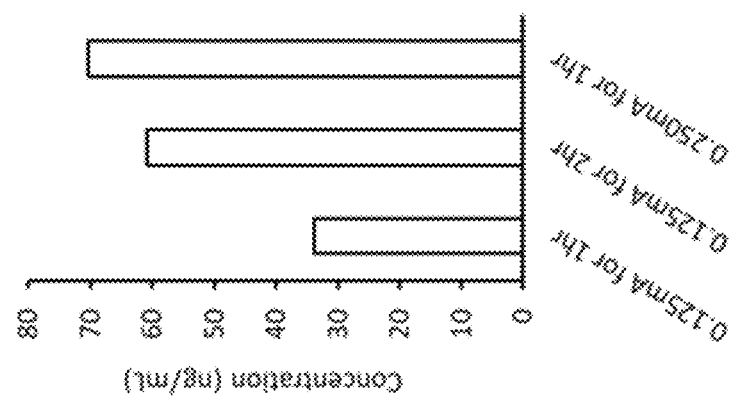
FIG. 11A
FIG. 11B
FIG. 11C

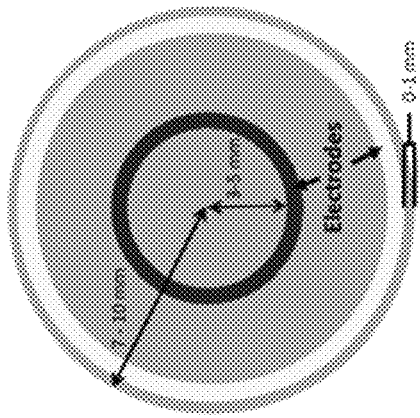
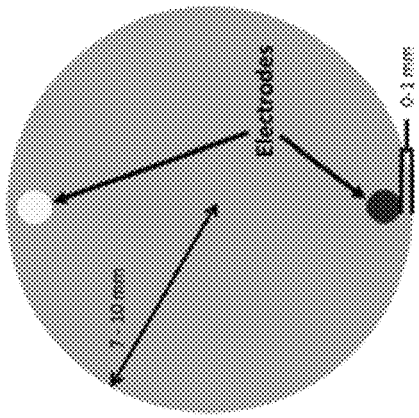
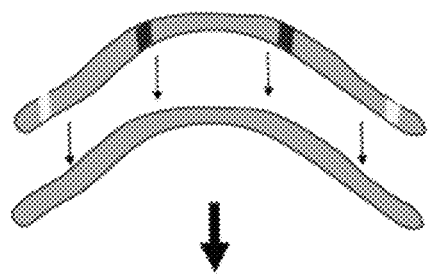
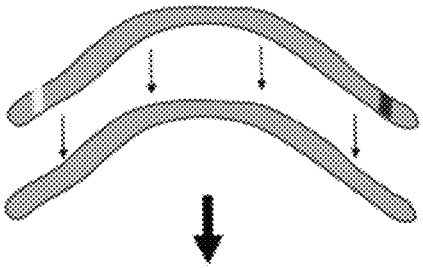
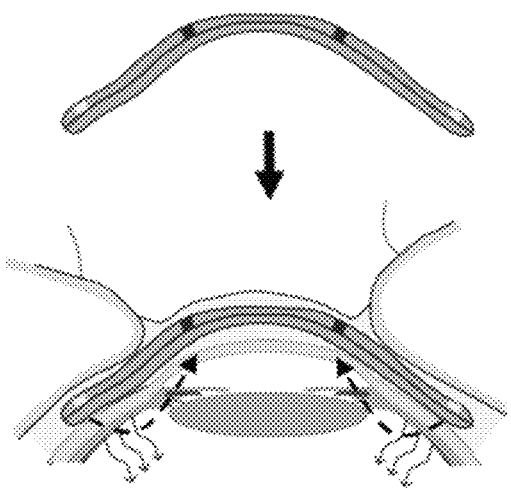
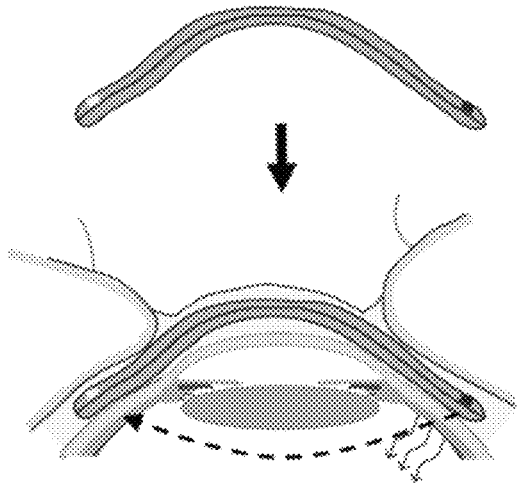
FIG. 14A
FIG. 14B

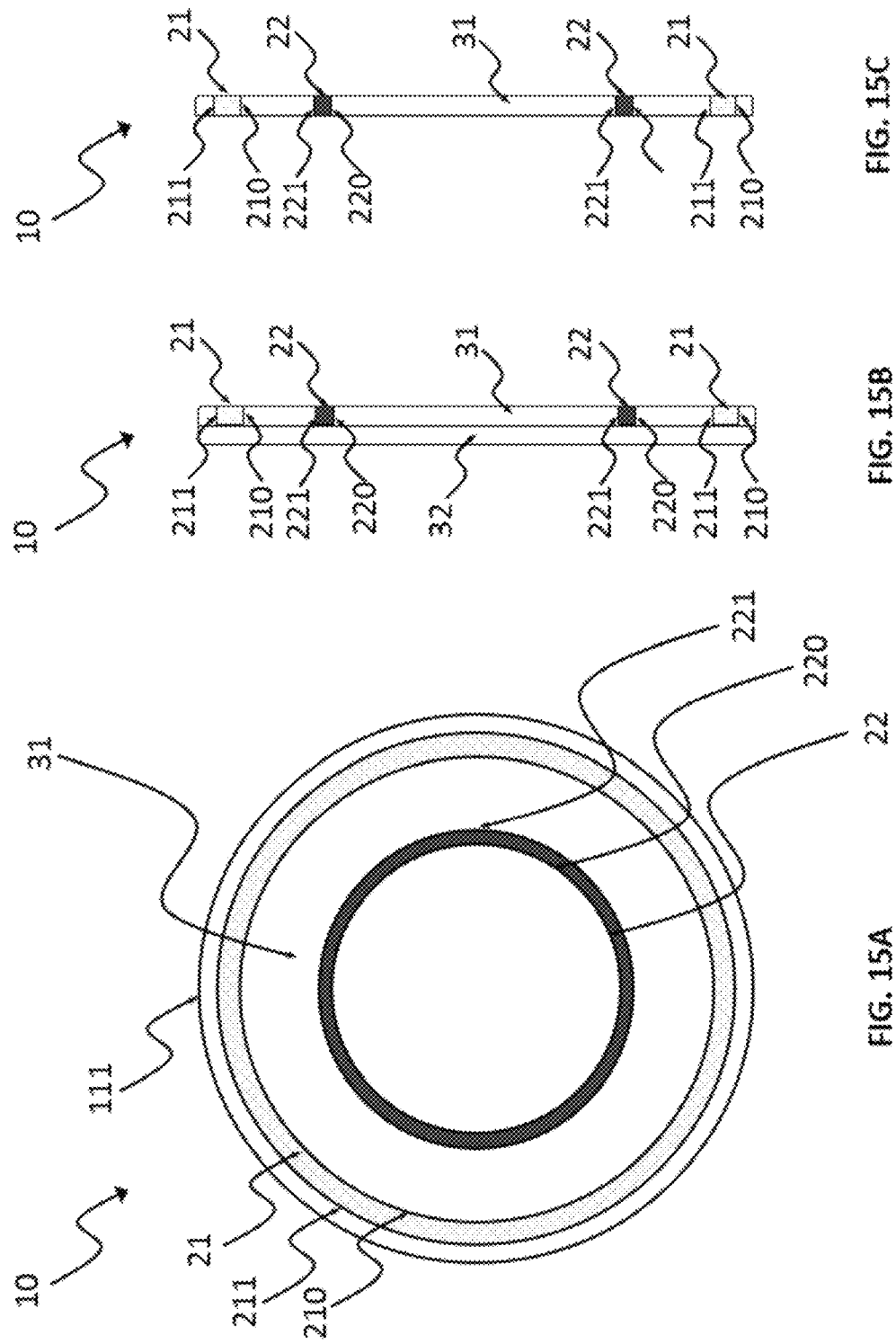

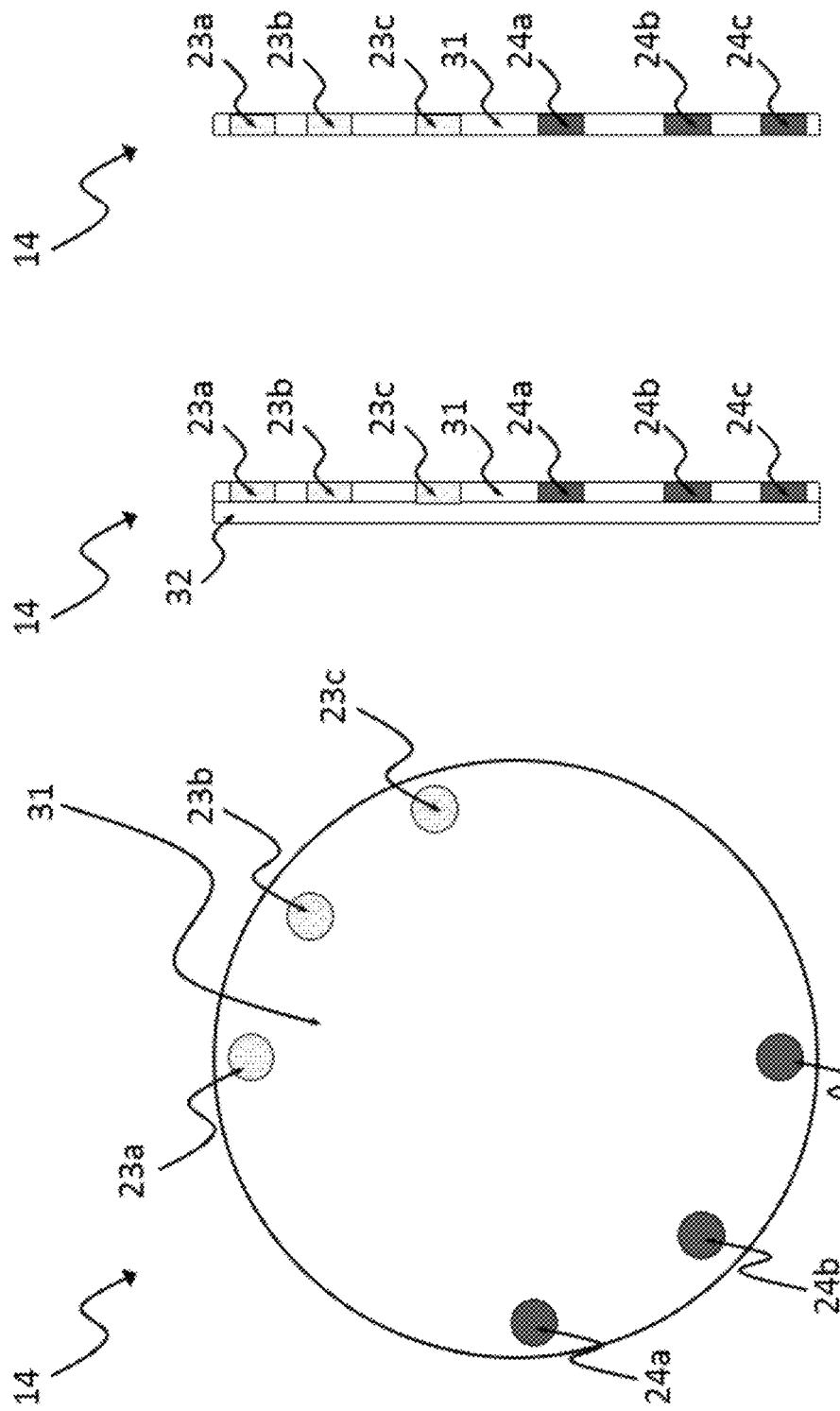

$2AgCl + 2e^- \rightarrow 2Ag + 2Cl^-$

Ag/AgCl (cathode)

$Zn \rightarrow Zn^{2+} + 2e^-$

Zinc (anode)

METHODS AND COMPOSITIONS FOR IONTOPHORETIC DRUG DELIVERY TO THE EYE

CROSS-REFERENCE TO RELATED APPLICATIONS

This application is the 35 U.S.C. § 371 national stage application of PCT Application No. PCT/US2019/044945, filed Aug. 2, 2019, where the PCT claims priority to, and the benefit of, U.S. provisional application entitled "METHODS AND COMPOSITIONS FOR IONTOPHORETIC DRUG DELIVERY TO THE EYE" having Ser. No. 62/713,990, filed Aug. 2, 2018, both of which are herein incorporated by reference in their entireties.

BACKGROUND

Ophthalmic drugs are most commonly delivered via eye drops in spite of significant drawbacks. Although nearly 90% of the current market for non-invasive ocular drugs are in eye drop form these offer a very low bioavailability (e.g., see Ref. 1). The inefficient drug uptake requires multiple applications of the eye drops a day and still cannot be used to treat retinal diseases (e.g., see Ref. 2). Although topical drugs are sufficient for a majority people afflicted by ocular diseases such as glaucoma, inflammation, bacterial or fungal infections, those that suffer from afflictions in the posterior eye segment need more invasive treatment such as direct injections (e.g., see Refs. 1-7). For example, macular edema or diabetic retinopathy can be treated using a vascular endothelial growth factor (VEGF) inhibitor to prevent the overexpression of VEGF which can also lead to increased cancer growth and metastasis (e.g., see Refs. 8-9). The inhibition of VEGF can also slow the progression of another common disease; age-related macular degeneration (AMD), which affects over 1-3% or people over the age of 50 every year (e.g., see Ref. 10). Once a patient has AMD, anti-VEGF treatment requires up to 8 injections to the posterior eye segment over the course of a year. This is a consequence of the drug being cleared from the vitreous within several days (e.g., see Ref. 11). Even though the injections allow for nearly instantaneous drug activity to the afflicted area and have a significant bioavailability, it is still accompanied by irritation and corneal toxicity, or in more serious cases, retinal detachment and endophthalmitis (e.g., see Ref. 12).

The deficiencies of administering an intravitreal injection has led to the exploration of alternative approaches to delivering drugs for posterior eye diseases. Among more appealing recent developments are microspheres or nanoparticles for increased retention and prolonged release, injectable and slow release devices, and sclera implants (e.g., see Refs. 13-15). All of these new technologies offer their own beneficial qualities, mainly aimed at the prolonged release without multiple follow up visits and treatments. However, these new technologies, such as microspheres and nanoparticles, still require direct injection into the vitreous or another form of surgical implantation. Additionally, each comes with a new set of complications such as difficulty of device insertion, high costs, low efficacy, and patient discomfort (e.g., see Refs. 7 and 16-18).

Delivery of drugs to the anterior region of is limited by passive diffusion through the endothelial and epithelial cell layers in the eye. These layers have low permeabilities and offer the greatest resistance in transporting drugs efficiently to the aqueous and the vitreous humor. Furthermore, when targeting the posterior region, the low permeabilities of the sclera and high uptake of the choroidal capillaries prevent rapid systemic delivery to the target regions. However, low drug permeability has been overcome in the past through iontophoresis, a process that incorporates an electric field that drives the migration of charged species to facilitate delivery of molecules to both aqueous and vitreous humor (e.g., see Ref. 19).

Recent technology that incorporates iontophoresis for targeted drug delivery to the eye utilizes large reservoirs with an embedded electrode. The counter electrode is then placed on the forehead or ear, resulting in a complex current pathway potentially resulting in large variability and a need for large voltage. A further shortcoming of conventional iontophoresis technology for the eye is that these devices are bulky and are associated with user discomfort stemming from the need to keep their eye open for the duration of the procedure, preventing the replenishment of the tear film (e.g., see Refs. 9 and 20-21). The approach is effective and necessary for the non-invasive delivery of much larger molecules such as RNAi or large growth factors (e.g., see Ref. 22).

Despite advances in devices and methods for delivery of therapeutic agents to the eye, currently available devices and methods are limited by a number of shortcomings. For example, several conventional methods, such as injection of microsphere or nanoparticles, are invasive and are associated with minimal patient comfort and potential for significant post-operative care. Although iontophoresis devices exist for delivery of therapeutic agents to the eye, conventional devices are bulky and associated with significant discomfort for the patient. Thus, there remains a need for devices and methods for the delivery of therapeutic agents that address the foregoing shortcomings, e.g., a need for compact, self-contained devices associated with minimal patient discomfort and capable of delivery of therapeutic agents to the anterior, posterior, or both regions of the eye. These needs and other needs are satisfied by the present disclosure.

SUMMARY

In accordance with the purpose(s) of the present disclosure, as embodied and broadly described herein, the disclosure, in one aspect, relates to ionophoretic ocular delivery devices for delivery of a therapeutic agent(s) to the eye. In some aspects, the disclosed ionophoretic ocular delivery device is configured for delivery of a therapeutic agent to the anterior portion of the eye. In various aspects, the present disclosure provides methods for treatment of an ophthalmological disorder, disease, or clinical condition by delivering a therapeutic agent(s) to the eye using a disclosed ionophoretic ocular delivery device. The ophthalmological disorder, disease or clinical condition includes, but is not limited to glaucoma, ocular hypertension, inflammation, including intraocular inflammation, keratitis, dry eye, uveitis, ophthalmological bacterial or fungal infections, macular edema, including cystoid macular edema, macular degeneration, blurred vision, herpetic conjunctivitis, blepharitis, retinal or choroidal neovascularization, other proliferative eye diseases, and/or diabetic retinopathy Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 3C shows representative photographic images obtained from one set of cadaver rabbit eyes after conclusion of Nile Blue A dye delivery from deionized (DI) water lenses. Note: **: p-value<0.05; *: p-value<0.1; N=3; and scale bar: 10 mm.

FIG. 4A shows images of diffusion of Nile Blue A dye through the cornea delivered via free standing solution ("Solution Diffusion") or via contact lens loaded with Nile Blue A dye after 60 min. FIG. 4B shows images of corneas of regions near the anode component and cathode component after delivery at 0.25 mA for 30 minutes from Nile Blue A dye-loaded delivery device of the present disclosure that was soaked in deionized water. FIG. 4C shows images of corneas of regions near the anode component and cathode component after delivery at 0.25 mA for 60 minutes from Nile Blue A dye-loaded delivery device of the present disclosure that was soaked in HEPES. FIG. 4D shows images of corneas of regions near the anode component and cathode component after delivery at 0.25 mA for 60 minutes from Nile Blue A dye-loaded delivery device of the present disclosure that was soaked in a HEPES buffer solution. Arrows overlaid in the images indicate the direction of the diffusion profile from the front of the cornea to the interior of the eye. The indicated scale bar is: 200 μm.

FIG. 7A shows a model eye (cadaver rabbit eye) after delivery of Nile Blue A dye at high current for 30 minutes with a disclosed ionophoretic ocular delivery device. Anodic region (right half) had a Nile Blue A dye loaded disclosed ionophoretic ocular delivery device soaked in DI water or PBS and cathodic region (left half) was soaked in HEPES. The indicated scale bar is: 5 mm. FIG. 7B shows confocal micrographic images of a disclosed ionophoretic ocular delivery device with PBS and Nile Blue A dye at the anode component and HEPES at the cathode component delivered under high current for 30 minutes. FITC shows intact stroma and the indicated red channel illustrates Nile Blue A dye distribution after delivery from the drug loaded lens. The indicated scale bar is: 200 μm.

FIGS. 11A-11C show representative data for distribution of fluorescein in a posterior eye segment. Briefly, a disclosed ionophoretic ocular delivery device was used to deliver fluorescein to a model eye (cadaver rabbit eye). FIG. 11A is a graphical representation of the concentration of fluorescein in the vitreous humor after application of the indicated electric fields. Fluorescent images (FIGS. 11B and 11C) obtained using a Nikon D810 camera with blue light source and orange filter show the exhibits the presence of fluorescein throughout the tissue in the posterior eye segment at the region near the cathode. FIG. 11B shows a fluorescent image obtained of the exterior of the eye, and FIG. 11C shows a fluorescent image of interior of the eye after bisecting and opening.

FIGS. 14A-14B show representative configuration for electrodes arrangement and geometry for disclosed ionophoretic ocular delivery devices. Concentric (FIG. 14A) and spot electrode (FIG. 14B) designs comprising a two-layer system for each, such that the two-layers comprise a top lens component and a bottom lens component. The lenses with electrode can be placed on a drug loaded lens component of the disclosed ionophoretic ocular delivery device and then placed in the eye. The dashed lines indicate the primary route of the electric field while the other arrows indicate the path of drug transport.

FIGS. 15A-15C show representative views of a disclosed ionophoretic ocular delivery device. FIG. 15A shows a top view of a disclosed ionophoretic ocular delivery device 10 comprising an outer concentric electrode 21, an inner concentric electrode 22, and a top lens component 31. FIG. 15B shows a side cross-sectional view of a disclosed ionophoretic ocular delivery device 10 comprising an outer concentric electrode 21, an inner concentric electrode 22, a top lens component 31, and a bottom lens component 32. FIG. 15C shows a side cross-sectional view of a disclosed ionophoretic ocular delivery device 10 comprising an outer concentric electrode 21, an inner concentric electrode 22, and a top lens component 31.

FIG. 16A shows a top view of a disclosed ionophoretic ocular delivery device 11 comprising a first spot electrode 23, a second spot electrode 24, and a top lens component 31. FIG. 16B shows a side cross-sectional view of a disclosed ionophoretic ocular delivery device 10 comprising a first spot electrode 23, a second spot electrode 24, a top lens component 31, and a bottom lens component 32. FIG. 16C shows a side cross-sectional view of a disclosed ionophoretic ocular delivery device 10 comprising a first spot electrode 23, a second spot electrode 24, and a top lens component 31.

FIG. 17A shows a top view of a disclosed ionophoretic ocular delivery device 12 comprising a first spot electrode 23, a second spot electrode 24, as indicated by the dashed lines, located beneath a top lens component 31. FIG. 17B shows a side cross-sectional view of a disclosed ionophoretic ocular delivery device 10 comprising a first spot electrode 23, located within the top lens component 31, and a second spot electrode 24, located within a bottom lens component 32.

FIGS. 18A-18C show representative views of a disclosed ionophoretic ocular delivery device. FIG. 18A shows a top view of a disclosed ionophoretic ocular delivery device 14 comprising a plurality of first spot electrodes 23a-23c, a plurality of second spot electrodes 24a-24c, and a top lens component 31. FIG. 18B shows a side cross-sectional view of a disclosed ionophoretic ocular delivery device 10 comprising a plurality of first spot electrodes 23a-23c, a plurality of second spot electrodes 24a-24c, a top lens component 31, and a bottom lens component 32. FIG. 18C shows a side cross-sectional view of a disclosed ionophoretic ocular delivery device 10 comprising a plurality of first spot electrodes 23a-23c, a plurality of second spot electrodes 24a-24c, and a top lens component 31.

FIG. 19A shows a top view of a disclosed ionophoretic ocular delivery device 50 comprising a conductive component 71, a water-activated battery comprising a cathode component 61 and an anode component 62, and a top lens component 31. FIG. 19B shows a side cross-sectional view of a disclosed ionophoretic ocular delivery device 50 comprising a conductive component 71, a water-activated battery comprising a cathode component 61 and an anode component 62, a top lens component 31, and a bottom lens component 32. FIG. 19C shows a side cross-sectional view of a disclosed ionophoretic ocular delivery device 50 comprising a conductive component 71, a water-activated battery comprising a cathode component 61 and an anode component 62, and a top lens component 31.

FIG. 21A shows a top view of a disclosed ionophoretic ocular delivery device 51 comprising a conductive component 72, a water-activated battery comprising a cathode component 63 and an anode component 64, and a top lens component 31. FIG. 21B shows a side cross-sectional view of a disclosed ionophoretic ocular delivery device 51 comprising a conductive component 72, a water-activated battery comprising a cathode component 63 and an anode component 64, a top lens component 31, and a bottom lens component 32. FIG. 21C shows a side cross-sectional view of a disclosed ionophoretic ocular delivery device 51 comprising a conductive component 72, a water-activated battery comprising a cathode component 63 and an anode component 64, and a top lens component 31.

FIG. 22A shows a representative schematic depiction of a disclosed ionophoretic ocular delivery device as described in FIGS. 21A-21C that comprises a zinc-based anode component and a silver/silver chloride cathode component with a gold conductive component. FIG. 22A further shows the electrochemical reactions that occur at the cathode and anode. FIG. 22B shows a representative photographic image of a disclosed ionophoretic ocular delivery device as described in FIGS. 21A-21C.

Figure 1:
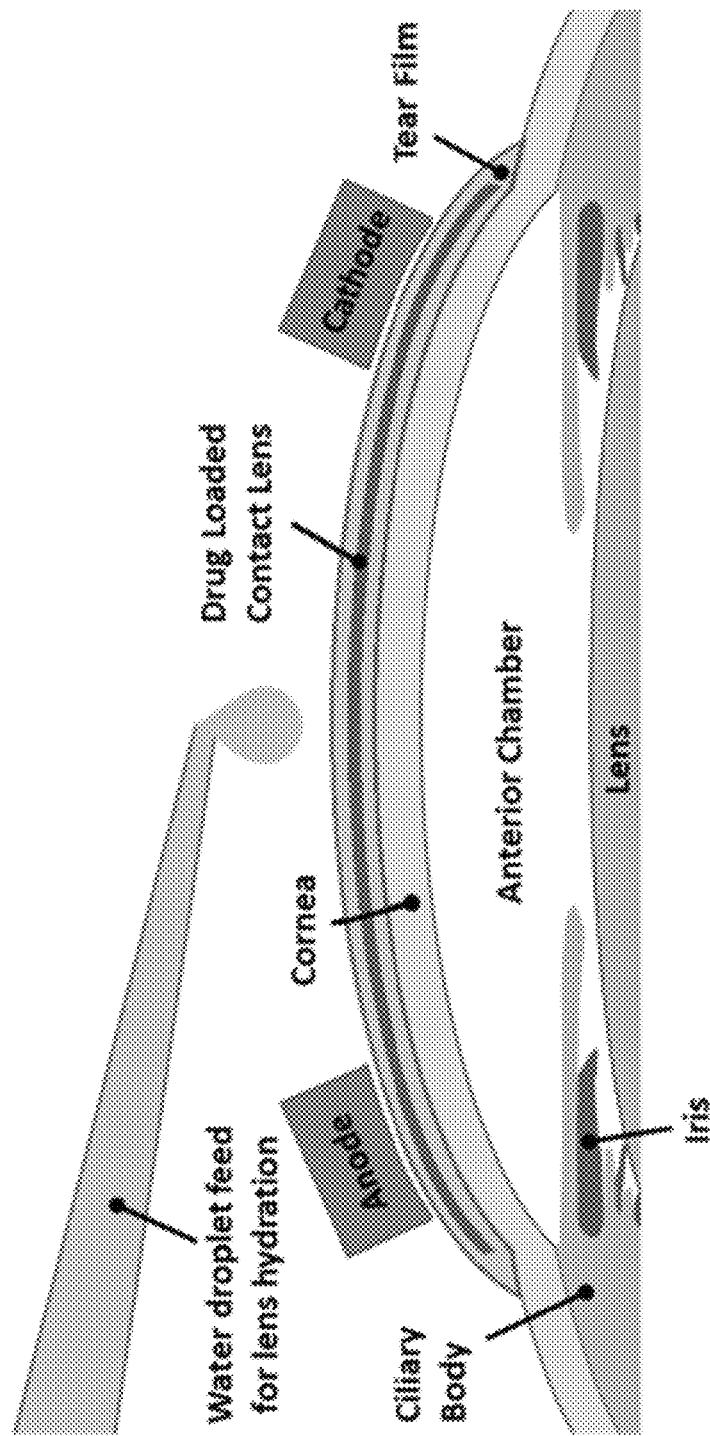
FIG. 1 shows a schematic view of an ex vivo arrangement of drug loaded lens and electrodes on a model eye (cadaver rabbit eye) for studies described herein. The electrodes were connected to a constant current power source with variable control. The electrodes rested on top of the lens but were not incorporated directly into the contact lens itself. The water droplet feed allows the continued hydration of the drug loaded contact lens.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Aspects of the present disclosure will employ, unless otherwise indicated, techniques of molecular biology, microbiology, organic chemistry, biochemistry, physiology, cell biology, blood vessel biology, and the like, which are within the skill of the art. Such techniques are explained fully in the literature.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a lens," "a therapeutic agent," or "an electrode," including, but not limited to, two or more such lens, therapeutic agents, or electrodes, including combinations of lens, therapeutic agents, or electrodes, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and about z' as well as the ranges of 'less than x', less than y', and 'less than z'. Likewise, the phrase about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not.

As used herein, "therapeutic agent" can refer to any substance, compound, molecule, and the like, which can be biologically active or otherwise can induce a pharmacologic, immunogenic, biologic and/or physiologic effect on a subject to which it is administered to by local and/or systemic action. A therapeutic agent can be a primary active agent, or in other words, the component(s) of a composition to which the whole or part of the effect of the composition is attributed. A therapeutic agent can be a secondary therapeutic agent, or in other words, the component(s) of a composition to which an additional part and/or other effect of the composition is attributed. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the *Physicians' Desk Reference* (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, "attached" can refer to covalent or non-covalent interaction between two or more molecules. Non-covalent interactions can include ionic bonds, electrostatic interactions, van der Walls forces, dipole-dipole interactions, dipole-induced-dipole interactions, London dispersion forces, hydrogen bonding, halogen bonding, electromagnetic interactions, π-π interactions, cation-π interactions, anion-π interactions, polar π-interactions, and hydrophobic effects.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as glaucoma, inflammation, ophthalmological bacterial or fungal infections, macular edema, and/or diabetic retinopathy. The effect can be therapeutic in terms of a partial or complete cure of a disease, condition, symptom or adverse effect attributed to the disease, disorder, or condition. The term "treatment" as used herein can include any treatment of glaucoma, inflammation, ophthalmological bacterial or fungal infections, macular edema, and/or diabetic retinopathy in a subject, particularly a human and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

As used herein, "dose," "unit dose," or "dosage" can refer to physically discrete units suitable for use in a subject, each unit containing a predetermined quantity of a disclosed compound and/or a pharmaceutical composition thereof calculated to produce the desired response or responses in association with its administration.

As used herein, "therapeutic" can refer to treating, healing, and/or ameliorating a disease, disorder, condition, or side effect, or to decreasing in the rate of advancement of a disease, disorder, condition, or side effect.

As used herein, "effective amount" can refer to the amount of a disclosed compound or pharmaceutical composition provided herein that is sufficient to effect beneficial or desired biological, emotional, medical, or clinical response of a cell, tissue, system, animal, or human. An effective amount can be administered in one or more administrations, applications, or dosages. The term can also include within its scope amounts effective to enhance or restore to substantially normal physiological function.

As used herein, the term "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. It is generally preferred that a maximum dose of the pharmacological agents of the disclosure (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

A response to a therapeutically effective dose of a disclosed compound and/or pharmaceutical composition, for example, can be measured by determining the physiological effects of the treatment or medication, such as the decrease or lack of disease symptoms following administration of the treatment or pharmacological agent. Other assays will be known to one of ordinary skill in the art and can be employed for measuring the level of the response. The amount of a treatment may be varied for example by increasing or decreasing the amount of a disclosed compound and/or pharmaceutical composition, by changing the disclosed compound and/or pharmaceutical composition administered, by changing the route of administration, by changing the dosage timing and so on. Dosage can vary, and can be administered in one or more dose administrations daily, for one or several days. Guidance can be found in the literature for appropriate dosages for given classes of pharmaceutical products.

As used herein, the term "prophylactically effective amount" refers to an amount effective for preventing onset or initiation of a disease or condition.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

The term "pharmaceutically acceptable" describes a material that is not biologically or otherwise undesirable, i.e., without causing an unacceptable level of undesirable biological effects or interacting in a deleterious manner.

The term "pharmaceutically acceptable salts", as used herein, means salts of the active principal agents which are prepared with acids or bases that are tolerated by a biological system or tolerated by a subject or tolerated by a biological system and tolerated by a subject when administered in a therapeutically effective amount. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include, but are not limited to; sodium, potassium, calcium, ammonium, organic amino, magnesium salt, lithium salt, strontium salt or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include, but are not limited to; those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like.

The term "pharmaceutically acceptable ester" refers to esters of compounds of the present disclosure which hydrolyze in vivo and include those that break down readily in the human body to leave the parent compound or a salt thereof. Examples of pharmaceutically acceptable, non-toxic esters of the present disclosure include C 1-to-C 6 alkyl esters and C 5-to-C 7 cycloalkyl esters, although C 1-to-C 4 alkyl esters are preferred. Esters of disclosed compounds can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, for example with methyl iodide, benzyl iodide, cyclopentyl iodide or alkyl triflate. They also can be prepared by reaction of the compound with an acid such as hydrochloric acid and an alcohol such as ethanol or methanol.

The term "pharmaceutically acceptable amide" refers to non-toxic amides of the present disclosure derived from ammonia, primary C 1-to-C 6 alkyl amines and secondary C 1-to-C 6 dialkyl amines. In the case of secondary amines, the amine can also be in the form of a 5- or 6-membered heterocycle containing one nitrogen atom. Amides derived from ammonia, C 1-to-C 3 alkyl primary amides and C 1-to-C 2 dialkyl secondary amides are preferred. Amides of disclosed compounds can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable amides are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, and piperidine. They also can be prepared by reaction of the compound with an acid such as sulfuric acid and an alkylcarboxylic acid such as acetic acid, or with acid and an arylcarboxylic acid such as benzoic acid under dehydrating conditions such as with molecular sieves added. The composition can contain a compound of the present disclosure in the form of a pharmaceutically acceptable prodrug.

The term "pharmaceutically acceptable prodrug" or "prodrug" represents those prodrugs of the compounds of the present disclosure which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the present disclosure can be rapidly transformed in vivo to a parent compound having a structure of a disclosed compound, for example, by hydrolysis in blood. A thorough discussion is provided in T. Higuchi and V. Stella, Pro-drugs as Novel Delivery Systems, V. 14 of the *A.C.S. Symposium Series*, and in Edward B. Roche, ed., Bioreversible Carriers in Drug Design, American Pharmaceutical Association and Pergamon Press (1987).

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

The term "contacting" as used herein refers to bringing a disclosed compound or pharmaceutical composition in proximity to a cell, a target protein, or other biological entity together in such a manner that the disclosed compound or pharmaceutical composition can affect the activity of the a cell, target protein, or other biological entity, either directly; i.e., by interacting with the cell, target protein, or other biological entity itself, or indirectly; i.e., by interacting with another molecule, co-factor, factor, or protein on which the activity of the cell, target protein, or other biological entity itself is dependent.

It is understood, that unless otherwise specified, temperatures referred to herein are based on atmospheric pressure (i.e. one atmosphere).

Described herein are ionophoretic devices for ocular delivery of therapeutic agents that have therapeutic or clinical utility. Other therapeutic agents, compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Unless otherwise specified, temperatures referred to herein are based on atmospheric pressure (i.e. one atmosphere).

Ionophoretic Ocular Delivery Devices

In various aspects, the present disclosure pertains to ionophoretic ocular delivery devices for the ionophoretic delivery of a therapeutic agent(s) to the eye.

Iontophoresis has been used more commonly for transdermal drug delivery. The device for transdermal iontophoresis (skin patch) includes both a cathode component and an anode component on the same patch (e.g., see Refs. 19 and 23-25). The anatomy and physiology of the human cornea is significantly different from that of the skin. While skin surface is relatively dry, the human eye contains a fluid tear film that could create a short circuit between the cathode component and the anode, minimizing any electric field penetration into the inner layers of the eye. Thus, a key question for the design of a drug delivery device using iontophoresis with the eye is whether the bypass current through the tear film eliminates or significantly reduces drug transport into the eye. A further consideration is whether the rate of gas production due to breakdown of water leads to unacceptable rate of bubble formation. Additionally, regarding transport through the anterior chamber, the cornea is a more sensitive tissue compared to skin so it is important to determine whether the electrochemical processes lead to unacceptable damage to the cornea.

For use in the posterior eye segment, the disclosed ionophoretic ocular delivery devices use a larger lens that extends past the cornea and configured such that the electrodes are located over the sclera. The application of the electric field will pass almost entirely through the sclera, choroid, retina, and vitreous, where the drug agent of interest can be deposited. The disclosed ionophoretic ocular delivery devices are configured such that the delivery of drug agents is targeted to the suprachoroidal space instead of the vitreous might also be a possibility for the application of this study.

In various aspects, the geometries of the electrodes associated with the disclosed ionophoretic ocular delivery devices are either concentric electrodes or single spot electrodes, both of which are highly effective configurations. In the examples herein below, the use of spot electrode configurations is demonstrated and showed efficacy in delivery through the cornea. Moreover, in the examples herein below, the data show delivery of therapeutics through the cornea and additionally to the posterior eye segment using iontophoresis in significant quantities. The disclosed ionophoretic ocular delivery devices overcome potential issues of corneal damage from reactions at the electrodes by placement of the electrodes over the sclera, which is a significantly more robust tissue than the corneal tissue.

In various aspects, the disclosed ionophoretic ocular delivery devices comprise two electrodes that are spatially separated and connected to a power supply. In some aspects, the power supply is external and apart from the lens component of the disclosed ionophoretic ocular delivery devices. Alternatively, in other aspects, the power supply is an integral component of the lens component of the disclosed ionophoretic ocular delivery devices, and is located on or within the lens component itself.

Referring now to FIGS. 15A-15C, which show representative views of a disclosed ionophoretic ocular delivery device. FIG. 15A shows a top view of a disclosed ionophoretic ocular delivery device 10 comprising an outer concentric electrode 21, an inner concentric electrode 22, and a top lens component 31, which can further comprise a bottom lens component, as shown in the side cross-sectional views of FIG. 15B. In alternative aspects, a top lens component 31 will not be associated with a bottom lens component, as shown in the side cross-sectional views of FIG. 15C. FIG. 15B shows a side cross-sectional view of a disclosed ionophoretic ocular delivery device 10 comprising an outer concentric electrode 21, an inner concentric electrode 22, a top lens component 31, and a bottom lens component 32. FIG. 15C shows a side cross-sectional view of a disclosed ionophoretic ocular delivery device 10 comprising an outer concentric electrode 21, an inner concentric electrode 22, and a top lens component 31.

In various aspects, the outer concentric electrode 21 has a diameter such that the outer edge of the outer concentric electrode 21 is near a top lens component outer edge 111 of the top lens component 10, and thereby locating it near an outer edge an eye cornea, e.g., within about 1 μm to about 1 mm of the outer edge of the eye cornea. This is particularly desirable if the therapeutic agent is targeted for delivery to the anterior portion of the eye. In other aspects, the outer concentric electrode 21 has a radius that is about R/2 to about R, where R is the radius of the top lens component 31. In some aspects, the outer concentric electrode 21 is flush with the outer edge of the top lens component 31, i.e., the outer edge of the outer concentric electrode 21 has a radius about the same as R. In other aspects, the outer concentric electrode 21 is not flush with, but near, the outer edge of the top lens component 31, i.e., the outer edge of the outer concentric electrode 21 has a radius that is about 90% to about 99% of R. In various aspects, the distance from the outer concentric electrode outer edge 211 to the outer concentric electrode inner edge 210 of the outer concentric electrode 21 is about 1 µm to about 5 mm.

In various aspects, the inner concentric electrode 22 has a diameter such that the outer edge of the inner concentric electrode 22 of the top lens component 10, and located interior to the outer concentric electrode 21. In a further aspect, the inner concentric electrode 22 has a radius that is about R/100 to about R/2, where R is the radius of the top lens component 31. In some aspects, the inner concentric electrode outer edge 221 is flush with the outer concentric electrode inner edge 210, i.e., the outer edge of the inner concentric electrode 22 has a radius about the same as the radius of the outer concentric electrode inner edge 210. In other aspects, the inner concentric electrode 22 is not flush with the outer concentric electrode inner edge 210. In still other aspects, inner concentric electrode 22 has an inner concentric electrode outer edge 221 radius that is about 80% to 99% of the radius of the outer concentric electrode inner edge 210. In various aspects, the distance from the inner concentric electrode outer edge 221 to the inner concentric electrode inner edge 220 of the inner concentric electrode 22 is about 1 µm to about 5 mm.

As shown in FIG. 15B, the outer concentric electrode 21 and the inner concentric electrode 22 have the same thickness as the thickness of the top lens component 10, and is located within the top and bottom surface of the top lens component 10. However, in other aspects, the outer concentric electrode 21 and the inner concentric electrode 22 can have a thickness that is less than the thickness of the top lens component 10. In such instances, the outer concentric electrode 21 and the inner concentric electrode 22 can be independently positioned flush with the top surface of the top lens component 10. In other such instances, the outer concentric electrode 21 and the inner concentric electrode 22 can be independently positioned flush with the bottom surface of the top lens component 10. In still other such instances, the outer concentric electrode 21 and the inner concentric electrode 22 can be independently positioned between the top and bottom surfaces of the top lens component 10.

As shown in FIG. 15C, the outer concentric electrode 21 and the inner concentric electrode 22 have the same thickness as the thickness of the top lens component 10, and is located within the top and bottom surface of the top lens component 10. However, in other aspects, the outer concentric electrode 21 and the inner concentric electrode 22 can have a thickness that is less than the thickness of the top lens component 10. In such instances, the outer concentric electrode 21 and the inner concentric electrode 22 can be independently positioned flush with the top surface of the top lens component 10. In other such instances, the outer concentric electrode 21 and the inner concentric electrode 22 can be independently positioned flush with the bottom surface of the top lens component 10. In still other such instances, the outer concentric electrode 21 and the inner concentric electrode 22 can be independently positioned between the top and bottom surfaces of the top lens component 10.

Figure 16C:
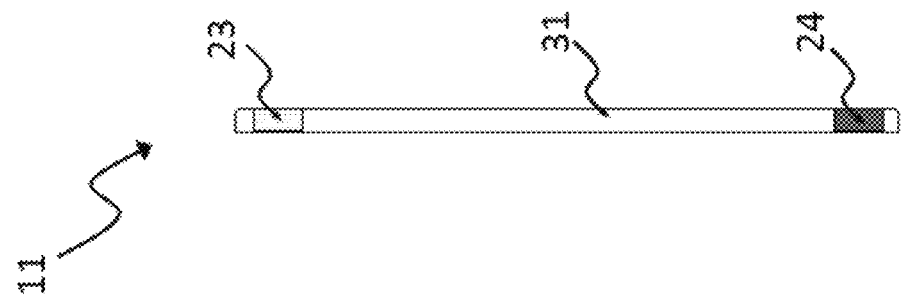
FIGS. 16A-16C show representative views of a disclosed ionophoretic ocular delivery device.
Figure 16B:
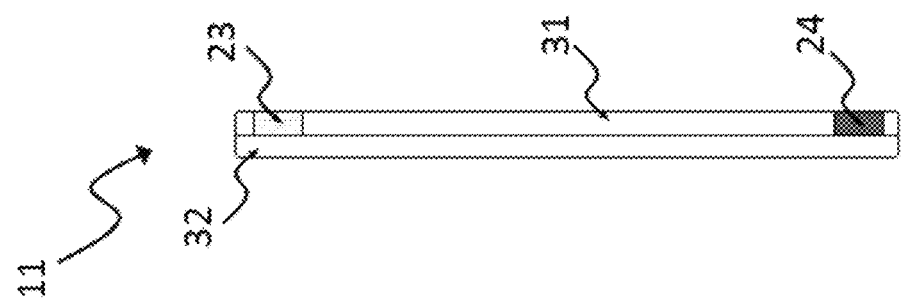
Figure 16A:
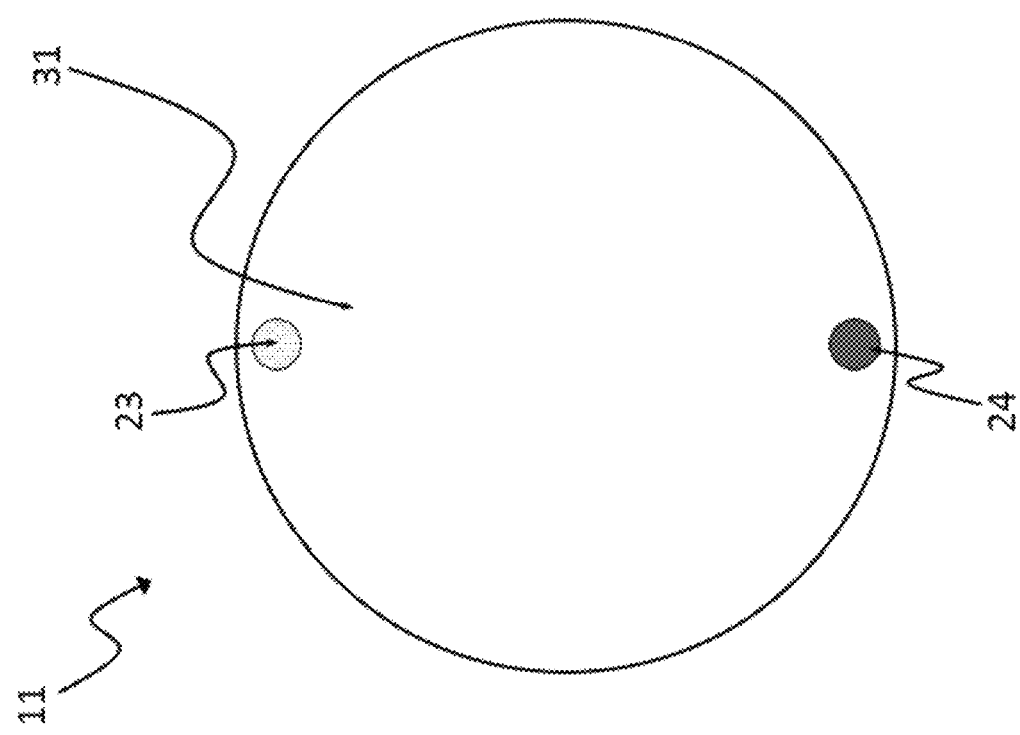

Referring now to FIGS. 16A-16C, which show representative views of a disclosed ionophoretic ocular delivery device. FIG. 16A shows a top view of a disclosed ionophoretic ocular delivery device 11 comprising a first spot electrode 23, a second spot electrode 24, and a top lens component 31, which can further comprise a bottom lens component, as shown in the side cross-sectional views of FIG. 16B. In alternative aspects, a top lens component 31 will not be associated with a bottom lens component, as shown in the side cross-sectional views of FIG. 16C. FIG. 16B shows a side cross-sectional view of a disclosed ionophoretic ocular delivery device 11 comprising a first spot electrode 23, a second spot electrode 24, a top lens component 31, and a bottom lens component 32. FIG. 16C shows a side cross-sectional view of a disclosed ionophoretic ocular delivery device 10 comprising a first spot electrode 23, a second spot electrode 24, and a top lens component 31.

In various aspects, the first spot electrode 23 and the second spot electrode 24 are located at a distance of about 0.6 R to about 1.0 R, where R is the radius of top lens component 31. In a further aspect, the first spot electrode 23 and the second spot electrode 24 are located at a distance of about 0.75 R to about 0.85 R, where R is the radius of top lens component 31. In some aspects, the first spot electrode 23 and the second spot electrode 24 are located such that they are offset from the outer edge of the top lens component 31 towards the center by about 0.05 R to about 0.2 R.

In various aspects, the orientation of the first spot electrode 23 and the second spot electrode 24 can be symmetrical, i.e., located opposite one another on the top lens component 31 as shown in FIG. 16A. In other aspects, the orientation of the first spot electrode 23 and the second spot electrode 24 can be asymmetrical.

In a further aspect, the diameter of the first spot electrode 23 and the second spot electrode 24 is independently about 0.05 R to about 0.4 R, where R is the radius of top lens component 31. In a still further aspect, the diameter of the first spot electrode 23 and the second spot electrode 24 is independently about 0.05 R to about 0.15 R, where R is the radius of top lens component 31. In a yet further aspect, the diameter of the first spot electrode 23 and the second spot electrode 24 is independently about 0.3 R to about 0.4 R, where R is the radius of top lens component 31.

Figure 17B:
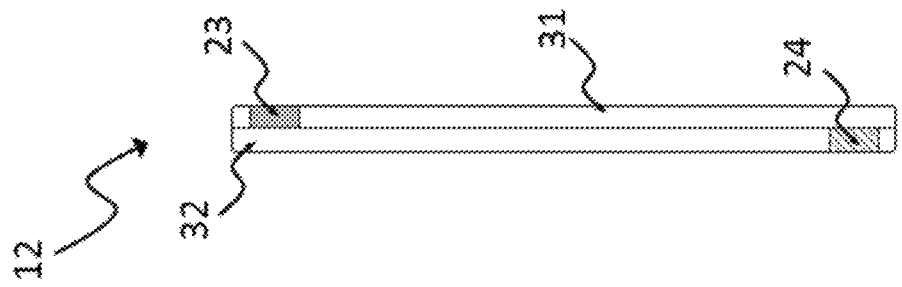
FIGS. 17A-17B show representative views of a disclosed ionophoretic ocular delivery device.
Figure 17A:
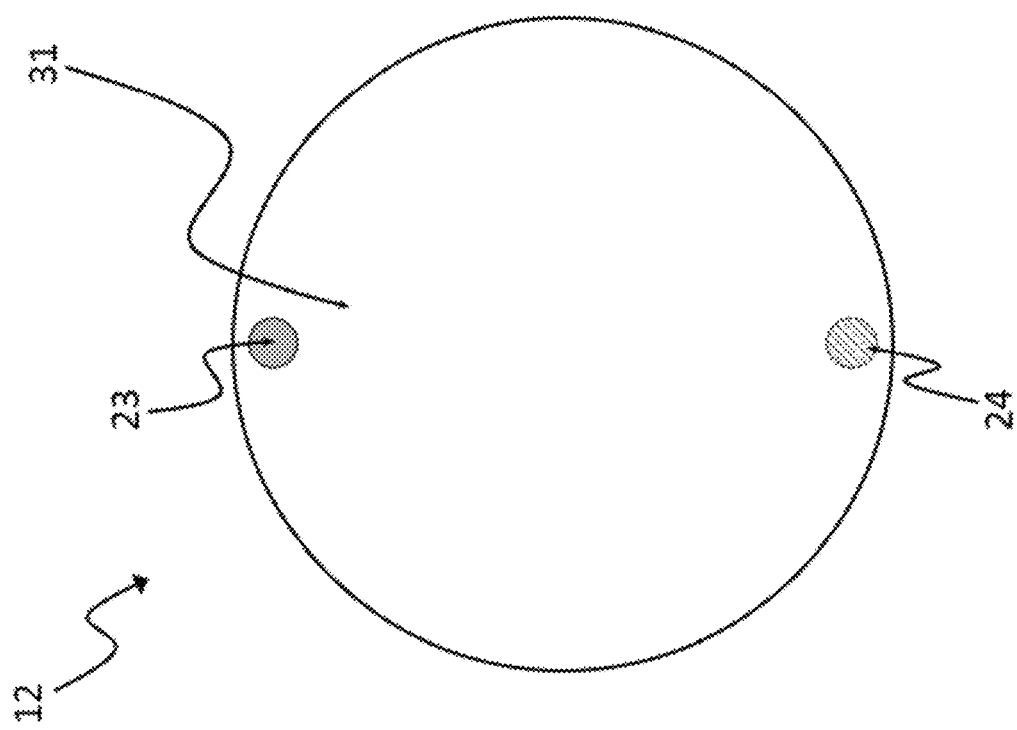

Referring now to FIGS. 17A-17B, which show representative views of a disclosed ionophoretic ocular delivery device. FIG. 17A shows a top view of a disclosed ionophoretic ocular delivery device 12 comprising a first spot electrode 23, a second spot electrode 24, as indicated by the dashed lines, located beneath a top lens component 31. FIG. 16B shows a side cross-sectional view of a disclosed ionophoretic ocular delivery device 10 comprising a first spot electrode 23, located within the top lens component 31, and a second spot electrode 24, located within a bottom lens component 32.

Referring now to FIGS. 18A-18C, which show representative views of a disclosed ionophoretic ocular delivery device. FIG. 18A shows a top view of a disclosed ionophoretic ocular delivery device 14 comprising a plurality of first spot electrodes 23a-23c, a plurality of second spot electrodes 24a-24c, and a top lens component 31, which can further comprise a bottom lens component, as shown in the side cross-sectional views of FIG. 18B. In alternative aspects, a top lens component 31 will not be associated with a bottom lens component, as shown in the side cross-sectional views of FIG. 18C. FIG. 18B shows a side cross-sectional view of a disclosed ionophoretic ocular delivery device 10 comprising a plurality of first spot electrodes 23a-23c, a plurality of second spot electrodes 24a-24c, a top lens component 31, and a bottom lens component 32. FIG. 18C shows a side cross-sectional view of a disclosed ionophoretic ocular delivery device 10 comprising a plurality of first spot electrodes 23a-23c, a plurality of second spot electrodes 24a-24c, and a top lens component 31.

In various aspects, the orientation of the plurality of first spot electrodes 23a-23c and the plurality of second spot electrodes 24a-24c can be symmetrical, e.g., located as shown in FIG. 18A, although one skilled in the art can appreciate that other symmetrical arrangements are possible. In a further aspect, a plurality of the first spot electrodes or the plurality of the second spot electrodes can be comprise about 2 to about 100 electrodes. In other aspects, the orientation the plurality of first spot electrodes 23a-23c and the plurality of second spot electrodes 24a-24c can be asymmetrical or even alternating with one another.

Figure 19C:
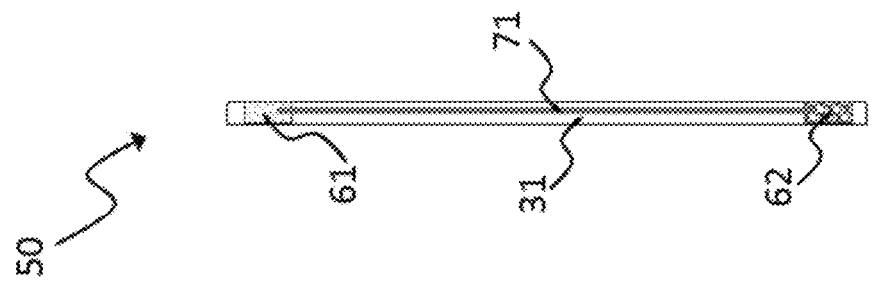
FIGS. 19A-19C show representative views of a disclosed ionophoretic ocular delivery device.
Figure 19B:
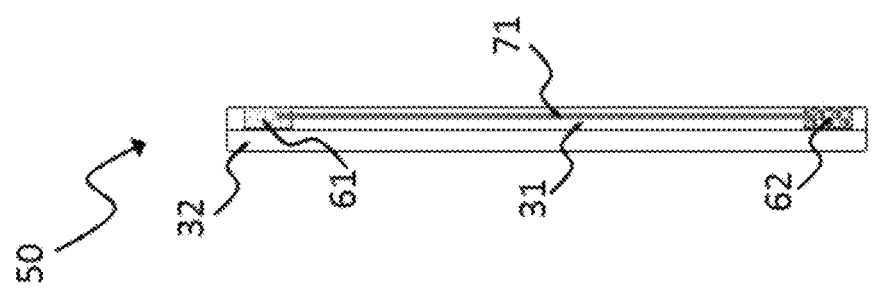
Figure 19A:
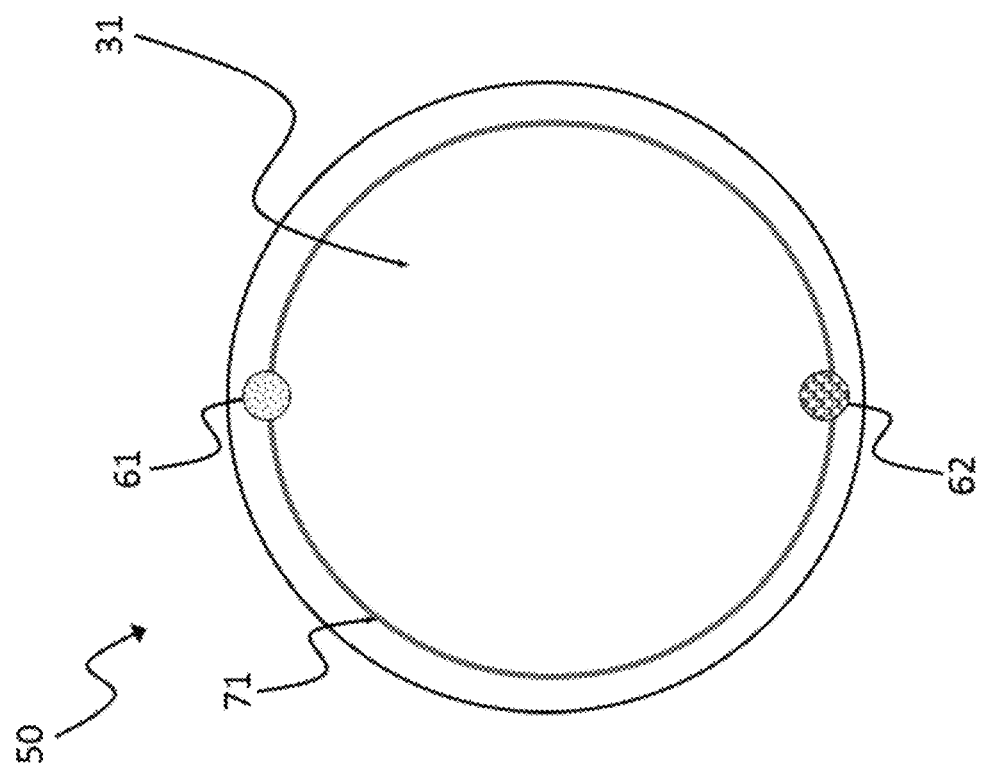
Figure 20:
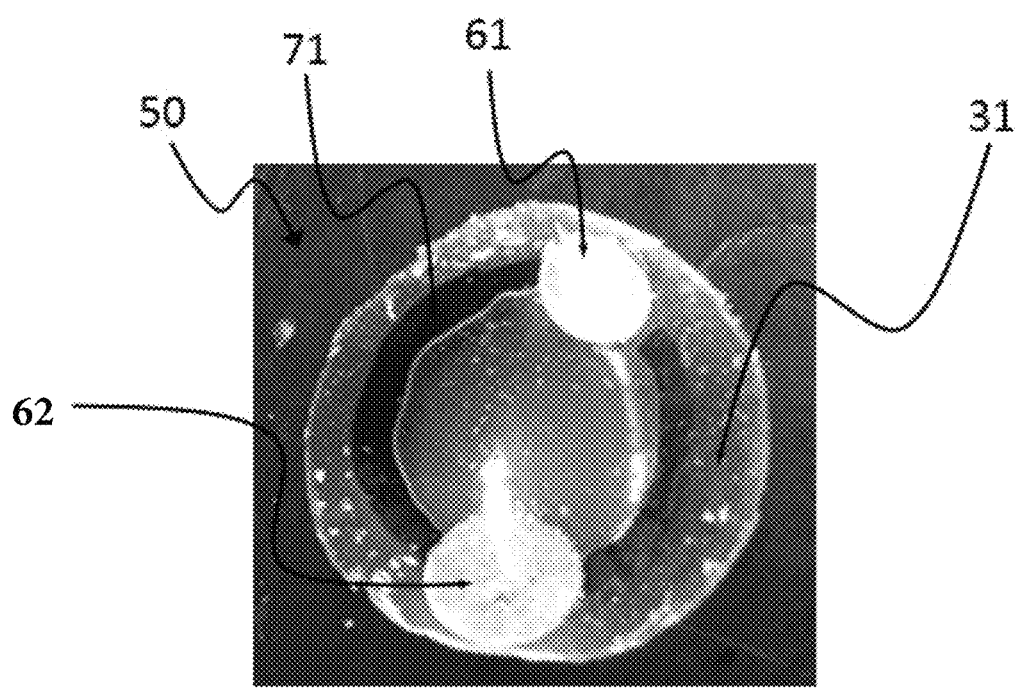
FIG. 20 shows a representative photographic image of a disclosed ionophoretic ocular delivery device as described in FIGS. 19A-19C.

Referring now to FIGS. 19A-19C, which show representative views of a disclosed ionophoretic ocular delivery device. FIG. 19A shows a top view of a disclosed ionophoretic ocular delivery device 50 comprising a conducting component 71, e.g. conductive metal or metal alloy, or alternatively, a conductive polymer layer, embedded or disposed on a top lens component 31, and such that the conducting component 71 is in communication with a water-activated battery comprising a cathode component 61 and an anode component 62. The top lens component 31 can further comprise a bottom lens component, as shown in the side cross-sectional views of FIG. 19B. In alternative aspects, a top lens component 31 will not be associated with a bottom lens component, as shown in the side cross-sectional views of FIG. 19C. FIG. 19B shows a side cross-sectional view of a disclosed ionophoretic ocular delivery device 50 comprising a conducting component 71, a water-activated battery comprising a cathode component 61 and an anode component 62, a top lens component 31, and a bottom lens component 32. FIG. 19C shows a side cross-sectional view of a disclosed ionophoretic ocular delivery device 50 comprising a conducting component 71, a water-activated battery comprising a cathode component 61 and an anode component 62, and a top lens component 31.

Figure 21C:
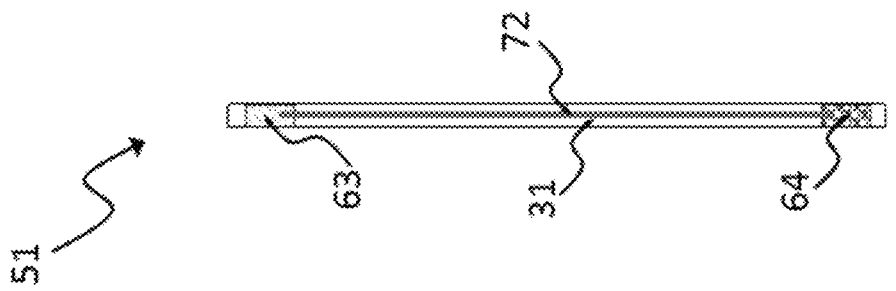
FIGS. 21A-21C show representative views of a disclosed ionophoretic ocular delivery device.
Figure 21B:
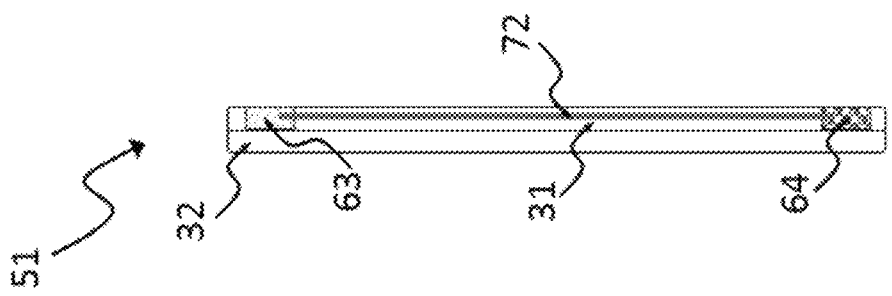
Figure 21A:
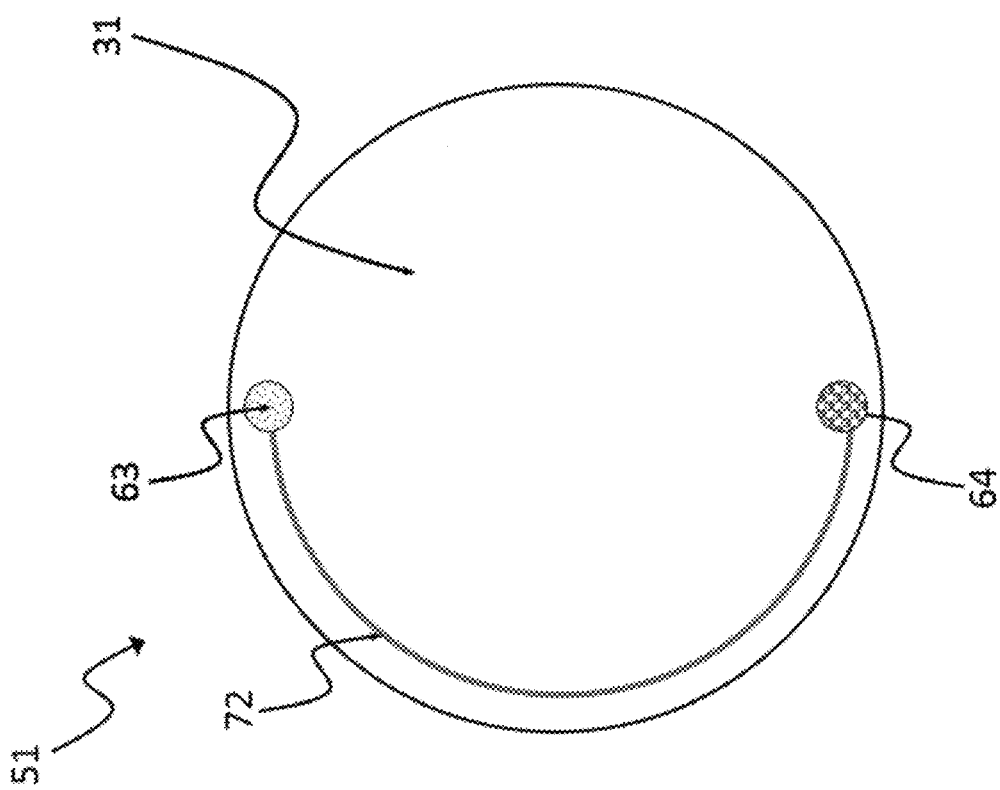
Figure 22A:
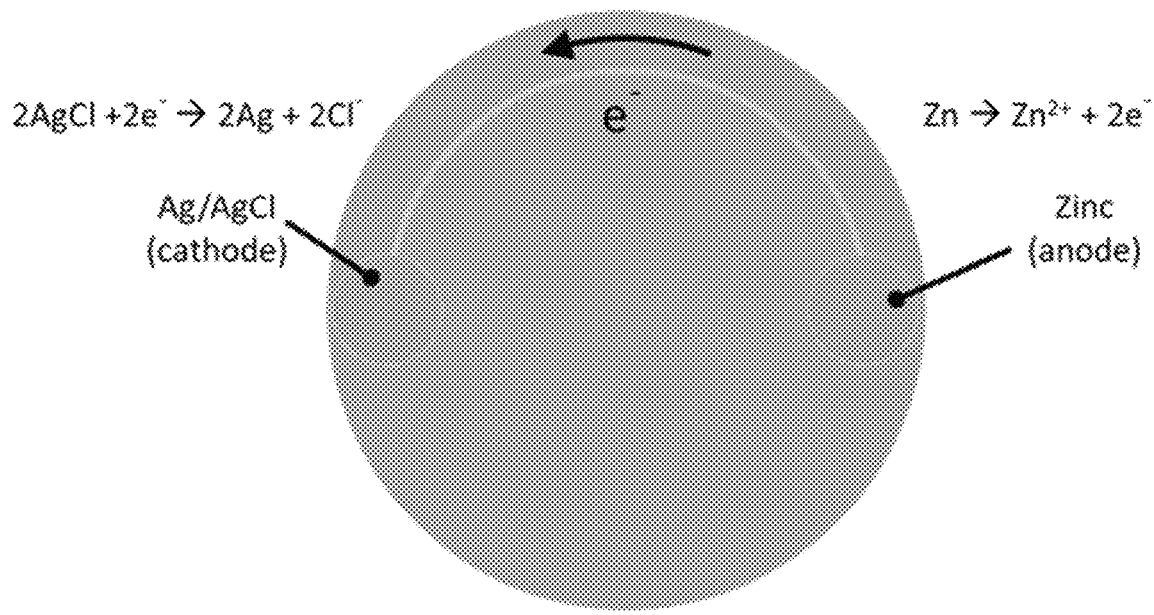
FIGS. 22A-22B show a representative schematic and a photographic image, respectively, of a disclosed ionophoretic ocular delivery device as described in FIGS. 21A-21C.
Figure 22B:
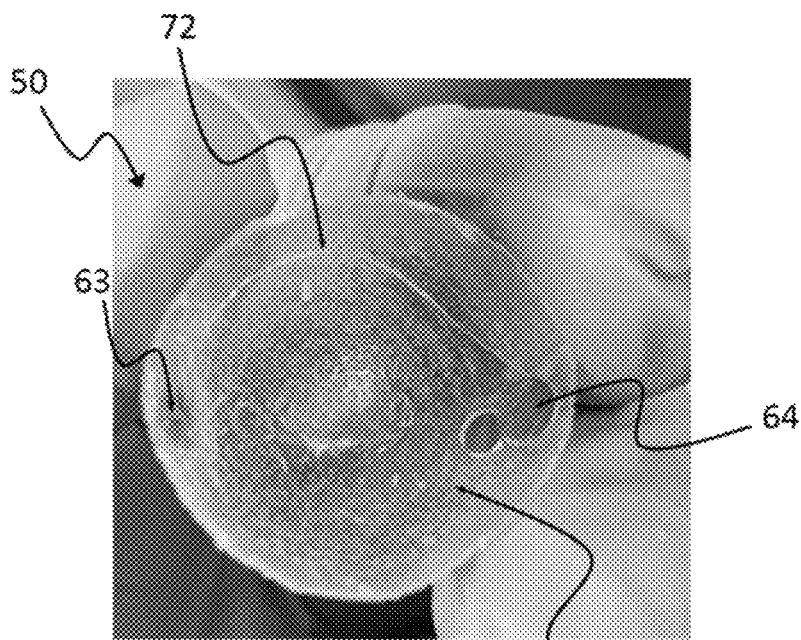

Referring now to FIGS. 21A-21C, which show representative views of a disclosed ionophoretic ocular delivery device. FIG. 21A shows a top view of a disclosed ionophoretic ocular delivery device 51 comprising a conducting component 72, e.g. conductive metal or metal alloy, or alternatively, a conductive polymer layer, embedded or disposed on a top lens component 31, and such that the conducting component 72 is in communication with a water-activated battery comprising a cathode component 63 and an anode component 64. The top lens component 31 can further comprise a bottom lens component, as shown in the side cross-sectional views of FIG. 21B. In alternative aspects, a top lens component 31 will not be associated with a bottom lens component, as shown in the side cross-sectional views of FIG. 21C. FIG. 19B shows a side cross-sectional view of a disclosed ionophoretic ocular delivery device 51 comprising a conducting component 72, a water-activated battery comprising a cathode component 63 and an anode component 64, a top lens component 31, and a bottom lens component 32. FIG. 21C shows a side cross-sectional view of a disclosed ionophoretic ocular delivery device 51 comprising a conducting component 72, a water-activated battery comprising a cathode component 63 and an anode component 64, and a top lens component 31.

It is understood that the water-activated battery can be any of several configurations known to the skilled artisan. For example, the water-activated batter can comprise a cathode component comprising silver chloride and an anode component comprising zinc. Other metal compounds can be used for the cathode component and other metals used for the anode, e.g., metal compounds such as cuprous chloride and manganese oxide; and metals such as magnesium, sodium-loaded melanin, iron, and copper. A further useful water-activated battery is that described in U.S. Pat. No. 9,884,011, which is incorporated herein by reference, which is biocompatible and biodegradable. Also, metal wires such as gold embedded in the lens can be used to connect the electrodes instead of the conducting polymer. (see FIG. 21) The design of the gold wire or conductive polymer must be such that the resistance between the electrodes is sufficiently low to allow easy flow of electrons and so the overall current flow is limited by the transport on the tear side.

The water activated battery must be loaded with the drug in conditions that prevent the flow of current. The drug for example can be incorporated into the contact lens prior to polymerization. Alternatively, lenses can be soaked in organic solutions of drug to load the drug into the lens. Drug can be loaded uniformly in the lens or just in the same region as the electrode to increase the fraction of the loaded drug that is transported into the eyes. Many approaches can be used for selective loading including spray painting a surface layer.

In various aspects, the electrodes used in the disclosed ionophoretic ocular delivery devices can comprise gold, silver, platinum, alloys thereof, or mixtures thereof. In alternative aspects, the electrodes used in the disclosed ionophoretic ocular delivery devices can comprise a conductive polymer.

In operation, the disclosed ionophoretic ocular delivery device utilizes a power source, such as an external power source (e.g., as described for FIGS. 14A-18C) or an integral power source, such as a water-activated battery (e.g., as described for FIGS. 19A-22B). In various aspects, the voltage from the power source can be about 0.01 V to about 10 V. In a further aspect, the voltage from the power source can be about 3 V to about 5 V. In various aspects, the current from the power source can be about 0.01 mAmp to about 50 mAmp. In a further aspect, the current from the power source can be about 0.01 mAmp to about 5 mAmp. In a still further aspect, the current from the power source can be about 0.01 mAmp to about 0.5 mAmp.

During operation, the output from the power supply can be switched on and off for a desired period of time. In various aspects, the power can be applied for a period of about 0.01 hours to about 24 hours. In a further aspect, the power can be applied for a period of about 0.5 hours to about 2 hours. Alternatively, the same periods of time can be used for applying the power, but the power can be applied as a pulsed voltage, e.g., with a periodicity of 0.01 msec$^{-1}$ to about 1 min$^{-1}$.

In various aspects, the top lens component 31 and the bottom lens component 32 are each fabricated in a manner similar to a contact lens comprising similar materials as known to one skilled in the art. For example, each of the top lens component 31 and the bottom lens component 32 can be fabricated from polymethyl methacrylate. Alternatively, each of the top lens component 31 and the bottom lens component 32 can be fabricated from a soft lens material. One class of such soft lens materials is described in U.S. Pat. Nos. 2,976,576 and 3,220,960 incorporated herein by reference. These materials are hydrogels of a sparingly cross-linked hydrophilic copolymer comprising a major amount of a monoester of an olefinic acid from the group of acrylic and methacrylic acids having a single olefinic double bond and a minor amount of a polymerizable diester of one of said acids, the diester having at least two olefinic double bonds. A preferred hydrogel disclosed in the aforesaid patent is a slightly cross-linked material comprising a predominant quantity of 2-hydroxyethyl methacrylate. The hydrogel, known as "hema," can used for fabrication of each of the top lens component 31 and the bottom lens component 32. Hema is characterized by its ability to absorb water of hydration, typically from about 35 to 65% by weight of the hydrogel. Further useful soft lens materials are those described in U.S. Pat. No. 4,401,372, which is incorporated herein by reference.

In U.S. Pat. No. 4,056,496, and incorporated herein by reference, discloses hydrogels suitable for fabrication of each of the top lens component 31 and the bottom lens component 32. The hydrogels in the aforementioned patent are formed from a hydrophilic monomer from the group of dihydroxyalkyl acrylates and methacrylates (collectively the "dihydroxy acrylate"), a substantially water insoluble monomer from the group of alkyl acrylates and methacrylates (collectively "the acrylate") and preferably, a minor amount of an epoxidized alkyl acrylate or methacrylate (collectively the "epoxidized acrylate"). The dihydroxyalkyl acrylate is preferably used in major amount, the alkyl acrylate in minor amount, and the epoxidized acrylate in an amount sufficient to impart the desired rigidity. The polymer is formed by a free radical, bulk polymerization process in the substantial absence of solvent in order to obtain a polymer suitable for fabrication of each of the top lens component 31 and the bottom lens component 32.

Numerous other soft lens materials are known and include cross-linked poly(hydroxyethyl methacrylate) and a cross-linked copolymer of hydroxyethyl methacrylate grafted onto a poly(vinyl pyrrolidone) backbone. Still other soft lens materials and processes for their formation are reported in the following U.S. Pat. Nos. 3,532,679; 3,639,524; 3,647,736; 3,721,657; 3,758,448; 3,767,731; 3,772,235; 3,803,093; 3,816,571; 3,822,196; 3,839,304 and 3,841,985, all incorporated herein by reference.

In various aspects, each of the top lens component 31 and/or the bottom lens component 32 comprise one or more disclosed therapeutic agents. In a further aspect, the one or more disclosed therapeutic agent is present at a concentration of about 1 µg to about 10 mg/ml. In a still further aspect, the one or more disclosed therapeutic agent is present at a concentration of about 1 mg/ml. In some aspects, each of the top lens component 31 and/or the bottom lens component 32 can further comprise one or more buffering agent. In various aspects, the buffering agent can be a Good's buffer, a pharmaceutically acceptable buffer, or biologically compatible buffer.

In a further aspect, the one or more buffering agent is at least one Good's buffer selected from the group consisting of N,N-bis(2-hydroxyethyl)-2-aminoethanesulfonic acid (BES), N,N-bis(2-hydroxyethyl)glycine (Bicine), N-cyclohexyl-2-aminoethanesulfonic acid (CHES), 3-[N,N-bis(2-hydroxyethyl)amino]-2-hydroxy-1-propanesulfonic acid (DIPSO), 3-[4-(2-hydroxyethyl)-1-piperazinyl]propanesulfonic acid (EPPS), 2-[4-(2-hydroxyethyl)-1-piperazinyl]ethanesulfonic acid (HEPES), 2-hydroxy-3-[4-(2-hydroxyethyl)-1-piperazinyl]propanesulfonic acid (HEPPSO), 3-morpholinopropanesulfonic acid (MOPS), piperazine-1,4-bis(2-hydroxy-3-propanesulfonic acid (POPSO), N-tris(hydroxymethyl)methyl-3-aminopropanesulfonic acid (TAPS), 2-hydroxy-N-tris(hydroxymethyl)methyl-3-aminopropanesulfonic acid (TAPSO), N-tris(hydroxymethyl)methyl-2-aminoethanesulfonic acid (TES), and N-[tris(hydroxymethyl)methyl]glycine (Tricine). In a still further aspect, the at least one Good's buffer is selected from the group consisting of BES, Bicine, HEPES, HEPPSO, POPSO, and Tricine. In a still further aspect, the one or more buffering agent comprises HEPES.

In a further aspect, the one or more buffering agent is at least one pharmaceutically acceptable buffer selected from the group consisting of $K_2HPO_4$, $KH_2PO_4$, $Na_2HPO_4$, $NaH_2PO_4$, $H_2CO_3$, $NaHCO_3$, $Na_2CO_3$, $K_2CO_3$, $CaCO_3$, citrate buffer, acetate buffer, lactate buffer, glycine buffer, aspartate buffer, potassium phosphate, sodium phosphate, sodium acetate, histidine, imidazole, sodium citrate, sodium succinate, ammonium bicarbonate, a carbonate, separately or as a mixture thereof, as well as in combination with any pharmaceutically acceptable acid, e.g. hydrochloric acid, or any pharmaceutically acceptable base, e.g., sodium hydroxide. A pharmaceutically acceptable acid can be a mineral acid, e.g. selected from the group consisting of hydrochloric acid, hydrogen bromide, hydrogen iodide, sulphuric acid, nitric acid, phosphoric acid and the like. As an alternative, the pharmaceutically acceptable acid may be an organic acid, e.g. a sulfonic or carboxylic acid, particularly an alkyl or aryl sulfonic acid or an alkyl or aryl carboxylic acid, such as selected from the group consisting of methanesulfonic acid, p-toluenesulfonic acid, benzenesulfonic acid, acetic acid, tartaric acid, maleic acid, citric acid, benzoic acid, salicylic acid, ascorbic acid and the like.

In a further aspect, the one or more buffering agent is present in an amount from about 0.1 mM to about 2000 mM. In a still further aspect, the one or more buffering agent is present in an amount of about 0.1 mM, about 0.2 mM, about 0.3 mM, about 0.4 mM, about 0.5 mM, about 0.6 mM, about 0.7 mM, about 0.8 mM, about 0.9 mM, about 1.0 mM, about 1.1 mM, about 1.2 mM, about 1.3 mM, about 1.4 mM, about 1.5 mM, about 1.6 mM, about 1.7 mM, about 1.8 mM, about 1.9 mM, about 2.0 mM, about 2.1 mM, about 2.2 mM, about 2.3 mM, about 2.4 mM, about 2.5 mM, about 2.6 mM, about 2.7 mM, about 2.8 mM, about 2.9 mM, about 3.0 mM, about 3.1 mM, about 3.2 mM, about 3.3 mM, about 3.4 mM, about 3.5 mM, about 3.6 mM, about 3.7 mM, about 3.8 mM, about 3.9 mM, about 4.0 mM, about 4.1 mM, about 4.2 mM, about 4.3 mM, about 4.4 mM, about 4.5 mM, about 4.6 mM, about 4.7 mM, about 4.8 mM, about 4.9 mM, about 5.0 mM, about 5.1 mM, about 5.2 mM, about 5.3 mM, about 5.4 mM, about 5.5 mM, about 5.6 mM, about 5.7 mM, about 5.8 mM, about 5.9 mM, about 6.0 mM, about 6.1 mM, about 6.2 mM, about 6.3 mM, about 6.4 mM, about 6.5 mM, about 6.6 mM, about 6.7 mM, about 6.8 mM, about 6.9 mM, about 7.0 mM, about 7.1 mM, about 7.2 mM, about 7.3 mM, about 7.4 mM, about 7.5 mM, about 7.6 mM, about 7.7 mM, about 7.8 mM, about 7.9 mM, about 8.0 mM, about 8.1 mM, about 8.2 mM, about 8.3 mM, about 8.4 mM, about 8.5 mM, about 8.6 mM, about 8.7 mM, about 8.8 mM, about 8.9 mM, about 9.0 mM, about 9.1 mM, about 9.2 mM, about 9.3 mM, about 9.4 mM, about 9.5 mM, about 9.6 mM, about 9.7 mM, about 9.8 mM, about 9.9 mM, about 10 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 46 mM, about 47 mM, about 48 mM, about 49 mM, about 50 mM, about 51 mM, about 52 mM, about 53 mM, about 54 mM, about 55 mM, about 56 mM, about 57 mM, about 58 mM, about 59 mM, about 60 mM, about 61 mM, about 62 mM, about 63 mM, about 64 mM, about 65 mM, about 66 mM, about 67 mM, about 68 mM, about 69 mM, about 70 mM, about 71 mM, about 72 mM, about 73 mM, about 74 mM, about 75 mM, about 76 mM, about 77 mM, about 78 mM, about 79 mM, about 80 mM, about 81 mM, about 82 mM, about 83 mM, about 84 mM, about 85 mM, about 86 mM, about 87 mM, about 88 mM, about 89 mM, about 90 mM, about 91 mM, about 92 mM, about 93 mM, about 94 mM, about 95 mM, about 96 mM, about 97 mM, about 98 mM, about 99 mM, about 100 mM, about 150 mM, about 200 mM, about 250 mM, about 300 mM, about 350 mM, about 400 mM, about 450 mM, about 500 mM, about 550 mM, about 600 mM, about 650 mM, about 700 mM, about 750 mM, about 800 mM, about 850 mM, about 900 mM, about 950 mM, about 1000 mM, about 1100 mM, about 1150 mM, about 1200 mM, about 1250 mM, about 1300 mM, about 1350 mM, about 1400 mM, about 1450 mM, about 1500 mM, about 1550 mM, about 1600 mM, about 1650 mM, about 1700 mM, about 1750 mM, about 1800 mM, about 1850 mM, about 1900 mM, about 1950 mM, about 2000 mM; or any range of values encompassing the foregoing values; or any combination of the foregoing values.

In a further aspect, the one or more buffering agent has a pKa of about 6.0 to about 8.0. In a still further aspect, the one or more buffering agent has a pKa of about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0; or any range of values encompassing the foregoing values; or any combination of the foregoing values.

In another aspect, the contact lens and the drug solution are packaged individually and combined by the physician just prior to the therapy. This would be particularly preferred when the active compounds are difficult to stabilize particularly under dry conditions. In one aspect, the drug solution can be added to the concavity of the electrode containing lens followed by placement of the lens in the eye.

Therapeutic Agents

In various aspects, a disclosed ionophoretic ocular delivery device be used to deliver a therapeutic agent, such as a drug or a biological, including an antibody therapeutic or therapeutic protein. The therapeutic agent can be any therapeutic agent useful to treat a disease or disorder of the eye. In a further aspect, the therapeutic agent is a tyrosine kinase inhibitor, an antihistamine, an antibiotic, a beta blocker, a steroid, an antineoplastic agent, an antiviral, an immunosuppressive agent, an antioxidant, and combinations thereof. The disclosed ionophoretic ocular delivery devices can be loaded with a variety of agents, including those as disclosed herein.

In various aspects, a therapeutic agent delivered using the disclosed ionophoretic ocular delivery devices are one or more ophthalmological drugs. As used herein, "opthalmological drug" refers to any chemical compound, therapeutic protein, antibody-based therapeutic, siRNA, single- or double-stranded DNA or RNA molecule, that is applied to the eye with the intent of producing a biological response or to treat a disease or condition of the eye.

In various aspects, a therapeutic agent delivered using the disclosed ionophoretic ocular delivery devices are those selected to treat glaucoma and/or ocular hypertension.

In a further aspect, exemplary therapeutic agents delivered using the disclosed ionophoretic ocular delivery devices are those selected to treat glaucoma and/or ocular hypertension include, but are not limited to thrombin inhibitors; antithrombogenic agents; thrombolytic agents; fibrinolytic agents; vasospasm inhibitors; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; antiplatelet agents; antimitotics; microtubule inhibitors; antisecretory agents; active inhibitors; remodeling inhibitors; antisense nucleotides; anti-metabolites; antiproliferatives (including antiangiogenesis agents); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone, triamcinolone, triamcinolone acetonide); non-steroidal anti-inflammatories (NSAIDs, such as salicylate, indomethacin, ibuprofen, diclofenac, flurbiprofen, piroxicam indomethacin, ibuprofen, naxopren, piroxicam and nabumetone). Such anti-inflammatory steroids contemplated for use in the methodology of the present disclosure, include triamcinolone acetonide (generic name) and corticosteroids that include, for example, triamcinolone, dexamethasone, fluocinolone, cortisone, prednisolone, flumetholone, and derivatives thereof.); antiallergenics (such as sodium chromoglycate, antazoline, methapyriline, chlorpheniramine, cetrizine, pyrilamine, prophenpyridamine); anti proliferative agents (such as 1,3-cis retinoic acid, 5-fluorouracil, taxol, rapamycin, mitomycin C and cisplatin); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); antineoplastics (such as carmustine, cisplatin, fluorouracil3; immunological drugs (such as vaccines and immune stimulants); hormonal agents (such as estrogens, -estradiol, progestational, progesterone, insulin, calcitonin, parathyroid hormone, peptide and vasopressin hypothalamus releasing factor); immunosuppressive agents, growth hormone antagonists, growth factors (such as epidermal growth factor, fibroblast growth factor, platelet derived growth factor, transforming growth factor beta, somatotrapin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix; components; ACE inhibitors; free radical scavengers; chelators; antioxidants; anti polymerases; photodynamic therapy agents; gene therapy agents; and other therapeutic agent(s) such as prostaglandins, antiprostaglandins, prostaglandin precursors, including antiglaucoma drugs including beta-blockers such as timolol, betaxolol, levobunolol, atenolol, and prostaglandin analogues such as bimatoprost, travoprost, latanoprost, and the like; carbonic anhydrase inhibitors such as acetazolamide, dorzolamide, brinzolamide, methazolamide, dichlorphenamide, diamox; and neuroprotectants such as lubezole, nimodipine and related compounds; and parasympathomimetrics such as pilocarpine, carbachol, physostigmine and the like.

In various aspects, the disclosed ionophoretic ocular delivery devices can be used to deliver a therapeutic agent for treatment of glaucoma such as miotics, which increase the outflow of fluid (these include Isopto® Carpine, Ocusert®, Pilocar®, and Pilopine®); epinephrines, which also increase the outflow of fluid (these include Epifrin® and Propine®); beta-blockers, which reduce the amount of fluid (these include Betagan®, Betimol®, Betoptic®, Ocupress®, Optipranalol®, and Timoptic®); and carbonic anhydrase inhibitors and alpha-adrenergic agonists, which also reduce the amount of fluid (these include Alphagan®, Iopidine®, and Trusopt®). Prostaglandin analogs, which are also in use, increase the outflow of fluid through a secondary drainage route (these include Lumigan®, Rescula®, Travatan®, and Xalatan®).

In some aspects, a therapeutic agent that can be used with the disclosed ionophoretic ocular delivery devices is latanoprost. Latanoprost is a prostaglandin $F_{2\alpha}$ analogue. Its chemical name is isopropyl-(Z)-7[(1R,2R,3R,5S)3,5-dihydroxy-2-[(3R)-3-hydroxy-5-phenylpentyl]cyclopentyl]-5-heptenoate.

In various aspects, a disclosed drug delivery composition that can be used with a disclosed ionophoretic ocular delivery device comprises a signal transduction inhibitors targeting receptor kinases of the domain families of e.g. VEGFR, PDGFR, FGFR and their respective ligands or other pathway inhibitors like VEGF-Trap (aflibercept), pegaptanib, ranibizumab, sunitinib, ceridanib, pazopanib, bevasiranib, KH-902, mecamylamine, PF-04523655, E-10030, ACU-4429, volociximab, sirolismus, fenretinide, disulfiram, sonepcizumab and/ortandospirone. These agents include, without limitation, antibodies such as Avastin (bevacizumab). These agents also include, by no way of limitation, small-molecule inhibitors such as STI-571/Gleevec (Zvelebil, *Curr. Opin. Oncol., Endocr.* Metab. Invest. Drugs 2000, 2(1), 74-82), PTK-787 (Wood et al., *Cancer Res.* 2000, 60(8), 2178-2189), ZD-6474 (Hennequin et al., 92nd AACR Meeting, New Orleans, Mar. 24-28, 2001, abstract 3152), AG-13736 (Herbst et al., *Clin. Cancer Res.* 2003, 9, 16 (suppl 1), abstract C253), KRN-951 (Taguchi et al., 95th AACR Meeting, Orlando, Fla., 2004, abstract 2575), CP-547,632 (Beebe et al., *Cancer Res.* 2003, 63, 7301-7309), CP-673,451 (Roberts et al., *Proceedings of the American Association of Cancer Research* 2004, 45, abstract 3989), CHIR-258 (Lee et al., *Proceedings of the American Association of Cancer Research* 2004, 45, abstract 2130), MLN-518 (Shen et al., *Blood* 2003, 102, 11, abstract 476), and AZD-2171 (Hennequin et al., *Proceedings of the American Association of Cancer Research* 2004, 45, abstract 4539), PKC412, nepafenac.

In a further aspect, a disclosed drug delivery composition that can be used with a disclosed ionophoretic ocular delivery device comprises a non-steroidal anti-inflammatory agent, such as acetylsalicylic acid (aspirin), salicylic acid, sulindac, indomethacin, naproxen, fenoprofen, ibuprofen, ketoprofen, indoprofen, furobufen, diflunisal, tolmetin, furbiprofen, diclofenac, mefenamic acid, flufenamic acid, meclofenamic acid, fenclozic acid, alclofenac, bucloxic acid, suprofen, fluprofen, cinchophen, pirprofen, oxoprozin, cinmetacin, acemetacin, ketorolac, clometacin, ibufenac, tolfenamic acid, tenclofenac, prodolic acid, clonixin, flutiazin, flufenisal, salicylsalicylic acid, O-(Carbamoylphenoxy)acetic acid, zomepirac, nifluminic acid, lonazolac, fenbufen, carprofen, tiaprofenic acid, loxoprofen, etodolac, alminoprofen, 2-(8-Methyl-10,11-dihydro-11-oxodibenz[b,f]oxepin-2-yl)-propionic acid, and 4-bphenylacetic acid; and combinations thereof.

In a further aspect, a disclosed drug delivery composition that can be used with a disclosed ionophoretic ocular delivery device comprises an tyrosine kinase inhibitor selected from axitinib, cabozantinib, foretinib, regorafenib, pazopanib, ponatinib, motesanib, cediranib, tivozanib, sorafenib, LY2457546, MGCD-265, MGCD-510, pharmaceutically acceptable salts thereof, and any combination of the foregoing. In other aspects, the tyrosine kinase inhibitor is a derivator of the foregoing tyrosine kinase inhibitors.

In a further aspect, a disclosed drug delivery composition that can be used with a disclosed ionophoretic ocular delivery device comprises an antihistamine selected from loradatine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, trimprazine doxylamine, pheniramine, pyrilamine, chiorcyclizine, thonzylamine, and pharmaceutically acceptable salts thereof, and combinations of any of the foregoing. In some aspects, the antihistamine is a derivative of one of the foregoing compounds.

In a further aspect, a disclosed drug delivery composition that can be used with a disclosed ionophoretic ocular delivery device comprises an antibiotic selected from cefazolin, cephradine, cefaclor, cephapirin, ceftizoxime, cefoperazone, cefotetan, cefutoxime, cefotaxime, cefadroxil, ceftazidime, cephalexin, cephalothin cefamandole, cefoxitin, cefonicid, ceforanide, ceftriaxone, cefadroxil, cephradine, cefuroxime, cyclosporine, ampicillin, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, gatifloxacin, ofloxacin, and pharmaceutically acceptable salts thereof, and combinations of any of the foregoing. In some aspects, the antibiotic is a derivative of one of the foregoing compounds.

In a further aspect, a disclosed drug delivery composition that can be used with a disclosed ionophoretic ocular delivery device comprises an antiviral selected from interferon gamma, zidovudine, amantadine hydrochloride, ribavirin, acyclovir, valaciclovir, dideoxycytidine, phosphonoformic acid, ganciclovir, and pharmaceutically acceptable salts thereof, and combinations of any of the foregoing. In some aspects, the antiviral is a derivative of one of the foregoing compounds.

In a further aspect, a disclosed drug delivery composition that can be used with a disclosed ionophoretic ocular delivery device comprises a beta blocker (or beta adrenergic antagonists) selected from acebutolol, atenolol, labetalol, metoprolol, propranolol, timolol, carteolol, levobunolol, metiparanolol, timolol hemihydrate, timolol maleate, β1-selective antagonists such as betaxolol, and pharmaceutically acceptable salts thereof, and combinations of any of the foregoing. In some aspects, the beta blocker is a derivative of one of the foregoing compounds.

In a further aspect, a disclosed drug delivery composition that can be used with a disclosed ionophoretic ocular delivery device comprises an adrenergic agonist, including non-selective and selective adrenergic agonist, such as, but not limited to, apraclonidine, brimonidine, epinephrine borate, epinephrine hydrochloride, and dipivefrin, and the like, or pharmaceutically acceptable salts thereof, and combinations of any of the foregoing. In some aspects, the adrenergic agonist is a derivative of one of the foregoing compounds.

In a further aspect, a disclosed drug delivery composition that can be used with a disclosed ionophoretic ocular delivery device comprises a steroid, including a corticosteroid, selected from cortisone, prednisolone, flurometholone, dexamethasone, medrysone, loteprednol, fluazacort, hydrocortisone, prednisone, betamethasone, prednisone, methylprednisolone, riameinolone hexacatonide, paramethasone acetate, diflorasone, fluocinonide, fluocinolone, triamcinolone, and pharmaceutically acceptable salts thereof, and combinations of any of the foregoing. In some aspects, the steroid is a derivative of one of the foregoing compounds.

In a further aspect, a disclosed drug delivery composition that can be used with a disclosed ionophoretic ocular delivery device comprises an antineoplastic agent selected from adriamycin, cyclophosphamide, actinomycin, bleomycin, duanorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol, taxotere, vinblastine, vincristine, tamoxifen, etoposide, piposulfan, cyclophosphamide, flutamide, and pharmaceutically acceptable salts thereof, and combinations of any of the foregoing. In some aspects, the antineoplastic agent is a derivative of one of the foregoing compounds.

In a further aspect, a disclosed drug delivery composition that can be used with a disclosed ionophoretic ocular delivery device comprises an immunosuppressive agent selected from voclosporin, cyclosporine, azathioprine, tacrolimus, and pharmaceutically acceptable salts thereof, and combinations of any of the foregoing. In some aspects, the immunosuppressive agent is a derivative of one of the foregoing compounds.

In a further aspect, a disclosed drug delivery composition that can be used with a disclosed ionophoretic ocular delivery device comprises an antioxidant selected from ascorbate, alpha-tocopherol, mannitol, reduced glutathione, various carotenoids, cysteine, uric acid, taurine, tyrosine, superoxide dismutase, lutein, zeaxanthin, cryotpxanthin, astazanthin, lycopene, N-acetyl-cysteine, carnosine, gamma-glutamyl-cysteine, quercitin, lactoferrin, dihydrolipoic acid, citrate, $Ginkgo$ $Biloba$ extract, tea catechins, bilberry extract, vitamins E or esters of vitamin E, retinyl palmitate, and pharmaceutically acceptable salts thereof, and combinations of any of the foregoing. In some aspects, the antioxidant is a derivative of one of the foregoing compounds.

In a further aspect, a disclosed drug delivery composition that can be used with a disclosed ionophoretic ocular delivery device comprise other ophthalmological agents. Examples of such other ophthalmological agents include, but are not limited, to carotenoids, such as lycopene, lutein, zeaxanthin, phytoene, phytofluene, carnosic acid; carotenoid derivatives such as carnosol, 6,7-dehydrocarnosic acid, 7-ketocarnosic acid; a zinc source like zinc oxide or a zinc salt like its chloride, acetate, gluconate, carbonate, sulphate, borate, nitrate or silicate salt; copper oxide; vitamin A; vitamin C; vitamin E; β-carotene; and combinations of any of the foregoing.

The disclosed drug delivery composition can comprise a single therapeutic agent or a combination of one or more therapeutic agents. "Combination" means for the purposes of the disclosure not only a dosage form which contains all the active agents (so-called fixed combinations), and combination packs containing the active agents separate from one another, but also active agents which are administered simultaneously or sequentially, as long as they are employed for the prophylaxis or treatment of the same disease.

Methods of Treatment

In various aspects, the present disclosure pertains to methods of treating or preventing a clinical condition. In some aspects, the clinical condition is a disease or disorder of the eye. In a further aspect, the disclosed methods pertain to treatment of an ophthalmological disorder.

In an aspect, the disclosed method comprises delivery of a disclosed therapeutic agent to the eye using a disclosed ionophoretic ocular delivery device for treatment of an ophthalmological disease, disorder, or clinical condition, such as glaucoma, ocular hypertension, inflammation, including intraocular inflammation, keratitis, dry eye, uveitis, ophthalmological bacterial or fungal infections, macular edema, including cystoid macular edema, macular degeneration, blurred vision, herpetic conjunctivitis, blepharitis, retinal or choroidal neovascularization, other proliferative eye diseases, and/or diabetic retinopathy.

Further examples of ophthalmological disorders according to the disclosure include but are not limited to age-related macular degeneration (AMD), choroidal neovascularization (CNV), choroidal neovascular membrane (CNVM), cystoid macula edema (CME), epi-retinal membrane (ERM) and macular hole, myopia-associated choroidal neovascularisation, vascular streaks, retinal detachment, diabetic retinopathy, diabetic macular edema (DME), atrophic changes of the retinal pigment epithelium (RPE), hypertrophic changes of the retinal pigment epithelium (RPE), retinal vein occlusion, choroidal retinal vein occlusion, macular edema, macular edema due to retinal vein occlusion, retinitis pigmentosa, Stargardt's disease, glaucoma, inflammatory conditions of the eye such as e.g. uveitis, scleritis or endophthalmitis, cataract, refractory anomalies such as e.g. myopia, hyperopia or astigmatism and ceratoconus and retinopathy of prematurity. In addition, examples include but are not limited to angiogenesis in the front of the eye like corneal angiogenesis following e.g. keratitis, corneal transplantation or keratoplasty, corneal angiogenesis due to hypoxia (extensive contact lens wearing), pterygium conjunctivae, subretinal edema and intraretinal edema. Examples of age-related macular degeneration (AMD) include but are not limited to dry or non-exudative AMD, or wet or exudative or neovascular AMD. In a further aspect, the ophthalmological disorder is glaucoma. Alternatively, the ophthalmological disorder is retinal ischemia, including either central retinal ischemia or peripheral retinal ischemia.

The eye comprises several structurally and functionally distinct vascular beds, which supply ocular components critical to the maintenance of vision. These include the retinal and choroidal vasculatures, which supply the inner and outer portions of the retina, respectively, and the limbal vasculature located at the periphery of the cornea. Injuries and diseases that impair the normal structure or function of these vascular beds are among the leading causes of visual impairment and blindness. For example, diabetic retinopathy is the most common disease affecting the retinal vasculature, and is the leading cause of vision loss among the working age population in the United States. Vascularization of the cornea secondary to injury or disease is yet another category of ocular vascular disease that can lead to severe impairment of vision.

"Macular degeneration" is a medical term that applies to any of several disease syndromes which involve a gradual loss or impairment of eyesight due to cell and tissue degeneration of the yellow macular region in the center of the retina. Macular degeneration is often characterized as one of two types, non-exudative (dry form) or exudative (wet form). Although both types are bilateral and progressive, each type may reflect different pathological processes. The wet form of age-related macular degeneration (AMD) is the most common form of choroidal neovascularization and a leading cause of blindness in the elderly. AMD affects millions of Americans over the age of 60, and is the leading cause of new blindness among the elderly. It is characterized and usually diagnosed by the presence of elevated levels of two types of cellular debris within the retina, called drusen and lipofuscin.

In a further aspect, the disclosed method pertains to treatment of an ophthalmological disorder selected from the group comprising age-related macular degeneration (AMD), including wet AMD, choroidal neovascularization (CNV), choroidal neovascular membrane (CNVM), cystoid macula edema (CME), epi-retinal membrane (ERM) and macular hole, myopia-associated choroidal neovascularisation, vascular streaks, retinal detachment, diabetic retinopathy, diabetic macular edema (DME), atrophic changes of the retinal pigment epithelium (RPE), hypertrophic changes of the retinal pigment epithelium (RPE), retinal vein occlusion, choroidal retinal vein occlusion, macular edema, macular edema due to retinal vein occlusion, retinitis pigmentosa, Stargardt's disease, glaucoma, inflammatory conditions, cataract, refractory anomalies, ceratoconus, retinopathy of prematurity, angiogenesis in the front of the eye, corneal angiogenesis following keratitis, corneal transplantation or keratoplasty, corneal angiogenesis due to hypoxia (extensive contact lens wearing), pterygium conjunctivae, subretinal edema and intraretinal edema comprising administering a disclosed drug delivery composition comprising a disclosed therapeutic agent. In some aspects, a disclosed method pertains to administering a disclosed drug delivery composition comprising a disclosed therapeutic agent to a subject that has been diagnosed with an opthamlogic disorder. In a further aspect, a disclosed method pertains to administering a disclosed drug delivery composition comprising a disclosed therapeutic agent to a subject that has been diagnosed with one or more of: (i) macular degeneration, (ii) diabetes-related retinopathy, and (iii) pathological vascularization of the cornea secondary to injury or disease.

In a further aspect, the disclosed method pertains to treatment of a posterior eye disease. Examples of posterior eye diseases include but are not limited to age-related macular degeneration (AMD), choroidal neovascularization (CNV), choroidal neovascular membrane (CNVM), cystoid macula edema (CME), epi-retinal membrane (ERM) and macular hole, myopia-associated choroidal neovascularisation, vascular streaks, retinal detachment, diabetic retinopathy, diabetic macular edema (DME), atrophic changes of the retinal pigment epithelium (RPE), hypertrophic changes of the retinal pigment epithelium (RPE), retinal vein occlusion, choroidal retinal vein occlusion, macular edema, macular edema due to retinal vein occlusion, retinitis pigmentosa, Stargardt's disease and retinopathy of prematurity.

In a further aspect, the electrodes on the contact lens could be used to control water transport in the eyes and thus the electrode containing lens would not contain any drug. Many patients suffer from dry eyes or contact lens mediated dry eyes. In many of these patients, increasing tear secretion by drawing fluid out of the cornea or the conjunctiva could be very useful in managing the disease. Pulling fluid out of the cornea could potentially also be useful in reducing the intra ocular pressure, thereby managing glaucoma without using any drug. It is known that tear volume in the eyes is controlled by many complex processes including secretion from lacrimal glands, drainage of tears through the puncta, and transport of tears potentially across the conjunctiva. Applying potential gradients in the contact lens could increase tear secretion due to stimulation of the lacrimal glands. Additionally, applying potential could draw fluid through the conjunctiva due to electro-osmotic transport (e.g., see Ref. 36). For example, a negative potential in the tears can lead to secretion of fluid due to the migration of the positive electrical double layer in the cell-cell junctions which are negative charged due to the phospholipids. Potentially, a zinc-silver chloride water activated battery with silver chloride positioned near the conjunctiva could create such negative potential on the conjunctiva drawing water out to increase tear volume.

Method of Storage and Application

In various aspects, a lens component preloaded with one or more therapeutic agents and optionally preloaded with a buffer and comprising a water activated battery, e.g., a top lens component, can be stored in form that is substantially dry in order to retain activity of the water activated battery. Accordingly, the lens can be hydrated prior to use. In such instances, a lens component with electrodes can be packaged in a dry state, and separately packaged a hydrating solution in which the lens component can be soaked in order to achieve to achieve hydration for comfort. In various aspects, the hydrating solution can contain one or more lubricious agents. In some aspects, the hydrating solution further comprises one or more therapeutic agents, and optionally, one or more buffer agents, each at concentration similar to that for the given agent in the preloaded lens component in order to minimize loss of the one or more therapeutic agents, and optional one or more buffer agents, during hydration. The duration of hydration can typically be about 0.5 hour to about 6 hours. The hydrating solution can further comprise one or more polymers to facilitate comfort of the lens component for a patient using same, and to also reduce the bypass current through the tear film.

In various aspects, a lens component comprising a water activated battery, e.g., a top lens component, is not preloaded with one or more therapeutic agents or a buffer and can be stored in form that is substantially dry in order to retain activity of the water activated battery. Accordingly, the lens can be hydrated and loaded with one or more therapeutic agent, and optionally one or more buffer agent, prior to use. In such instances, a lens component with electrodes can be packaged in a dry state, and separately packaged a hydrating solution in which the lens component can be soaked in order to achieve to achieve hydration for comfort and loading of one or more therapeutic agent, and optionally one or more buffer agent. In various aspects, the hydrating solution can contain one or more lubricious agents. The duration of hydration and loading of the lens component can typically be about 0.5 hour to about 6 hours. The hydrating solution can further comprise one or more polymers to facilitate comfort of the lens component for a patient using same, and to also reduce the bypass current through the tear film.

In various aspects, alternatively, a first lens component that is drug-loaded, and optionally further loaded with a buffer component, e.g., a bottom lens component, does not comprise electrode components and a second lens comprising electrode components, e.g., a top lens component, can be placed on the first lens. In some aspects, the drug loaded lens can be hydrated and packaged as a hydrated lens, and separately the second lens component is dry and packaged separately in a state that is substantially dry, and then hydrated prior to use and placement on the first lens.

In various aspects, alternatively, a first lens component that is not drug-loaded or loaded with a buffer component, e.g., a bottom lens component, does not comprise electrode components and a second lens comprising electrode components, e.g., a top lens component, can be placed on the first lens. In some aspects, the drug loaded lens can be hydrated and packaged as a hydrated lens, and separately the second lens component is dry and packaged separately in a state that is substantially dry, and then hydrated prior to use and placement on the first lens. In this instance, the first lens component is equilibrated with a equilibrating solution comprising one or more therapeutic agents, and optionally, one or more buffer components, prior to use and placement of the second lens component. In some aspects, the first lens component is packaged a state that is substantially dry.

Kits Comprising Ionophoretic Ocular Delivery Devices

In various aspects, the present disclosure pertains to kits comprising a disclosed top lens component that comprises one or more therapeutic agents, and optionally, one or more buffer components, and is in a state that is substantially dry; a disclosed hydrating solution; instructions for hydrating the lens component; and optionally one or more of: (a) a bottom lens component; (b) instructions for use of the top lens component to deliver one or more therapeutic agents; and/or (c) a power source.

In various aspects, the present disclosure pertains to kits comprising a disclosed top lens component that is in a state that is substantially dry; a disclosed equilibrating solution comprising one or more therapeutic agents, and optionally, one or more buffer components; instructions for equilibrating the lens component; and optionally one or more of: (a) a bottom lens component; (b) instructions for use of the top lens component to deliver one or more therapeutic agents; and/or (c) a power source.

In various aspects, the present disclosure pertains to kits comprising a disclosed top lens component that comprises one or more therapeutic agents, and optionally, one or more buffer components, is in a state that is substantially hydrated, and is packaged to minimize drying of the top lens component during storage and shipment; and optionally one or more of: (a) a bottom lens component; (b) instructions for use of the top lens component to deliver one or more therapeutic agents; (c) a disclosed hydrating solution; (d) instructions for hydrating the lens component; and/or (e) a power source.

In various aspects, the present disclosure pertains to kits comprising a disclosed top lens component that is in a state that is substantially hydrated, and is packaged to minimize drying of the top lens component during storage and shipment; a disclosed equilibrating solution comprising one or more therapeutic agents, and optionally, one or more buffer components; instructions for equilibrating the lens component; and optionally one or more of: (a) a bottom lens component; (b) instructions for use of the top lens component to deliver one or more therapeutic agents; and/or (c) a power source.

In various aspects, the present disclosure pertains to kits comprising a disclosed top lens component that comprises one or more therapeutic agents, and optionally, one or more buffer components, and is in a state that is substantially dry and comprises a water-activated battery component; a disclosed hydrating solution; instructions for hydrating the lens component; and optionally one or more of: (a) a bottom lens component; and/or (b) instructions for use of the top lens component to deliver one or more therapeutic agents.

In various aspects, the present disclosure pertains to kits comprising a disclosed top lens component that is in a state that is substantially dry and comprises a water-activated battery component; a disclosed equilibrating solution comprising one or more therapeutic agents, and optionally, one or more buffer components; instructions for hydrating the lens component; and optionally one or more of: (a) a bottom lens component; and/or (b) instructions for use of the top lens component to deliver one or more therapeutic agents.

REFERENCES

Citation of references is made herein throughout corresponding to one or more of the following numbered references. The format for citing the following references is, for example, "Ref. 1" or "Refs. 7-9," which would reference to reference number 1 or reference numbers 7-9 below, respectively. The cited references are herein incorporated in their entirety.

1. Patel, A., Cholkar, K., Agrahari, V. & Mitra, A. K. Ocular drug delivery systems: An overview. World *J. Pharmacol.* 2, 47-64 (2015).
2. del Amo, E. M. & Urtti, A. Current and future ophthalmic drug delivery systems. A shift to the posterior segment. *Drug Discov. Today* 13, 135-143 (2008).
3. Hironaka, K. et al. Design and evaluation of a liposomal delivery system targeting the posterior segment of the eye. *J. Control. Release* 136, 247-253 (2009).
4. Geroski, D. H. & Edelhauser, H. F. Transscleral drug delivery for posterior segment disease. *Adv. Drug Deliv. Rev.* 52, 37-48 (2001).
5. Patel, S. R. et al. Targeted administration into the suprachoroidal space using a microneedle for drug delivery to the posterior segment of the eye. Investig. *Ophthalmol. Vis. Sci.* 53, 4433-4441 (2012).
6. Sasaki, H. et al. Retinal drug delivery using eyedrop preparations of poly-l-lysine-modified liposomes. *Eur. J. Pharm. Biopharm.* 83, 364-369 (2013).
7. Kushwaha, S. K., Saxena, P. & Rai, A. The adsorption of proteins from aqueous solution on solid surfaces. *J. Control. Release* 13, 208-221 (2014).
8. Lee Szeto, G. et al. Microfluidic squeezing for intracellular antigen loading in polyclonal B-cells as cellular vaccines. *Sci. Rep.* 5, 10276 (2015).
9. Berdugo, M. et al. Delivery of antisense oligonucleotide to the cornea by iontophoresis. *Antisense Nucleic Acid Drug Dev.* 13, 107-14 (2003).
10. Ferreira, A. et al. Treatment frequency and dosing interval of ranibizumab and aflibercept for neovascular age-related macular degeneration in routine clinical practice in the USA. *PLoS One* 10, 1-12 (2015).
11. Park, S. J. et al. Intraocular pharmacokinetics of intravitreal vascular endothelial growth factor-Trap in a rabbit model. *Eye* 29, 561-568 (2015).
12. Eljarrat-Binstock, E. & Domb, A. J. Iontophoresis: A non-invasive ocular drug delivery. *J. Control. Release* 110, 479-489 (2006).
13. Nagarwal, R. C., Kumar, R. & Pandit, J. K. Chitosan coated sodium alginate-chitosan nanoparticles loaded with 5-FU for ocular delivery: In vitro characterization and in vivo study in rabbit eye. *Eur. J. Pharm. Sci.* 47, 678-685 (2012).
14. Loftsson, T., Hreinsdóttir, D. & Stefánsson, E. Cyclodextrin microparticles for drug delivery to the posterior segment of the eye: aqueous dexamethasone eye drops. *Jpp* 59, 629-635 (2007).
15. Lee, S. B., Geroski, D. H., Prausnitz, M. R. & Edelhauser, H. F. Drug delivery through the sclera: Effects of thickness, hydration, and sustained release systems. *Exp. Eye Res.* 78, 599-607 (2004).

16. Ambati, J. & Adamis, A. P. Transscleral drug delivery to the retina and choroid. *Prog. Retin. Eye Res.* 21, 145-151 (2002).
17. Martinho, N., Damge, C. & Reis, C. P. Recent Advances in Drug Delivery Systems. 2011, 510-526 (2011).
18. Gaudana, R., Ananthula, H. K., Parenky, A. & Mitra, A. K. Ocular Drug Delivery. *AAPS Jounal* 12, 348-360 (2010).
19. Ogawa, Y. et al. Organic Transdermal Iontophoresis Patch with Built-in Biofuel Cell. *Adv. Healthc. Mater.* 4, 506-510 (2015).
20. Souied, E. H. et al. Non-invasive gene transfer by iontophoresis for therapy of an inherited retinal degeneration. *Exp. Eye Res.* 87, 168-175 (2008).
21. Hao, J., Li, S. K., Liu, C. Y. & Kao, W. W. Y. Electrically assisted delivery of macromolecules into the corneal epithelium. *Exp. Eye Res.* 89, 934-941 (2009).
22. Gibson, D. J., Tuli, S. S. & Schultz, G. S. Dual-Phase Iontophoresis for the Delivery of Antisense Oligonucleotides. *Nucleic Acid Ther.* 27, 238-250 (2017).
23. Patni, M., Puranik, P., Sonawane, A. & Panzade, P. Transdermal iontophoretic delivery of timolol maleate. Brazilian *J. Pharm. Sci.* 48, 819-827 (2012).
24. Lee, H. et al. Device-assisted transdermal drug delivery. *Adv. Drug Deliv. Rev.* (2017). doi:10.1016/j.addr.2017.08.009
25. Münch, S., Wohlrab, J. & Neubert, R. H. H. Dermal and transdermal delivery of pharmaceutically relevant macromolecules. *Eur. J. Pharm. Biopharm.* 119, 235-242 (2017).
26. Margo, C. E. & Lee, A. Fixation of whole eyes: the role of fixative osmolarity in the production of tissue artifact. *Graefe's Arch. Clin. Exp. Ophthalmol.* 233, 366-370 (1995).
27. Klyce, S. D. Electrical profiles in the corneal epithelium. *J. Physiol.* 226, 407-29 (1972).
28. Genina, E. In-vitro study of methylene blue diffusion through the skin tissue. Proc. *SPIE* 4609, 29-36 (2002).
29. Meek, K. M. & Knupp, C. Corneal structure and transparency. *Prog. Retin. Eye Res.* 49, 1-16 (2015).
30. Kostyuk, O. et al. Transparency of the bovine corneal stroma at physiological hydration and its dependence on concentration of the ambient anion. *J. Physiol.* 543, 633-642 (2002).
31. Cheng, X., Tissue, H. C., Pinsky, P. M. & Cheng, X. Cornea and the swelling of polyelectrolyte gels of biological interest. Reports Prog. Phys. 61, 1325-1365 (1998).
32. Zhang, W., Prausnitz, M. R. & Edwards, A. Model of transient drug diffusion across cornea. *J. Control. Release* 99, 241-258 (2004).
33. Cruysberg, L. P. J. et al. In Vitro Human Scleral Permeability of Fluorescein, Dexamethasone-Fluorescein, Methotrexate-Fluorescein and Rhodamine 6G and the Use of a Coated Coil as a New Drug Delivery System. *J. Ocul. Pharmacol. Ther.* 18, 559-569 (2002).
34. Jackson, T. L. et al. Scleral hydraulic conductivity and macromolecular diffusion in patients with uveal effusion syndrome. *Investig. Ophthalmol. Vis. Sci.* 49, 5033-5040 (2008).
35. Balachandran, R. K. & Barocas, V. H. Computer Modeling of Drug Delivery to the Posterior Eye: Effect of Active Transport and Loss to Choroidal Blood Flow. 25, (2008).
36. Zhu H, Chauhan, A, Tear Dynamics, Current Eye Research, 32:177-197, 2007.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Study 1: Delivery of a Compound through the Cornea.

Materials: Mature cadaver rabbit eyes were purchased from Pel-Freez Biologicals (Rogers, AR). The Nile Blue A dye was purchased from Sigma-Aldrich (St. Louis, MO) with a 75% dye content. Electrode materials were either made from generic lead-free, silver bearing solder or was 3D printed with conductive PLA filament (Proto Pasta, Vancouver, WA). Cadaver rabbit eyes were fixed in Margo solution containing paraformaldehyde and glutaraldehyde purchased from Fisher Scientific (Hampton, NH). Soaking agents for lenses included phosphate buffered saline (PBS), 1 M HEPES, a HEPES buffer solution containing sodium chloride, calcium chloride, magnesium chloride, and potassium phosphate were all purchased from Fisher Scientific (Hampton, NH). Commercial contact lenses Acuvue Oasys (14 mm diameter, 8.4 mm base curve, 0.0 power) were used in the study.

Lens Preparation: Contact lenses were loaded by soaking in a Nile Blue A dye solution (1 mg/mL) in DI water for two days. To investigate the effect of buffer, lenses were soaked in either pure HEPES or HEPES buffer for 10 minutes prior to placement on the cadaver eyes. The molecular weight of HEPES is 238 allowing rapid uptake by the contact lenses.

Application of an Electric Field via Contact Lens: Contact lens loaded with a Nile Blue A dye solution (as described above) were placed on the eye, and then two circular electrodes were placed over the lens. The electrodes were attached to a power source set to the desired current (FIG. 1). A syringe pump was configured to gently place a drop of PBS about 30 μL in volume every 30 seconds on the center of the lens to form a thin film on the surface. The thin film prevents drying of the lens and the cornea and also served as an approximate mimic of the in vivo tear film. It was also critical to ensure that the lens was submerged in a liquid film so that bubbling of gases, if any, was easily visible. The field was applied for the desired duration and then the power source was shut down and lenses were removed. Experiments were conducted for three different choice of solutions (DI water, HEPES, HEPES buffer), and each of these cases was explored for three different combinations of current and time, for a total of nine sets, each of which was conducted in triplicate. Control studies were included in which eyes were not exposed to any dye, and another set in which dye loaded lenses were placed on the eyes, but field was not applied. Additionally, in another set, the eyes were exposed directly to 1 mg/mL Nile Blue A dye A solution in DI water for 60 minutes without application of field.

Imaging via Digital Camera and Confocal Fluorescent Microscopy: After the field was removed, the cadaver eyes were imaged by a Nikon DSLR camera and the images were processed through ImageJ to determine whether Nile Blue A dye was delivered to the eye. After direct imaging, each set of cadaver eyes were fixed in Margo formulation[26]. The fixative solution consists of 1% paraformaldehyde and 1.25% glutaraldehyde in PBS and the eyes were submerged for 40 hours to ensure complete fixation. After fixation, the eyes were cross-section in hemispherical form to include both regions of the cornea that were adjacent to the electrodes and put in a glass bottom dish filled with PBS. The dishes were mounted on a Nikon A1 laser scanning confocal microscope to observe the distribution of Nile Blue A dye throughout the cornea. All images were captured and processed with identical imaging properties.

Figure 2:
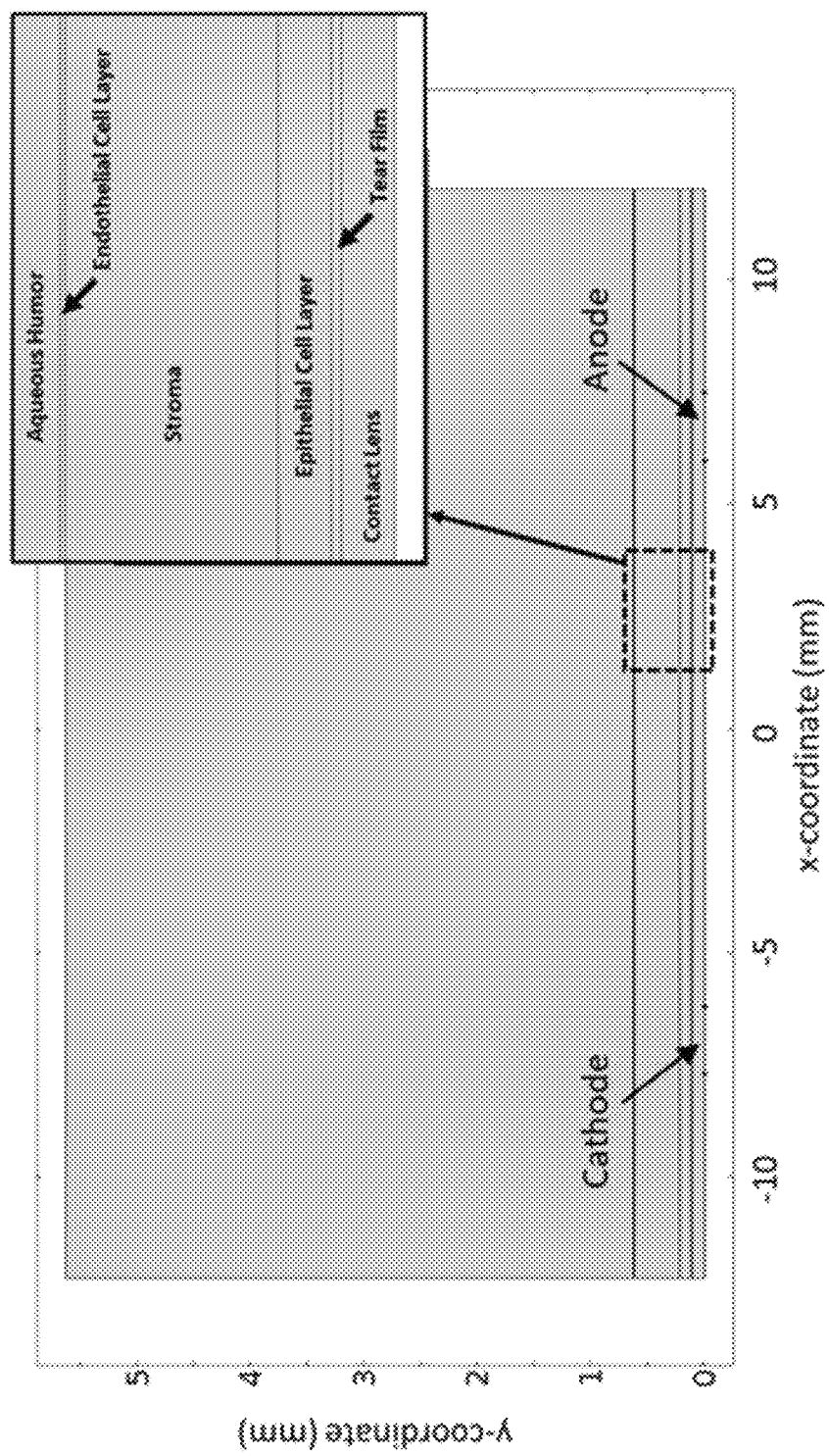
FIG. 2 is a representative model of the electric field distribution through the cornea that was constructed to probe the feasibility of having two electrodes on a single contact lens. The geometry of the simplified layers of the cornea and the electrodes that provide an electric field are shown. The enlarged inset (upper right of the figure) depicts the layers of the cornea, the tear film, and contact lens.

Model of Electric Field Distribution: A simplified model of the electric field distribution through the cornea was constructed to probe the feasibility of having two electrodes on a single contact lens (FIG. 2). The model was constructed using COMSOL Multiphysics® software (COMSOL, Inc., Burlington, Massachusetts), a general-purpose platform software for modeling engineering applications. The geometry of the cornea and contact lens with embedded electrodes were approximated as a flat surface for simplicity. The geometry incorporated all layers of the corneal tissue, the tear film, and contact lens using the values given in Table 1. These values were used in the dimensional analysis and scaling comparison to approximate the bioavailability of Nile Blue A dye in the cornea. The electric field was generated using the 'AC/DC' module of the modeling software with a fixed current density from one electrode at a value translating to an overall current of 0.125 mA which was a value used in ex vivo experiments.

TABLE 1

| Parameter | Symbol | Value | Units |
|---|---|---|---|
| distance between electrodes | $\ell$ | $10^{-2}$ | [m] |
| thickness of lens | $h_L$ | $10^{-4}$ | [m] |
| thickness of tear film | $h_T$ | $10^{-5}$ | [m] |
| thickness of epithelial layer | $h_{EP}$ | $10^{-4}$ | [m] |
| thickness of stroma | $h_S$ | $4 \cdot 10^{-4}$ | [m] |
| thickness of endothelial layer | $h_{END}$ | $3 \cdot 10^{-4}$ | [m] |
| thickness of aqueous humor | $h_{AQ}$ | $10^{-3}$ | [m] |
| resistivity of contact lens | $\rho_L$ | $4 \cdot 10^{-3}$ | [S/m] |
| resistivity of tear film | $\rho_T$ | 1.5 | [S/m] |
| resistivity of epithelial layer* | $\rho_{EP}$ | $4 \cdot 10^{-4}$ | [S/m] |
| resistivity of stroma* | $\rho_S$ | 0.2 | [S/m] |
| resistivity of endothelial layer* | $\rho_{END}$ | $6.6 \cdot 10^{-3}$ | [S/m] |
| resistivity of aqueous humor | $\rho_{AQ}$ | 1.5 | [S/m] |
| diffusivity in tear film | $D_T$ | $10^{-9}$ | [m²/s] |
| diffusivity in epithelial cell layer** | $D_{EP}$ | $5 \cdot 10^{-12}$ | [m²/s] |

*See Ref. 27;
**see Ref. 28.

Imaging Results: The Nile Blue A dye solution was loaded into the lenses of three separate solutions using the methods described above. The first was in deionized water (DI) because the absence of any other salts or buffers results in nearly all of the current through the lens to be carried by the charged drug, therein maximizing the transport. The second was a concentrated HEPES solution which is a zwitterionic buffer that is commonly used in cell biology. The zwitterionic HEPES buffer is ideal for maintaining the pH near the electrodes in spite of the electrodic reaction. The last solution was a concentrated HEPES buffer with common physiological salts to mitigate the changes in stroma. Previous studies have shown that the loss of negatively charged ions lead to a structural change in corneal stroma fibrils which cause a decrease in the transparency of the cornea (e.g., see Refs. 29-31).

Figure 3A:
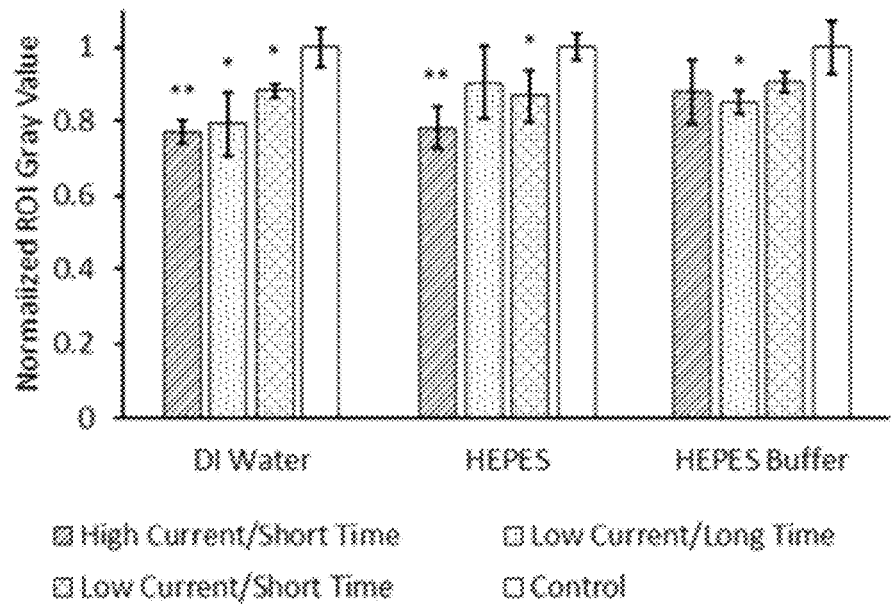
FIGS. 3A-3C show representative region of interest (ROI) analysis of model eyes (cadaver rabbit eyes) after delivery of Nile Blue A dye from disclosed drug loaded lenses. Graphs show the normalized RBG (FIG. 3A) and red (FIG. 3B) ROI values for the cadaver rabbit eyes for all three lens conditions with the three different current and durations and the control eye.
Figure 3B:
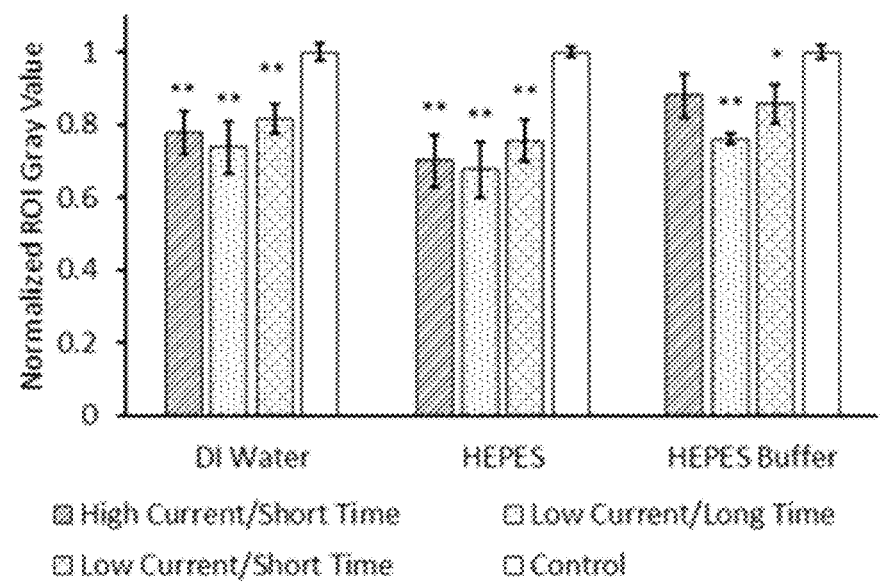
Figure 3C:
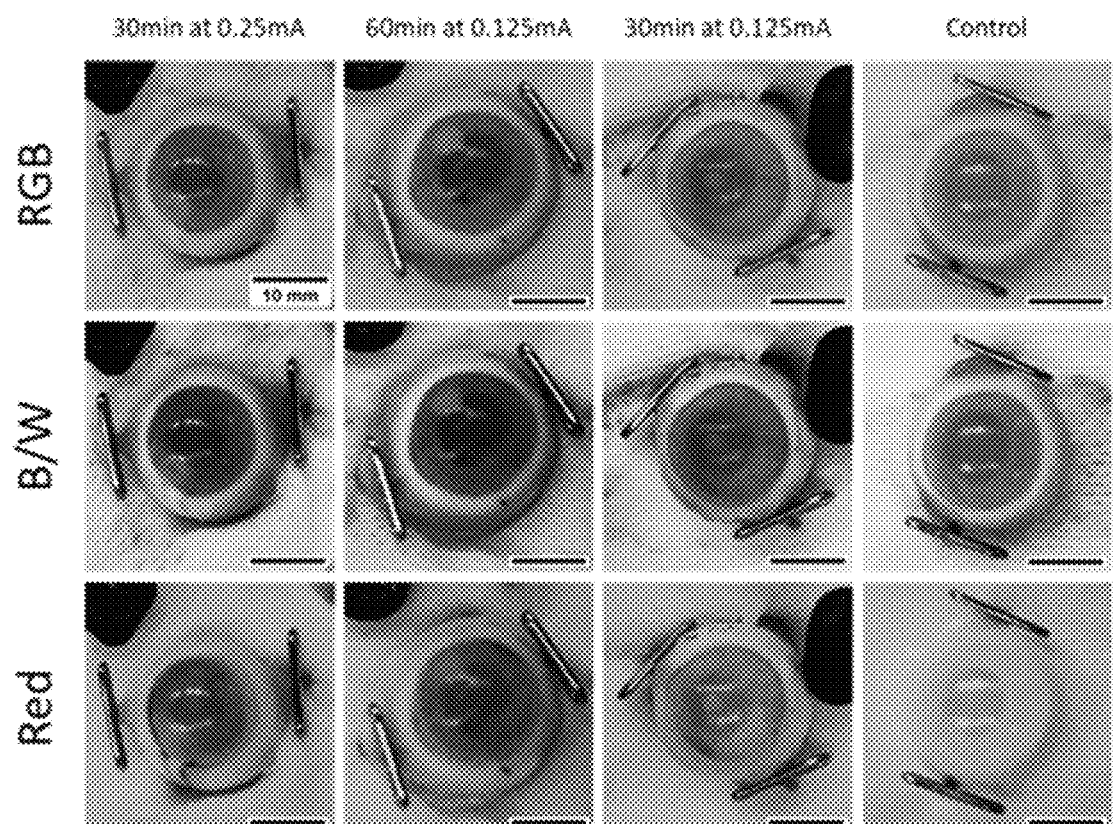

In order to quantify drug delivery, diffusion efficacy was measured by simultaneous comparison of four separate eyes, each corresponding to a different condition. Three of the four eyes had a drug loaded lens and an electric field applied to the system while the fourth served as a control. The eyes used to observe drug transport had lenses that were soaked in the same drug solution to ensure equal loading concentration. The applied electric fields were chosen to achieve 0.25 mA (high current) and 0.125 mA (low current). Samples for lenses soaked in DI water only were ran for either 30 minutes (short time) or 60 minutes (long time). Then samples soaked in HEPES and HEPES buffer solutions were ran for either 60 minutes (short time) or 120 minutes (long time). Upon inclusion of HEPES and HEPES buffer, the drug loaded into the lenses was no longer the dominant carrier of current, therefore requiring a longer time interval for drug delivery. Images after drug delivery were processed through ImageJ and were separated into RGB, red, and B/W channels. (FIG. 3C) The amount of Nile Blue A dye delivered can be seen by the darker ROI that arises from the blue hue produced by the dye. Therefore, as presence of Nile Blue A dye increases, the lower the ROI gray value.

Figure 4A:
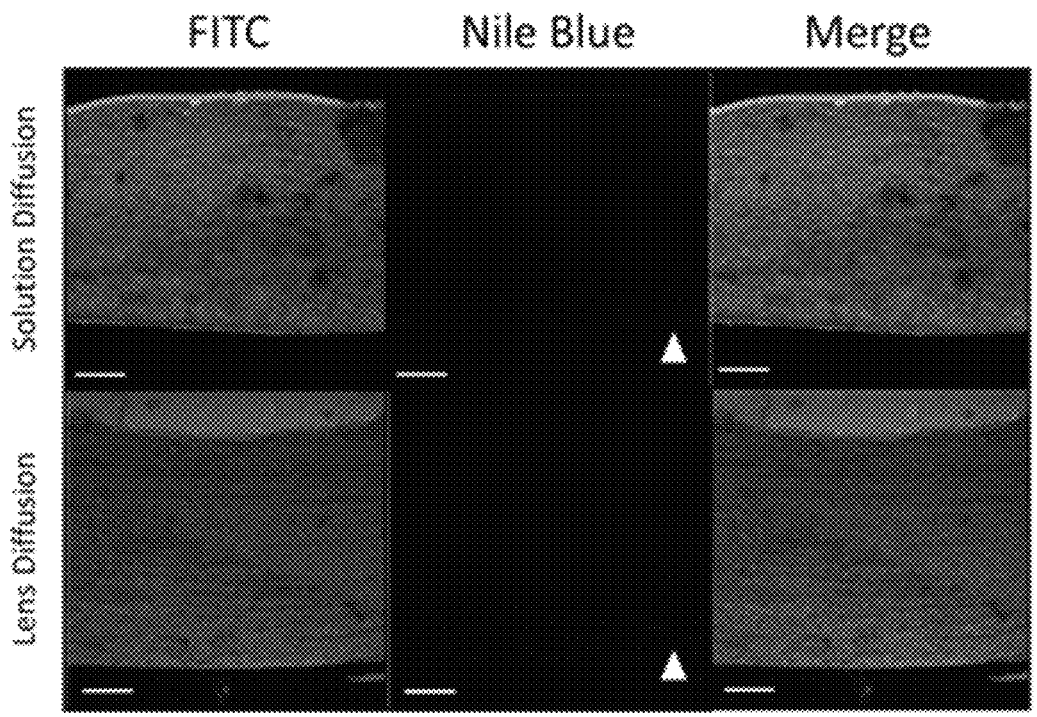
FIGS. 4A-4D are show representative confocal micrographic images of model eyes (cadaver rabbit eyes) after delivery of Nile Blue A dye.
Figure 4B:
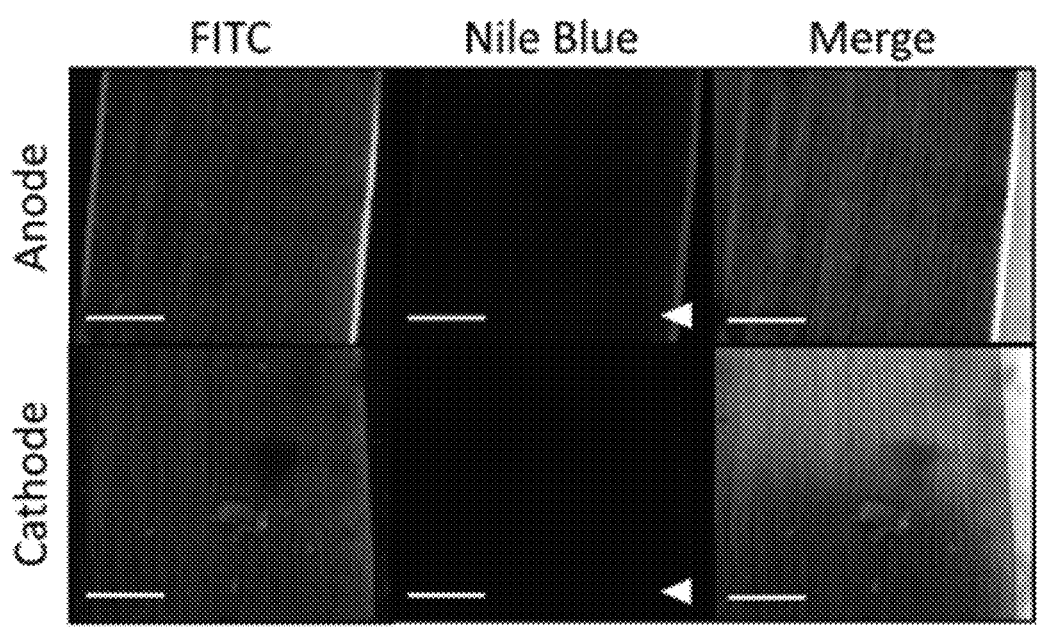
Figure 4C:
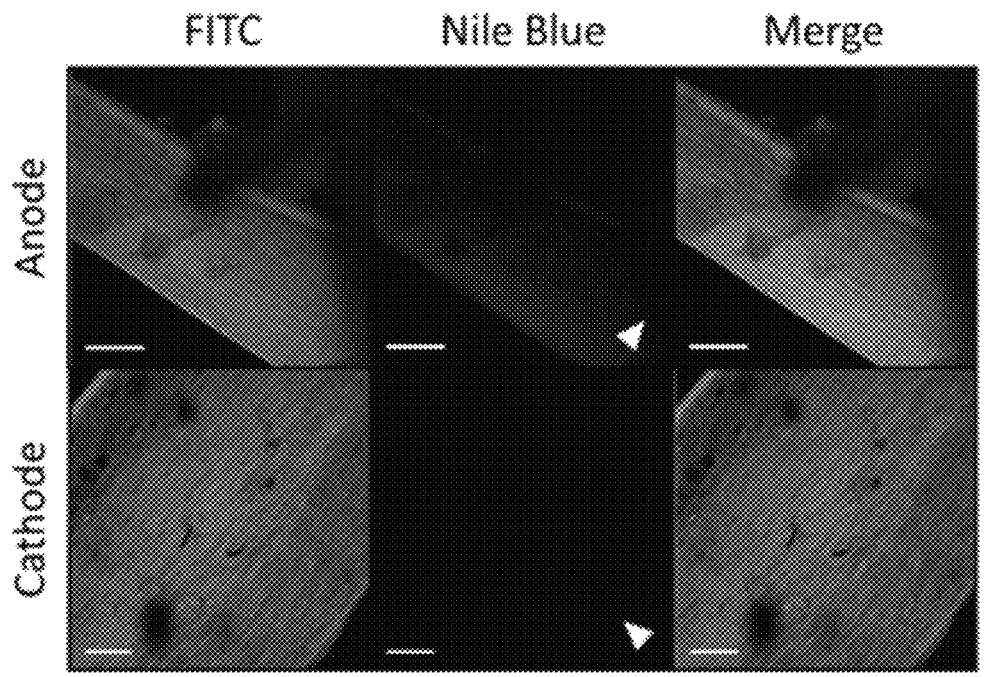
Figure 4D:
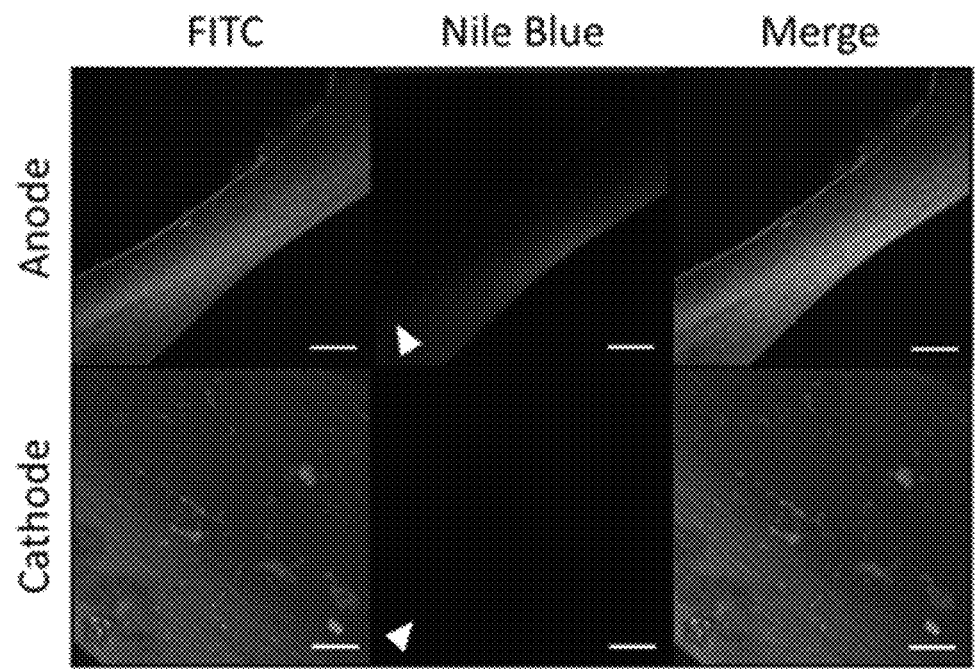

Confocal Fluorescent imaging: In order to observe the transport of a charged species and the distribution throughout the cornea, confocal microscopy of cadaver rabbit eyes was conducted for each lens loading solution used in previous experiments. After the completion of the diffusion experiments, the whole eyes were fixed in a paraformaldehyde and glutaraldehyde solution, preserving the eyes and the Nile Blue A dye solution. After fixation, the eyes were cross-sectioned to include the areas that were adjacent to the electrodes and imaged on a confocal microscope. The FITC channel shows the fibrous structure of the stroma and the regions of high cellular density due to the autofluorescent property of rabbit tissue while the far-red images are of Nile Blue A dye solution (FIGS. 4A-4D). Contrasting the rate of delivery was done by first establishing the intensity and distribution of Nile Blue A dye administered to a cadaver rabbit eye by free solution diffusion and from a drug loaded contact lens for 1 hr (FIG. 4A). Then, the three situations incorporating the electric field at high current for a short time duration with lenses loaded with DI water, HEPES, and HEPES buffer respectively were considered (FIGS. 4B-4D).

Figure 5:
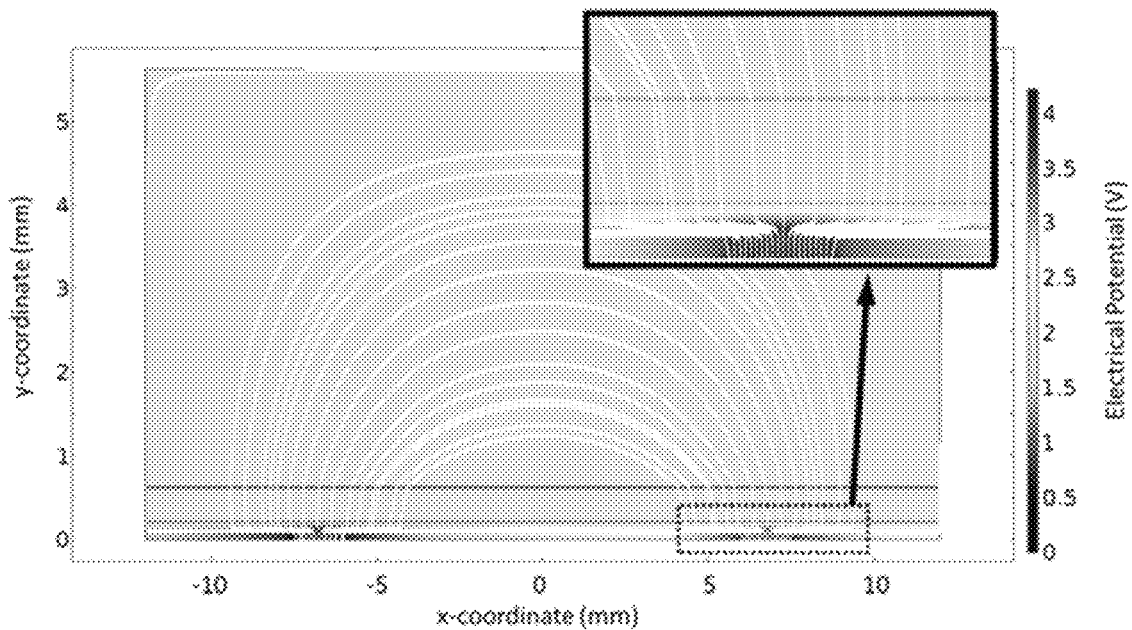
FIG. 5 shows a representative model of electric potential distribution through the anterior of the eye. The model is based on a simplified corneal assembly with electrodes on opposite sides of a disclosed ionophoretic ocular delivery device. The voltage drop can be seen to take place across the contact lens and the epithelial cell layer while the streamlines depict the current path between the electrodes.

Model Simulation for the Distribution of the Electric Field in the Cornea: A model for the distribution of the electric field in the cornea was constructed using COMSOL Multiphysics® software. In the model, the current density from one electrode was fixed at a value translating to an overall current of 0.125 mA which was a value used in ex vivo experiments. The distribution of the electric potential shows that a great deal of the voltage drop is through the contact lens but also the epithelial cell layer. (FIG. 5) The streamlines, depicting the flow of current, indicate that a majoring of the current penetrates through the epithelial and endothelial cell layers and into the aqueous humor. The low voltage drop across all layers past the epithelium demonstrates the drugs of interest would be under less influence from the electric field once in the stroma. This means that the drug is more likely to freely diffuse to the interior of the eye rather than fully following the flow of current to the counter electrode. The model supports the claim about the distribution of the electric field through the cornea and although the model is a 2D simplification, it demonstrates that a physiologically relevant current density (>5 A/m$^2$) can provide substantial current through the front of the eye without short circuiting through the contact lens or the tear film.

Electrophoretic velocity of Nile Blue A dye through the epithelial cell layer: The distribution of Nile Blue A dye in the cornea with an electric field at various currents and time durations can be further explained by a simple analysis of the electrophoretic velocity ($v_{ep}$) (Equation 1). The electrophoretic velocity is mainly a function of the charge of the species (z), the within the epithelium, overall voltage, and the distance between the electrodes.

$$v_{ep} = \frac{zeDV}{kT\ell} \quad \text{(Equation 1)}$$

Due to the hydrophobic nature of Nile Blue A dye, the rate of diffusion is quite small in comparison to hydrophilic drugs when in the epithelium. Using values from Table 1 and assuming a $V_{ep}$ of 2V on a single half of the eye, after 30, 60, and 120 min the total distance travelled in the epithelium is only 69, 139, and 278 μm respectively. In the case of the short time duration, this is roughly only ⅔ of the epithelium. This explains why there is a localization of Nile Blue A dye when the system was applied for a short time duration with a low current for DI water lenses. The Nile Blue A dye had not yet penetrated the epithelial layer and dispersed within the cornea in regions with higher overall diffusion rates. Additionally, this is why there is no overall aggregation of Nile Blue A dye in the region adjacent to the counter electrode for any of the time durations used in the experiments.

Figure 6:
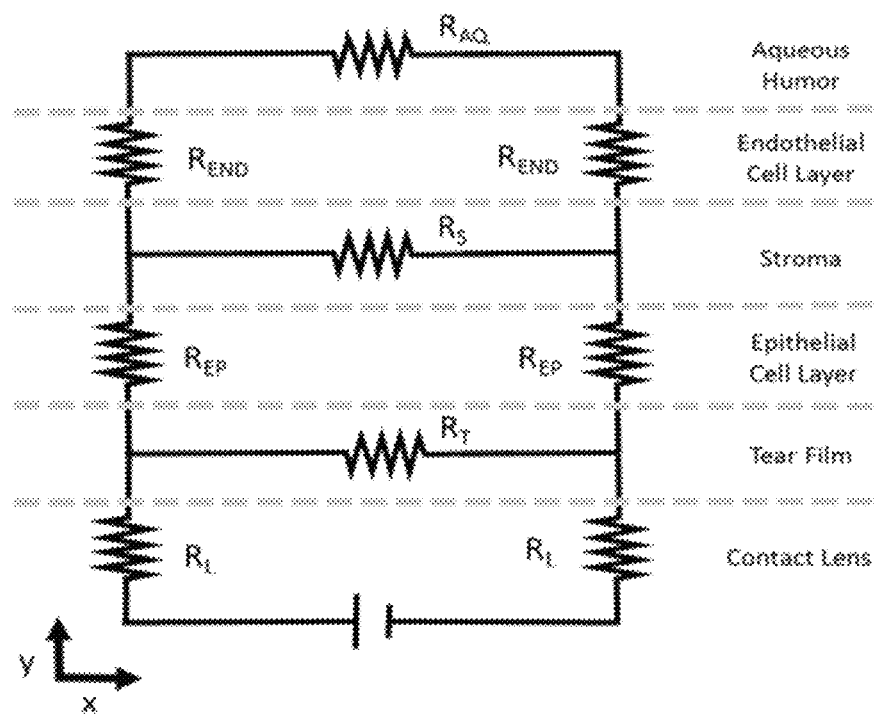
FIG. 6 shows a representative circuit diagram of the cornea. The diagram shows resistive layers of the cornea with a voltage source in the disclosed ionophoretic ocular delivery device while the resistances for each layer of the cornea are oriented in the direction of the dominant potential gradient.

Circuit Equivalent Model for the Electrically Driven Transport of a Drug through the Cornea: An equivalent circuit model of the cornea was constructed using COMSOL Multiphysics® software in order to describe the concentration profiles and determine the relative effect of short circuiting through the tear film. From the model, a fundamental dimensional analysis could estimate the efficacy of drug transport through the cornea and the bioavailability. The model assumes that the cornea can be visualized as a simple circuit diagram with each layer having its own resistance. (FIG. 6)

The first step in understanding the drug transport is to determine the current distribution between the epithelium and the tear film which can be estimated by the ratio of resistances through each layer. The layers with lower resistivity (tear film (T), stroma (S), and aqueous humor (AQ)) will have a predominant current in the x-direction while the layers with higher resistivity (epithelium (EP), endothelium (END), and contact lens (L)) will exhibit current in the y-direction.

$$R_j = \rho_j l / h_j (AQ, S, T) \quad \text{(Equation 2)}$$

$$R_i = \rho_i h_i / l (END, EP, L) \quad \text{(Equation 3)}$$

Each layer of the cornea has a known resistance as a function of resistivity (ρ), the height of the respective layer (h), and the distance between electrodes (l) (Equations 2-3). Taking the ratio of the voltage drop through the tear film and epithelium will determine if the length scale of the tear film is high enough to overcome the resistivity of the epithelial cell layer. The voltage drops ($\Delta V_T$, $\Delta V_{EP}$), were found and approximated using properties from Table 1 as a function of the overall potential (V) applied to the system (Equations 4-5). The ratio of voltage drops was found to be roughly 1 which means that the total resistance through the tear film is on the order as the resistance through the epithelial cell layer and a significant fraction of current passes through the epithelium. If the ratio of voltage drops had been much less than 1, it would mean that the tear film acted as a short-circuit and much of the current would not be able to penetrate the epithelium.

$$\Delta V_T = V \bigg/ \left(1 + \frac{4h_T}{\rho_T L^2}[\rho_L h_L + \rho_{EP} h_{EP}]\right) \quad \text{(Equation 4)}$$

$$\Delta V_{EP} = V / (2 + 2[\rho_L h_L / \rho_{EP} h_{EP}]) \quad \text{(Equation 5)}$$

The next step in determining the bioavailability was to determine the relative time scales for drug transport across the tear film ($\tau_T$) and the epithelium ($\tau_{EP}$). In the case of the time scale for the tear film, the concentration gradient was only be in the x-direction and attributed to the electrophoretic flux as a function of diffusivity ($D_T$), the charge of the drug (e), and the electric potential ($\varphi_T$) (Equation 6). After scaling, substitution, and assuming the potential gradient in the tear film was a constant value ($\varphi_T \sim \Delta V_T$), the time scale for the drug transport across the tear film was characterized as the amount of drug in the tear film over the rate of electrophoretic transport through the tear film (Equation 7).

$$\frac{\partial C}{\partial t} = \frac{D_T e}{kT} \frac{\partial}{\partial x}\left(c \frac{\partial \phi_T}{\partial x}\right) \quad \text{(Equation 6)}$$

$$\tau_T = \frac{kTL^2}{eD_T \Delta V_T} \quad \text{(Equation 7)}$$

In the case of concentration gradient in the epithelium, there was assumed to be no concentration gradient in the x-direction and that the drug transport was purely in the y-direction as a function of the electrophoretic flux driven by the potential gradient (Equation 8). However, since the potential through the epithelium is not constant, the $\partial \varphi_{EP}/\partial y$ term was assumed to be the voltage drop across the epithelium ($\Delta V_{EP}$) over the height of the epithelium ($h_{EP}$). Therefore, the time scale for drug transport across the epithelial cell layer was defined as the amount of drug in the tear film over the rate of electrokinetic transport through the epithelium (Equation 9).

$$\frac{\partial c}{\partial t} = \frac{D_{EP} e}{kT} \frac{\partial}{\partial y}\left(c \frac{\partial \varphi_{EP}}{\partial y}\right) \quad \text{(Equation 8)}$$

$$\tau_{EP} = \frac{kTh_{EP}h_T}{eD_{EP}\Delta V_{EP}} \quad \text{(Equation 9)}$$

$$\tau_T / \tau_{EP} = Z\left(\frac{D_{EP}}{D_T}\right)\left(\frac{\rho_{EP}}{2h_T \rho_T}\right)\left(\frac{l^2 \rho_T + 4h_T[\rho_L h_L + \rho_{EP} h_{EP}]}{[\rho_L h_L + \rho_{EP} h_{EP}]}\right) \quad \text{(Equation 10)}$$

$$\text{Bioavailability} \sim \frac{\tau_T / \tau_{EP}}{1 + \tau_T / \tau_{EP}} \quad \text{(Equation 11)}$$

The time scales for the drug transport across the epithelium ($\tau_{EP}$) and through the tear film ($\tau_T$) characterize the time for the drug in the tear film to either go through the epithelium or to pass through the tear film and aggregate on the counter electrode. Taking the ratio of $\tau_{EP}$ to that of $\tau_T$ characterizes the expected ratio of drug delivered through the epithelium compared to that through the tear film (Equation 10). The relation approximates the bioavailability of the drug, or simply the amount of drug that remains in the tear film compared to the amount of drug that is delivered across the epithelial cell layer and into the stroma (Equation 11). A bioavailability less than 0.5 indicates that most of the drug remains in the tear film due to the shorter time scale in the tear film. However, if the bioavailability is greater than 0.5, then most of the drug is delivered across the epithelium due to the longer time scale in the tear film. Using drug properties for a lipophilic drug (approximated properties of Nile Blue A dye in the cornea)[32] and the electrode configuration used in the experiments, the bioavailability is approximated to be nearly 99%. Meaning that almost all the drug that leaves the lens via electrokinetic transport follows the electric field through the epithelium instead of short circuiting through the tear film. As previously shown in the confocal images of the cross-sectioned cadaver rabbit eyes (FIGS. 4A-4D), a large portion of the Nile Blue A dye was transported into the epithelium instead of aggregating near the surface of the counter electrode, supporting the model prediction of almost 100% bioavailability into the cornea. If short circuiting through the tear film was significant, there would be significant Nile Blue A dye in the cornea near the cathode, which was clearly not the case based on both modeling and ex vivo experiments. Therefore, the design with two electrodes on a single drug loaded contact lens shows potential in regards of transport of a charged species into the cornea.

Electric Field through Single Contact Lens Significantly Increased Rate of Drug Delivery in Model Eyes (cadaver rabbit eyes): A drug can passively diffuse through the endothelial and epithelial cell layers and into the aqueous humor but the time scale for drug diffusion can be longer than the residence time of the drug in tears, in which case a majority of the drug is lost through the conjunctiva or tear drainage. An electric field can drive a charged drug or drug solution through diffusive barriers faster and additionally loading the drug in the contact lens can increase the residence time in tears. In ex vivo experiments on cadaver rabbit eyes, a drug loaded lens was placed over the eye and two electrodes, each 3 mm in diameter, were placed near the periphery at opposite sides of the lens. (FIG. 1) A power source, held at constant current, was connected to the electrodes providing the electric field to the system. Nile Blue A dye was chosen as the drug analog due to the positive charge, size comparable to ophthalmic drugs, ease of detection, and the ability to act as a pH indicator. When the pH is either acidic or neutral, Nile Blue A dye has a blue hue. However, when the solution becomes basic (pH=10) the color gradually changes to pink. The ability to visualize the diffusion of the drug and observe the progression of the ionic species generated at the electrodes is ideal for the quantification of drug delivery and monitor the severity of the electrochemical reactions.

Effect of Buffer on Drug Delivery: The Nile Blue A dye delivery shown in FIG. 3C demonstrates that the application of high current for short time and half the current but for double the time have similar drug delivery to the cornea. The Nile Blue A dye is well distributed throughout the cornea near the anode component except for the experiment with low current for a short time. In this case, the Nile Blue A dye is localized to the area where the anode component was placed. Since Nile Blue A dye is a positively charged dye, this is the area the drug would be expected to penetrate the epithelial cell layer, confirming that the drug delivery is noticeably aided by the presence of an electric field and that contributions from passive diffusion were very minor.

In the case of the lenses loaded in DI water, all conditions showed significant quantities of Nile Blue A dye. The cases with high current for a short time and low current for a longer time interval showed very similar values, indicating that the time and magnitude of the current applied has a proportional relationship to the amount of drug delivered. The case with the least amount of Nile Blue A dye delivered compared to the control was the low current for a short time which is expected if the current and duration are proportional to drug delivery. These results clearly indicate that passive diffusion from the lens is insignificant compared to the electrical flux.

The next set of drug loaded lenses were soaked in a concentrated HEPES solution. The trials were conducted at the same currents but for double the amount of time to compensate for the percentage of current now carried by a species other than Nile Blue A dye. The results are similar to those of the DI water lenses in that the case with high current for a short time had the highest amount of drug transport. The general trend also indicates that passive diffusion has negligible contributions for the delivery of Nile Blue A dye. The final set of lenses were soaked in a HEPES buffer that included common salts to balance the transport of ionic species. However, the salts became the notable carrier of current through the system and the only case that consistently saw a significant presence of Nile Blue A dye was with low current for a long time duration while the other cases showed a smaller and similar degree of transport in contrast to each other. This is indicative of passive diffusion becoming a substantial means of transport, although there were still noticeable contributions from the electric field.

Evidence of Damage: There are two potential mechanisms that can cause damage to the cornea. At the cathode, the generation of sodium hydroxide would result in a caustic solution that could cause damage. At the anode, the electric field driven ion flux could cause osmotic swelling or shrinking to reduce the transparency of the cornea. The damage due to swelling or shrinking could be reversible. Detailed analysis of damage to the cells would involve concentration measurements in the tears to determine whether specific chemicals were released from the cells. Also fluorescence staining to measure barrier function and histology to directly visualize the cells would be important. Since this is a preliminary study, we used transparency of the cornea as the first indication for damage.

The damage done to the cornea varied with current and time duration. For contact lenses soaked in DI water, the cornea remained transparent suggesting no significant damage. At high current and short time, the cathode component region remained transparent but there was damage at the anodic region which is a result of the electrochemically generated species. The low current and long-time interval had damage at both the anodic and cathodic regions. This is most likely due to the combination of electrochemically generated species and the change in the stromal fibrils that results in a loss of transparency. This pattern reveals that without any buffer to moderate the electrochemically generated species at the cathode component combined with a sufficiently high enough current and time duration, there will be irreversible damage done to the surface of the cornea. Similarly, with a long enough time duration, the orientation of the corneal stroma fibrils undergoes a structural change and a loss in transparency. Once the eye was re-suspended in PBS for a short time (5-10 minutes) the damage at the anode component would occasionally regress and regain transparency while the damage at the cathode component was typically seen to be unrecoverable.

These patterns were noticeably similar to the cases that incorporated HEPES and HEPES buffer into the lenses but there was no visible damage to the cornea in the region near the cathode. This confirms that a buffering agent can protect the cornea from sodium hydroxide generated at the electrode. Additionally, in these experiments we did not observe any bubbling which suggests that the rate of gas generation was sufficiently small. However, the rearrangement in to the stromal fibrils was persistent in both cases when the electric field was applied for the longer time durations and at high current.

Confocal imaging of cadaver rabbit eyes shows increased concentration gradient of Nile Blue A dye throughout the cornea with an imposed electric field: It has been established that the incorporation of an electric field can significantly increase the rate of the transport of a charged species into the cornea. To characterize the slow rate solely diffusion driven transport, two situations were constructed. The delivery of Nile Blue A dye from a contact lens and the delivery from a standing solution. After 1 hr of administration, very minor amounts of Nile Blue A dye were present throughout the cornea in both cases. The solution diffusion case demonstrated a very uniform distribution of Nile Blue A dye but with very small concentration. The diffusion from the contact lens illustrated a faint gradient in the distribution of Nile Blue A dye with the highest concentration regime at the front of the cornea. This shows that the pure diffusion driven transport has a difficult time penetrating the dense epithelial cellular layer. Once more, there were no indications that a significant amount of Nile Blue A dye had been delivered through the cornea.

Upon incorporating an electric field and the application through the drug loaded lens soaked in DI water (FIG. 4B), the distribution of Nile Blue A dye near the anode component illustrates a high concentration gradient with the peak concentration at the front of the cornea while the concentration decreases as it progresses towards the interior of the eye. In the case of the cathodic region and adjacent area with only pure diffusion, there is only a small degree of Nile Blue A dye localizing near the outer surface with a similar distribution to the anodic region but to a much lesser extent. However, unlike experiments conducted with HEPES in the contact lens (FIGS. 4C-4D), there was no significant change in the thickness of the cornea at either electrode. This is most likely due to the lack of buffering ions in the contact lens that would lead to osmotic differences across the cornea. Therefore, the case with DI water lenses without any buffering agent had the greatest preservation of the stromal structure and had a minimal change in transparency at the anode.

When the drug loaded lenses were pre-soaked in a concentrated HEPES solution (FIG. 4C) with high current for a short time duration, there was no obvious cellular damage to the cornea from the production of sodium hydroxide at the cathode. Similarly, the highest concentration of Nile Blue A dye was at the front of the cornea in the region directly adjacent to the anode. However, the distribution of Nile Blue A dye demonstrated a much more linear gradient throughout the cornea except for the endothelium which was more concentrated than the preceding region of the stroma. This can be attributed to the higher diffusive resistance in the endothelium, leading to greater accumulation of Nile Blue A dye than in the stroma. Then near the cathode, there was no Nile Blue A dye visible which is expected for delivery on a short time scale. Even if the electric field is applied for much longer durations, after the Nile Blue A dye penetrates the endothelium, the drug rapidly diffuses into the aqueous humor. Furthermore, the regions with the highest voltage drop, or the regions through which a majority of current passes are the tear film and epithelial cell layer. This results in an almost negligible amount of the electric field to act on any other area of the cornea. Then in the case of the drug loaded lenses pre-soaked in the HEPES buffer (FIG. 4D) with high current for a short time duration, the results were almost identical to that of the HEPES soaked lenses apart from there being less Nile Blue A dye to penetrate the cornea and there being less accumulation of Nile Blue A dye in the endothelium. Another observation for both the HEPES and HEPES buffer lenses was the variability in the thickness of the cornea near the electrodes. The region near the anode component demonstrated a noticeable decrease in thickness. This can most likely be attributed to the change in osmolarity near the electrodes as the electrochemically generated species permeate the cornea and possibly influence of the electric field on the cells themselves. The change in thickness can also explain the loss in transparency after the completion of the experiments due to the variation in the stromal structure.

The confocal images show that the electric field drives the Nile Blue A dye into the epithelium and potentially into the stroma. After the drug has been deposited through the most significant diffusion barrier, the epithelium, it can passively diffuse through the remaining cornea and into the aqueous humor. Due to the high diffusive resistance through the epithelium compared the remaining cornea, if the drug only penetrates half of the epithelium, the drug has a high likelihood of passing into the interior of the eye rather than diffusing back out through front of the eye. However, it is very apparent that ionic transport and electrochemical reactions have a harmful impact on the viability of the cornea after the drug delivery process.

Lens design to reduce adverse effects from electric field: The results indicate that at high current, electrochemically generate species produce a caustic solution that damages the cornea at the cathode. However, upon incorporation of HEPES, the effects were neutralized. Conflictingly, the HEPES produced an osmotic effect at the anode component that reduced the thickness of the cornea which disrupted the native organization of the collagen matrix in the stroma and resulted in a loss in transparency even though there was some small degree of recovery when the cornea was submerged in PBS for a several minutes. As a result, the most ideal lens would be loaded with HEPES in the area near the cathode component to prevent damage from electrochemically generated species and the area near the cathode component would be loaded with DI water to prevent any osmotic side effects.

Figure 7A:
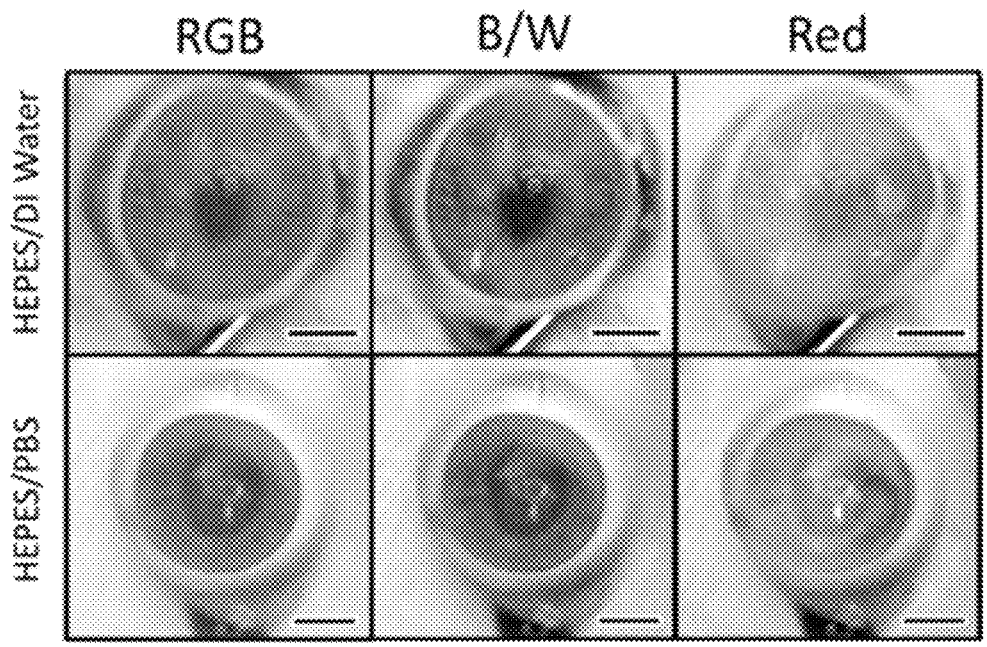
FIGS. 7A-7B show representative data obtained for a disclosed ionophoretic ocular delivery device.
Figure 7B:
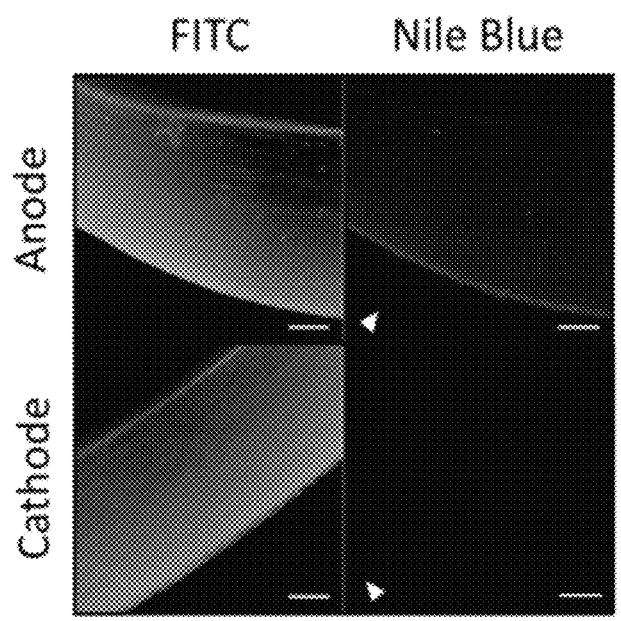

Therefore, a lens was cut in half and one half was soaked in HEPES while the other was soaked in a Nile Blue A dye solution with DI water. Then an electric field was applied at high current for a short time duration, the case with no damage at the anode component with DI water lenses. After completion (FIG. 7A), the cornea had a small deposition of Nile Blue A dye localize at the area adjacent to the anode component and no damage in the area near the cathode. Similarly, a situation with a hybrid lens was constructed but the lens loaded with Nile Blue A dye was soaked in PBS because it is more physiologically acceptable for a contact lens rather than DI water. The results of the PBS hybrid setup, nearly identical to that of the DI water lens which is expected due to the low salt concentrations in PBS. In order to confirm that the cornea was unchanged in thickness during the process, confocal images were taken of the cornea at regions adjacent to the anode component and cathode component (FIG. 7B). The image shows that the structure of the stroma and cellular layers are like that of a healthy corneal cross section. Furthermore, the Nile Blue A dye is well distributed in the region near the anode, similar to previous experiments. This confirms that the hybrid lens design can achieve drug delivery while minimizing the damaging components of the previous trials.

The outcomes of the ex vivo experiments and equivalent circuit analysis suggest that a contact lens containing both the cathode component and the anode component could be useful for iontophoretic based drug delivery to the eye. There are possible benefits of a more compact device that could be easy to use and there may be benefits of higher bioavailability and better predictability because the electrical field distribution can be accurately predicted. However, there are many challenging issues that must be addressed. First, there is certainly a potential for toxicity due to the electrodic reaction that causes a caustic environment at the cathode. This issue can potentially be addressed by using a suitable buffer such as HEPES that is loaded in the contact lens. A high strength buffer is suitable for cathode component but it could cause osmotic swelling at the anode, which is undesirable even though it is likely reversible. Adjusting the ionic strength could potentially manage this issue as well. Integrating both electrodes in a contact lens along with a battery source is challenging but rapid technological advances have already led to contact lenses with electrodes and antennas to generate power wirelessly so it may be feasible to design a compact lens that can be placed on the eye while the patient can continue to blink. While these results are promising, significant issues remain unexplored including detailed toxicity analysis and design of a compact lens containing the power source. Considering the promising results shown here, these other issues will hopefully be explored by researchers interested in drug delivery both to the front and to the back of the eye as well.

Study 2: Delivery of a Compound to the Posterior Region.

Materials: Mature cadaver rabbit eyes were purchased from Pel-Freez Biologicals (Rogers, AR). The Nile Blue A dye (75% dye content) and Fluorescein were purchased from Sigma-Aldrich (St. Louis, MO). Electrode materials were made 3D printed with conductive PLA filament (Proto Pasta, Vancouver, WA). Cadaver rabbit eyes were fixed in Margo solution containing paraformaldehyde and glutaraldehyde purchased from Fisher Scientific (Hampton, NH). Soaking agents for lenses included phosphate buffered saline (PBS) or a HEPES solution purchased from Fisher Scientific (Hampton, NH). Commercial contact lenses Acuvue Oasys (14 mm diameter, 8.4 mm base curve, 0.0 power) were used in the study.

Lens Preparation: Contact lenses were loaded by soaking in a 1 mg/mL Nile Blue solution in PBS or in a 0.01 mg/mL fluorescein solution in HEPES overnight. Lenses were loaded overnight in an enclosed space to prevent photobleaching of any species. Additionally, any lens applied to the electrode that did not possess Nile Blue or fluorescein were soaked for 10 minutes in PBS (if applied to the anode) or HEPES (if applied to the cathode). Both species have low molecular weights and therefore have rapid uptakes into the lenses.

Figure 8:
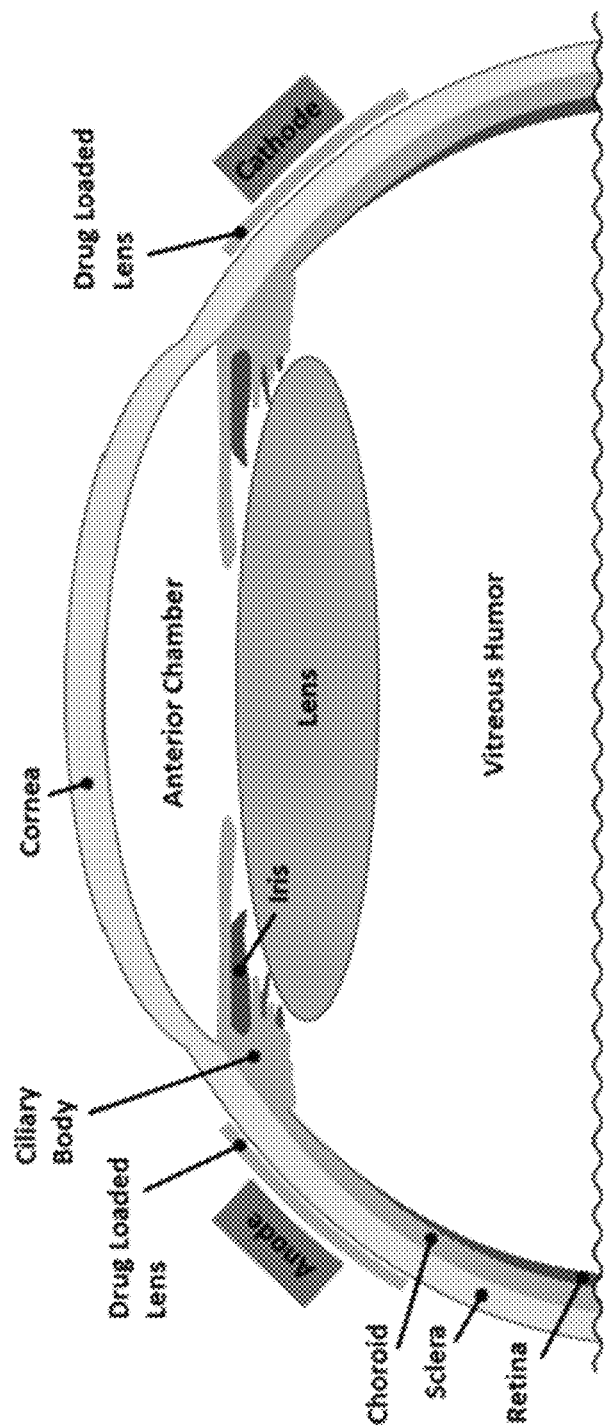
FIG. 8 shows a schematic view of an ex vivo arrangement for a disclosed ionophoretic ocular delivery device comprising a drug-loaded contact lenses and spot electrode configuration on a model eye (cadaver rabbit eye). The electrodes are placed on opposite sides of the sclera just below the site of the ciliary body and muscle and are connected to a constant current power source. The electrodes rested atop the drug loaded contact lenses while a syringe pump supplied a steady droplet system to prevent the lenses from drying out.

Application of Electric Field: Loaded contact lenses were placed at the periphery of the cornea, on the sclera, and the two electrodes were placed over the lenses. Electrodes were attached to a power source that was set to the desired current (FIG. 8). A syringe pump was configured to gently apply a drop of PBS (≈30 µL) every 30 seconds on to the cornea and would flow to the lenses, providing a thin film to keep them hydrated. The application of PBS also served as an approximate mimic of the in vivo tear film. The submersion of the lens was also crucial to ensure that if any bubbling from electrochemically generated gases were to occur, it would be easily visible. The field was applied for the desired duration and then the power source and lenses were removed. Experiments were conducted with the lenses soaked in PBS for the anode component and HEPES for the cathode. The Nile Blue and fluorescein experiments were each conducted with three different combinations of time and current.

Confocal Fluorescent Microscopy Imaging: For observation of Nile Blue delivery, cadaver eyes were fixed in Margo formulation after the conclusion of the experiments. The fixative solution consists of 1% paraformaldehyde and 1.25% glutaraldehyde in PBS and the whole eyes were submerged for 40 hours. After fixation, the eyes were cross-sectioned to include both regions that were adjacent to each electrode and put in a glass bottom dish filled with PBS. The dishes were mounted on a Nikon A1 laser scanning confocal microscope to observe the distribution of the Nile Blue in the regions adjacent to the electrodes. All images were captured and processed with identical imaging properties.

Quantification of Fluorescein Delivery: Delivery of fluorescein to the posterior eye segment was conducted four times for each variation of time and current. After completion, eyes were submerged in PBS for 1 hour and then refrozen. Once the eyes had completely solidified, the vitreous was removed by cutting away the rest of the eye. All samples of same time and current were combined and thawed. After thawing was complete, the vitreous was put through a 0.22 µm filter to ensure no excessive tissue was present in the system. Relative fluorescent intensity of each sample was found using a Quantech fluorometer and the corresponding concentrations of fluorescein was found through a calibration curve.

Figure 9:
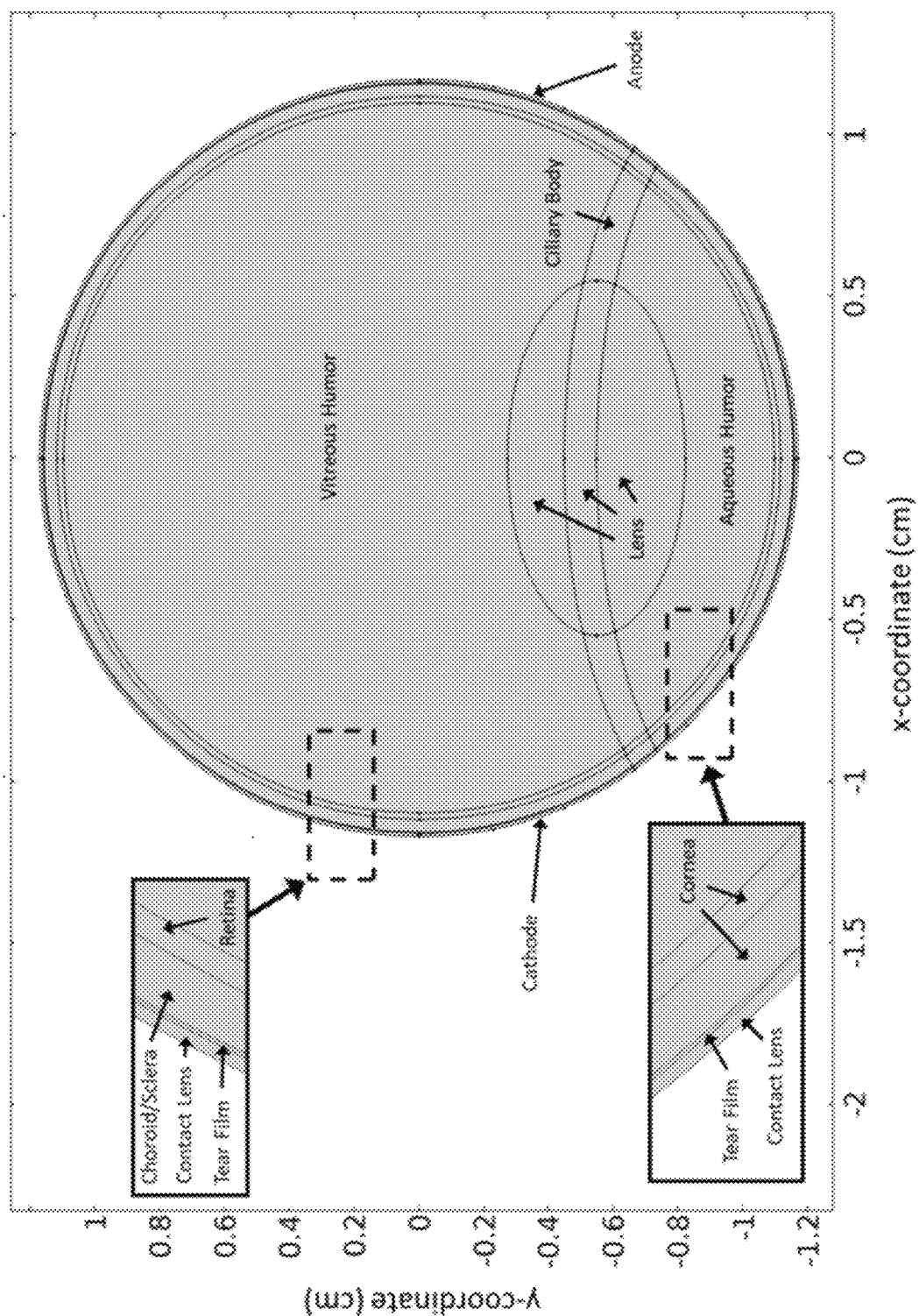
FIG. 9 is shows representative model simulation results for an eye with the disclosed ionophoretic ocular delivery device of FIG. 8. The geometry of a simplified human eye with a contact lens and electrodes to provide an electric field. The enlarged sections depicts the geometry and material in the posterior and anterior segments of the eye.

Model: A simplified COMSOL model was constructed to determine the distribution of the electric field through the eye (FIG. 9). The geometry includes a contact lens with electrodes adjacent to the drug loaded contact lens and the whole eye and was approximated as a flat surface for simplicity. The geometry also incorporated all layers of the posterior eye segment, lens, cornea, and ciliary body with properties from Table 2 below. The electric field was generated using the 'AC/DC' module with a fixed current density from one electrode at 5 mA/cm$^2$ which is the physiological limit for a safe current density.

Table 2 Values used in the COMSOL model, equivalent circuit model, and electrophoretic velocity analysis.

TABLE 2

| Region | Thickness (µm) | Resistivity (Ω * cm) | Relative Permittivity |
|---|---|---|---|
| Contact lens | 100 | 250 | 15 |
| Tear film | 30 | 78 | 80 |
| Sclera and choroid | 400 | 2700 | 150000 |
| Retina | 200 | 4000 | 150000 |
| Vitreous humor | 11000 | 78 | 80 |
| Aqueous humor | — | 78 | 80 |
| Cornea | 600 | $10^6$ | $10^4$ |
| Lens | — | $10^5$ | $10^4$ |
| Ciliary body and iris | — | 3500 | $10^4$ |

Figure 10A:
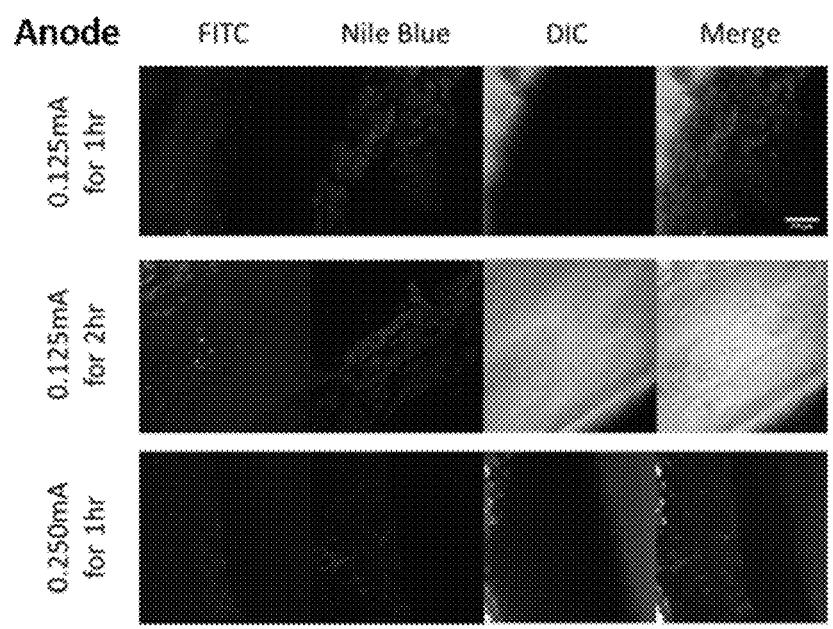
FIGS. 10A-10B show representative confocal micrographic images of a cross-sectioned model eye (cadaver rabbit eye) after iontophoretic delivery of Nile Blue A dye using a disclosed ionophoretic ocular delivery device. The distribution of Nile Blue A dye at various currents and field application times at regions adjacent to the cathode component and anode. Due to the cathodic nature of Nile Blue A dye there is none visible near the cathode component while the area near the anode component demonstrates an even distribution through tissues in the posterior eye segment. The indicated scale bar is: 250 μm.
Figure 10B:
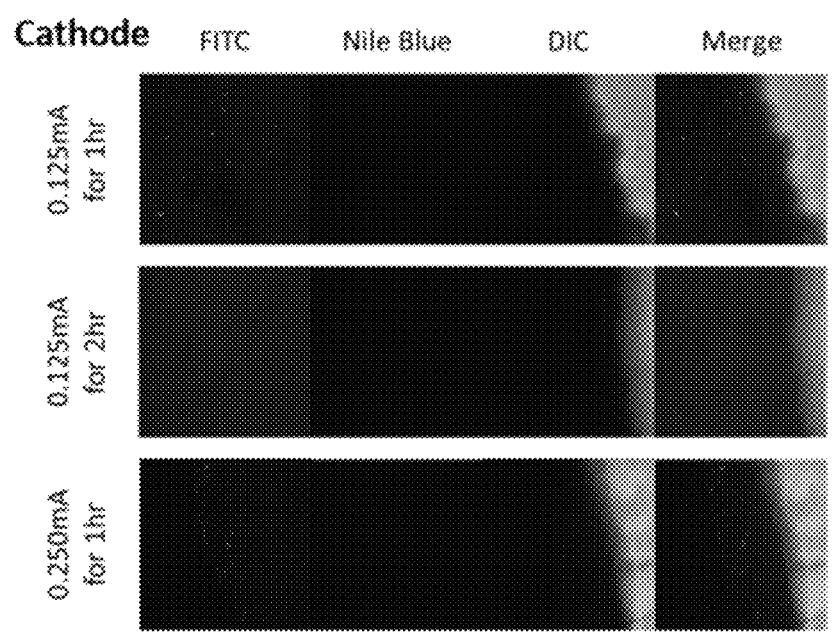

Nile Blue A Dye as an Indicator of Damage and Concentration Gradients: In order to visualize the concentration profile of drugs as they are delivered through the sclera, choroid, and retina, confocal microscopy of cadaver rabbit eyes with Nile Blue A dye loaded contact lenses was conducted for all three sets of currents and time durations (FIGS. 10A-10B). What can be seen is that even at a low current and a short time duration, there was sufficient transport of Nile Blue A dye across all layers of interest. This is further confirmed by the uniform distribution of the Nile Blue A dye through all layers, showing that the delivery from the contact lens was at approximated steady state. It is worth noting that Nile Blue A dye has a very low diffusivity through tissue due to its selective binding to DNA. The absence of a concentration gradient demonstrates that the electric field efficiently delivered the cathodic dye from the lens and was not inhibited by the binding affinity of the Nile Blue A dye.

Efficient transport of fluorescein to the vitreous: The fluorescein was loaded into lenses in a HEPES solution, which alleviated the damage done to the eye during the generation of caustic species from the electrochemical reactions. In order to quantify the delivery of fluorescein to the posterior eye segment, experiments were conducted at three different combinations or time and current and were compared to a control. The electric fields chosen were 0.25 mA (high current) and 0.125 mA (low current) for either 1 hour (short time) or 2 hours (long time). After the application of the electric field to the sclera, the vitreous was harvested and fluorescence was quantified using a fluorometer. The concentrations of fluorescein were found using a calibration curve for the relative fluorescence (Table 3). Additionally in FIGS. 11A-11B, the delivery and localization of fluorescein can be seen in the posterior eye segment. Fluorescence was produced using a UV light source and observed thorough an orange filter. The regions near the cathode component show localizations of fluorescein at the exterior and interior surfaces. The final concentration in the vitreous was also used to calculate the time averaged flux of the fluorescein and the electrophoretic mobility. There was no measurable amount of fluorescein for the control due to the concentration being below the detectable limit of the machine.

Table 3: Fluorescein in the posterior eye segment.

TABLE 3

| | Concentration in Vitreous (ng/ml) | Flux (kg/m²s) [×10⁷] | Electrophoretic Mobility (μm²/Vs) |
|---|---|---|---|
| Control | N/A | N/A | N/A |
| 1 hr 0.250 mA | 70.4 | 14.93 | 13440 |
| 2 hr 0.125 mA | 60.9 | 6.46 | 5820 |
| 1 hr 0.125 mA | 33.8 | 7.18 | 6460 |

Figure 12:
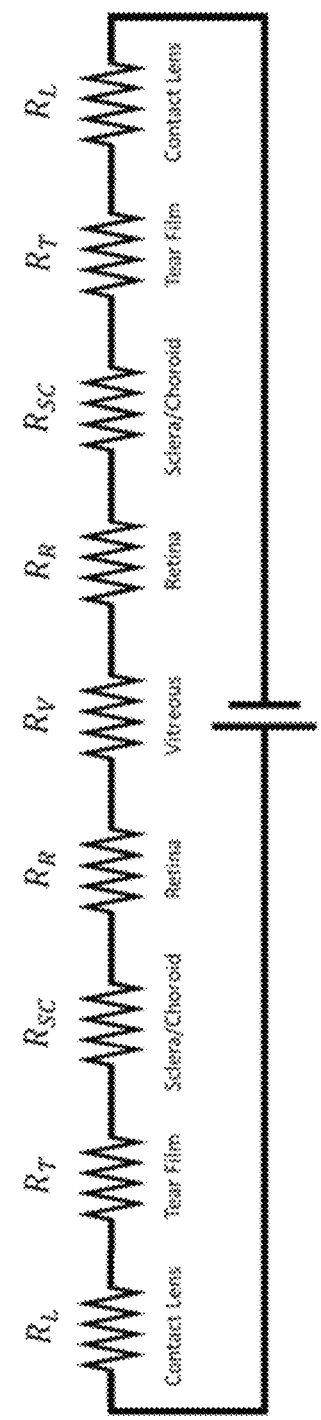
FIG. 12 shows a representative equivalent of the posterior eye segment and a disclosed ionophoretic ocular delivery device. The diagram shows the layers between the spot electrode configuration system. Due to the potential distribution, the resistors are all aligned in series.

Circuit equivalent model: An equivalent circuit model of the contact lens and the posterior eye segment was created to describe the expected distribution of the electric field, regimes of high voltage drop, and the general concentration profile (FIG. 12). The results of a model constructed using COMSOL indicate that all current passes through the posterior eye segment and none short circuits through the contact lens or tear film and does not pass into the anterior region when both electrodes are in the spot configuration. The circuit equivalent model can be used to estimate the efficacy of the drug transport and assist in illustrating areas of greatest potential drop which are the regions where the drug will be most under the influence of the electric field and will assist in deriving the electrophoretic velocity.

First, each layer of the eye needs to have an effective resistance ($R_i$) to the electric field and it can calculated using the resistivity of a layer ($\rho_i$), the thickness of the layer ($h_i$), and the cross-sectional area that the field is passing though (A) which is found in Equation 12 and each resistance can be found using the properties in Table 2.

$$R_i = \frac{\rho_i h_i}{A} \quad \text{(Equation 12)}$$

After finding the resistance of each layer, the ratio of that layer to the total resistance represents the percentage of the voltage drop within that layer. Since the overall potential is known, the potential through a single layer can now be found for the calculation of the electrophoretic velocity.

Electrophoretic Velocity through the Back of the Eye and Transport Efficiency through the Choroid: The trend of fluorescein concentrations in the vitreous where the total fluorescein delivered varies with time and current can be explained by the electrophoretic velocity ($v_{ep}$) (Equation 1). The electrophoretic velocity is a function of the charge of the species (z), the diffusion coefficient of the species (D), the potential (V), and a characteristic length over the potential drop (l).

$$v_{ep} = \frac{zeDV}{kT\ell} \quad \text{(Equation 1)}$$

In the sclera and choroid, fluorescein has a relatively high diffusion coefficient on the order of $10^{-10}$ to $10^{-11}$ m²/s[7,33,34]. Using a diffusion coefficient with a higher literature value, the potential drop found through the circuit equivalent model, and the width of the choroid as the characteristic length, the electrophoretic velocity was found to be roughly 0.35 μm/s. This means that it would take on the order of 10 min for the fluorescein to be delivered through the choroidal space. Using the data from Table 3, the electrophoretic velocity for each case is on the order of 1.3 μm/s and 2.6 μm/s for the low and high current experiments respectively, which is comparable to the theoretical value that was calculated. The difference can be accounted for by passive diffusion of fluorescein into the eye after the electric field was removed from the system. Additionally, the maximum distance covered with the applied current and time durations would only be 10 mm which is only half the width of the eye. This explains why there is no aggregation of fluorescein or Nile Blue at the counter electrodes and remains within the vitreous instead of following the current to completion at the counter electrode.

Additionally, the comparison of the electrophoretic velocity to the rate of uptake in choroidal capillaries will reveal if the delivery of the drug assisted with an electrophoretic driving force. The primary term for comparison is the rate constant for transport across the blood vessels in the choroid (β), which was found to be 1.98·10⁵ s⁻¹ for fluorescein.[35] Proper scaling analysis shows that the appropriate expression for the electrophoretic transport is a function of $v_{ep}$ and the width of the choroid (h) (Equation 13).

$$\frac{1}{\beta} \sim \frac{h}{v_{ep}} \quad \text{(Equation 13)}$$

Direct comparison shows that the rate constant for transport across the blood vessels in the is on the order of nearly 250 times larger than that of the electrophoretic transport.

Meaning that ratio of drug being taken up by the blood vessels to that being transported through the choroid is 1:250. This confirms that the electric field driving the drug delivery is sufficiently overcomes the losses to the choroid and effectively deposits the species of interest into the retina and ultimately the vitreous humor.

Figure 13:
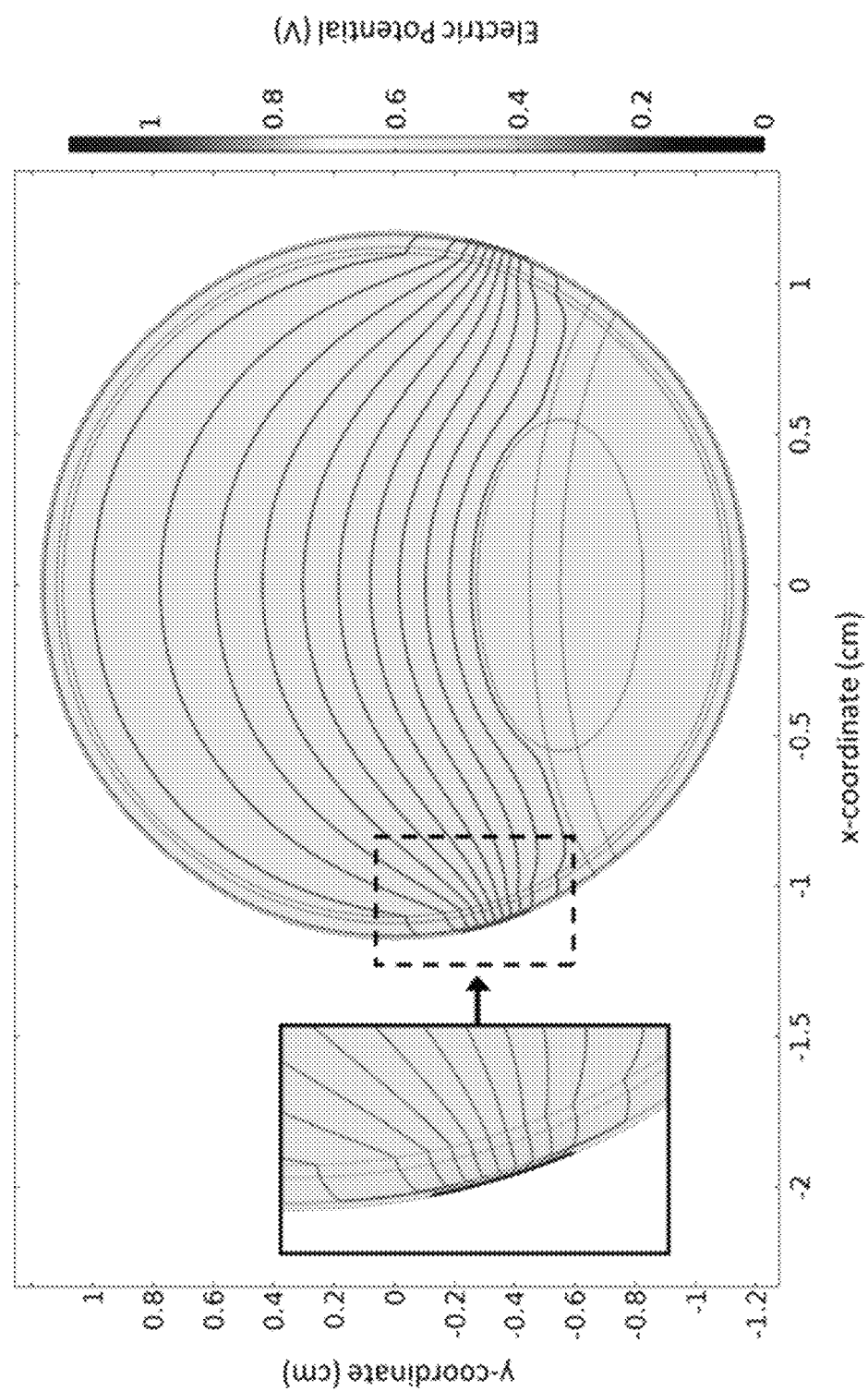
FIG. 13 shows a representative model of electric potential distribution through the eye with a spot electrode arrangement of a disclosed ionophoretic ocular delivery device. The simplified representation of the eye with spot electrodes on either side of the sclera. The voltage drop can be seen to primarily take place through the contact lens and the sclera/choroid region. The streamlines indicate the path of the current, which entirely passes through the vitreous without any short circuiting through the anterior chamber, lens, or tear film.

COMSOL: The current density from one electrode was fixed at a value equivalent to 5 mA/cm$^2$ which is a physiologically safe value for current density in ocular tissue. The distribution of the electric field shows a majority of potential drop through the contact lens and partially through the sclera and choroid (FIG. 13). Additionally, the streamlines indicate the flow of current between the electrodes and that all current penetrates the vitreous humor without any current leakage through the contact lens or to the anterior region of the eye. Furthermore, the negligible voltage drop through the retina and vitreous shows that once the drug of interest reaches the retina, the influence of the electric field will have much less of an effect. Meaning, once the drug reaches these areas, it will be more prone to free diffusion into the surrounding solution rather than following the electric field in its entirety to the counter electrode. The model also shows that the maximum safe current density can be achieved with a relatively low electric potential gradient and that free diffusion will be the primary mechanism of transport once the drug penetrates the sclera.

Electric field through oversized contact lens significantly increases drug delivery through posterior eye tissue: The delivery of drugs to the posterior segment of the eye cannot always be accomplished by passive diffusion, even if there is a concentrated source implanted at the base of the sclera (e.g., see Ref. 35). This is mostly due to the thickness of the sclera and retina along with the blood flow through the choroid which has one of the highest blood flow rates in the human body. These factors result in the need for an additional driving force to enhance the transport of the drugs through the thick and dense tissue in the posterior eye segment. Therefore, the use of an electric field within the limits of physiological acceptability can provide adequate assistance. Here, we used cadaver rabbit eyes with drug loaded lenses and electrodes applied to opposite sides of the posterior region of the eye that supplied the electric field.

In the case of fluorescein, the amount delivered correlated with both the duration and strength of the applied electric field. The results show that reducing the current or the duration by half, nearly half the amount of fluorescein was delivered to the vitreous, revealing a linear relationship between the two factors. This is expected due to the variations in flux and the electrophoretic velocity in regard to the applied field strength and the time scale of the experiments. Additionally, the distribution of Nile Blue A dye was uniform across all applied currents and times due to the high electrophoretic velocity that led to complete delivery across the sclera, choroid, and retina. This confirms that adequate delivery to the back of the eye can be accomplished at very low values of current and on a short time scale.

Absence of Damage to the Posterior Eye Segment after Completion of Drug Delivery: The Nile Blue imaging on a confocal microscope also revealed no apparent damage to any regions of the posterior eye segment. This is an improvement over previously tested delivery through the cornea with electrode embedded contact lenses. Previously, the cornea exhibited changes in size due to osmotic effects that rearranged the stromal structure and reduced transparency. Since there is no tissue similar to the stroma in the posterior eye segment that the current passes through significantly, there is no notable damage done unto the sclera, choroid, or retina.

Previous experiments with the electrode embedded lenses for corneal delivery incorporated a hybrid lens where the contact lens region that would be adjacent to the anode component was either DI water or PBS soaked and the area adjacent to the cathode component was soaked in a HEPES solution. The combination demonstrated efficiency in mitigating the osmotic swelling changes and damage to the epithelium from electrochemically generated species. This system was also implemented in the iontophoretic delivery to the posterior region. However, after the remarkable resistance to any damaging characteristics or concerns, it is possible that a lens soaked in a very low concentrated HEPES solution can prevent caustic damage while also limiting swelling effects which would make the system incredibly novel and robust.

Prophetic Designs for Iontophoretic Contact Lens and Electrode Arrangements: There are two potential electrode arrangements for incorporation into contact lenses. The first is concentric rings (FIG. 14A) which would have one electrode adjacent to the sclera and vitreous while the counter electrode is positioned at the cornea. This design would theoretically maximize the amount of drug delivery due to the large area of the electrodes while not obscuring the vision field and may even increase hydration of the cornea. Additionally, the drug, once inside the vitreous would be limited from flowing to the aqueous humor due to the high impermeability of the ciliary body and muscle. The only potential drawback is the sensitivity of the cornea that might require a separate loading solution or hybrid lens arrangement.

The second design is one that has spot electrodes on either side of the lens and sits adjacent to the sclera (FIG. 14B). This design was the primary setup in all experiments used for delivering fluorescein and Nile Blue to the posterior eye segment. As previously shown in the COMSOL simulation, this electrode arrangement has all of the current passing through the vitreous, leaving on one possible route for the drug delivery. Another benefit is that both electrodes are only passing current and are adjacent to the sclera which has been shown in this study to be highly resistant to damage and osmotic swelling effects under the testing conditions.

The results of the Nile Blue A dye and fluorescein delivery experiments in addition to the COMSOL model and electrophoretic velocity analysis shows that efficient delivery of a drug, hydrophilic or hydrophobic, can be achieved to the posterior eye segment. Not only was a significant amount of drug delivered, there was no noticeable damage to any region adjacent to the electrodes using the hybridized lens configuration. However, it may be possible that a low concentration of HEPES throughout the entire contact lens might be able to achieve the same effect instead of partitioning the HEPES to side of the lens. The final hurdle that needs to be overcome is the complete fabrication of the entire system into a contact lens that provides sufficient current and remains consistent for long periods of time. We hope that this issue can be explored by researchers that are intrigued by the novelty of such a device to deliver drugs to the posterior eye segment while circumventing the use of intravenous injections.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. An ionophoretic ocular delivery device comprising:
   a first electrode;
   a second electrode;
   a top lens component;
   an optional bottom lens component;
   one or more therapeutic agent;
   optionally one or more buffering agent; and
   a power source;
   wherein the first electrode is configured as one or more first spot electrode; and wherein the second electrode is configured as one or more second spot electrode.

2. The ionophoretic ocular delivery device of claim 1, wherein the first electrode is configured as an anode; and wherein the second electrode is configure as a cathode.

3. The ionophoretic ocular delivery device of claim 1, wherein the first electrode is configured as an outer concentric electrode; and wherein the second electrode is configured as an inner concentric electrode.

4. The ionophoretic ocular delivery device of claim 1, wherein the power source is an external power source.

5. The ionophoretic ocular delivery device of claim 1, wherein the power source is an integral power source.

6. The ionophoretic ocular delivery device of claim 4, wherein the integral power source is a water-activated battery.

7. The ionophoretic ocular delivery device of claim 1, wherein the power source is capable of providing a voltage of about 0.01 V to about 10 V; and wherein the power source is capable of providing a current of about 0.01 mAmp to about 50 mAmp.

8. The ionophoretic ocular delivery device of claim 1, wherein the top lens component comprises a polymer or a hydrogel.

9. The ionophoretic ocular delivery device of claim 8, wherein the polymer comprises a polymethyl methacrylate.

10. The ionophoretic ocular delivery device of claim 1, wherein the therapeutic agent is uniformly distributed within the top lens component.

11. The ionophoretic ocular delivery device of claim 1, wherein the therapeutic agent is an opthalmological drug.

12. The ionophoretic ocular delivery device of claim 11, wherein opthalmological drug is a glaucoma therapeutic agent, an ocular hypertension therapeutic agent, or a combination thereof.

13. The ionophoretic ocular delivery device of claim 1, wherein the one or more buffering agent is a Good's buffer.

14. The ionophoretic ocular delivery device of claim 13, wherein the Good's buffer is selected from the group consisting of BES, Bicine, HEPES, HEPPSO, POPSO, and Tricine.

15. The ionophoretic ocular delivery device of claim 1, wherein the first electrode comprises gold, a gold alloy, silver, a silver alloy, platinum, a platinum alloy, a conductive polymer, or mixtures thereof; and wherein the second electrode comprises gold, a gold alloy, silver, a silver alloy, platinum, a platinum alloy, a conductive polymer, or mixtures thereof.

16. The ionophoretic ocular delivery device of claim 15, wherein the first electrode and the second electrode comprise substantially identical materials.

17. A method of treating an ophthalmological disorder, disease, or clinical condition comprising administering one or more therapeutic agent using the ionophoretic ocular delivery device of claim 1, thereby treating the ophthalmological disorder, disease, or clinical condition.

18. The method of claim 17, wherein using the ionophoretic ocular delivery device comprises applying an electric field to the ionophoretic ocular delivery device for a period of from about 0.5 hours to about 2 hours.

19. The method of claim 17, wherein the ophthalmological disorder, disease, or clinical condition is selected from glaucoma, ocular hypertension, inflammation, keratitis, dry eye, uveitis, ophthalmological bacterial infection, ophthalmological fungal infection, macular edema, macular degeneration, herpetic conjunctivitis, blepharitis, retinal neovascularization, choroidal neovascularization, diabetic retinopathy, and combinations thereof.

* * * * *